United States Patent
Weymouth-Wilson et al.

(10) Patent No.: US 10,968,250 B2
(45) Date of Patent: *Apr. 6, 2021

(54) INTERMEDIATES FOR THE SYNTHESIS OF BILE ACID DERIVATIVES, IN PARTICULAR OF OBETICHOLIC ACID

(71) Applicant: NZP UK Limited, Bristol (GB)

(72) Inventors: Alexander Weymouth-Wilson, Reading (GB); Zofia Komsta, Reading (GB); Laura Wallis, Reading (GB); Timothy Evans, Reading (GB); Ieuan Davies, Reading (GB); Carl Otter, Reading (GB); Rhys Batchelor, Reading (GB)

(73) Assignee: NZP UK Limited, Bristol (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/302,059

(22) PCT Filed: May 18, 2017

(86) PCT No.: PCT/GB2017/051385
§ 371 (c)(1),
(2) Date: Nov. 15, 2018

(87) PCT Pub. No.: WO2017/199033
PCT Pub. Date: Nov. 23, 2017

(65) Prior Publication Data
US 2019/0284227 A1    Sep. 19, 2019

(30) Foreign Application Priority Data
May 18, 2016  (GB) ..................... 1608777

(51) Int. Cl.
*C07J 43/00* (2006.01)
*C07J 9/00* (2006.01)
*C07J 21/00* (2006.01)
*C07J 31/00* (2006.01)
*C07J 41/00* (2006.01)
*C07J 51/00* (2006.01)
*C07J 33/00* (2006.01)
*C07J 13/00* (2006.01)
*C07J 17/00* (2006.01)
*C07J 71/00* (2006.01)

(52) U.S. Cl.
CPC .............. *C07J 43/003* (2013.01); *C07J 9/00* (2013.01); *C07J 9/005* (2013.01); *C07J 17/00* (2013.01); *C07J 21/006* (2013.01); *C07J 21/008* (2013.01); *C07J 31/006* (2013.01); *C07J 33/002* (2013.01); *C07J 41/0055* (2013.01); *C07J 41/0061* (2013.01); *C07J 41/0088* (2013.01); *C07J 41/0094* (2013.01); *C07J 51/00* (2013.01); *C07J 71/001* (2013.01); *C07J 13/007* (2013.01)

(58) Field of Classification Search
CPC ... C07J 43/003; C07J 51/00; C07J 9/00; C07J 41/0088; C07J 41/0055; C07J 41/0061; C07J 9/005; C07J 21/006; C07J 21/008; C07J 31/006; C07J 41/0094; C07J 13/007
See application file for complete search history.

(56) References Cited

U.S. PATENT DOCUMENTS 2,624,748 A    1/1953  Levin et al.
4,289,872 A    9/1981  Denkewalter et al.
(Continued)

FOREIGN PATENT DOCUMENTS

CN    105348365 A    2/2016
CN    106279328 A    1/2017
(Continued)

OTHER PUBLICATIONS

Akhrem, Total Synthesis of Steroids, 1970, Plenum Press, New York, N.Y pp. i-362. (Year: 1970).*

(Continued)

*Primary Examiner* — Paul A Zucker
(74) *Attorney, Agent, or Firm* — Morgan, Lewis & Bockius LLP

(57) ABSTRACT

The present invention relates to compounds which are intermediates in the synthesis of bile acid derivatives with pharmacological activity. The invention relates to compounds of general formula (I):

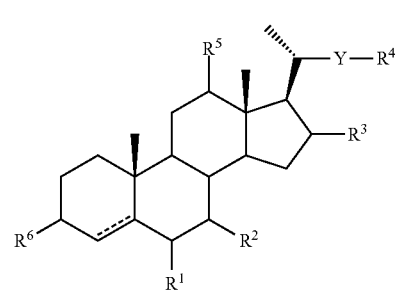

(I)

wherein:

⋰, $R^1$, $R^2$, $R^3$, $R^4$, $R^5$, $R^6$ and Y are as defined herein. The compounds are intermediates in the synthesis of synthetic bile acids which are useful in the treatment of conditions such as liver disease. In addition, the invention relates to a method of synthesizing these intermediates and a method of preparing obeticholic acid and obeticholic acid analogues from the compounds of the invention.

15 Claims, No Drawings

(56) References Cited

U.S. PATENT DOCUMENTS

| | | | |
|---|---|---|---|
| 5,229,490 | A | 7/1993 | Tam |
| 5,643,575 | A | 7/1997 | Martinez et al. |
| 5,932,462 | A | 8/1999 | Harris et al. |
| 10,131,688 | B2 * | 11/2018 | Weymouth-Wilson ............... C07J 71/001 |
| 10,301,350 | B2 * | 5/2019 | Weymouth-Wilson ............... C07J 71/001 |
| 10,538,550 | B2 * | 1/2020 | Weymouth-Wilson ............... C07J 9/005 |
| 2003/0143596 | A1 | 7/2003 | Bentley et al. |
| 2009/0062256 | A1 | 3/2009 | Olson |
| 2010/0063018 | A1 | 3/2010 | Pellicciari et al. |
| 2014/0148428 | A1 | 5/2014 | Pruzanski et al. |
| 2014/0206657 | A1 * | 7/2014 | Yu ............... C07J 9/005 514/177 |
| 2016/0145295 | A1 | 5/2016 | Or et al. |

FOREIGN PATENT DOCUMENTS

| | | | |
|---|---|---|---|
| CN | 106397522 A | 2/2017 | |
| CN | 106478756 A | 3/2017 | |
| CN | 106478759 A | 3/2017 | |
| CN | 106518946 A | 3/2017 | |
| EP | 1568706 A1 | 8/2005 | |
| EP | 1985621 A1 | 10/2008 | |
| EP | 1985621 A1 * | 10/2008 | ............... C07J 17/00 |
| WO | WO 93/21259 A1 | 10/1993 | |
| WO | WO 94/19366 A1 | 9/1994 | |
| WO | WO 96/21469 A1 | 7/1996 | |
| WO | WO 2011/014661 A2 | 2/2001 | |
| WO | WO 02/072598 A1 | 9/2002 | |
| WO | WO 2005/082925 A2 | 9/2005 | |
| WO | 2006/122977 A2 | 11/2006 | |
| WO | WO 2007/095174 A2 | 8/2007 | |
| WO | WO 2008/002573 A2 | 1/2008 | |
| WO | WO 2008/091540 A2 | 7/2008 | |
| WO | WO 2010/014836 A2 | 2/2010 | |
| WO | WO 2010/059853 A1 | 5/2010 | |
| WO | WO 2010/059859 A1 | 5/2010 | |
| WO | WO 2013/192097 A1 | 12/2013 | |
| WO | WO 2014/066819 A1 | 5/2014 | |
| WO | WO 2014/085474 A1 | 6/2014 | |
| WO | WO 2014/184271 A1 | 11/2014 | |
| WO | WO 2014/188377 A2 | 11/2014 | |
| WO | WO 2015/181275 A1 | 12/2015 | |
| WO | WO 2015/183794 A1 | 12/2015 | |
| WO | WO-2015183794 A1 * | 12/2015 | ............... A61K 31/155 |
| WO | 2016/079517 A1 | 5/2016 | |
| WO | WO 2016/073767 A1 | 5/2016 | |
| WO | WO 2016/079518 A1 | 5/2016 | |
| WO | WO 2016/079519 A1 | 5/2016 | |
| WO | WO 2016/079520 A1 | 5/2016 | |
| WO | WO 2016/086115 A1 | 6/2016 | |
| WO | WO 2016/086134 A1 | 6/2016 | |
| WO | WO 2016/086169 A1 | 6/2016 | |
| WO | WO 2016/086218 A1 | 6/2016 | |
| WO | WO 2016/205475 A2 | 12/2016 | |
| WO | WO 2017/199036 A1 | 11/2017 | |
| WO | WO 2017/199039 A1 | 11/2017 | |

OTHER PUBLICATIONS

Zaragoza Dorwald, Side Reactions in Organic Synthesis, 2005, WILEY-VCH Verlag GmbH & Co. KGaA, Weinheim, Preface. p. IX. (Year: 2005).*
Akhrem, Total Synthesis of Steroids, 1970, Plenum Press, New York, pp. vii-362 (Year: 1970).
Bortolini, et al., "Improved Enantioselectivity in the Epoxidation of Cinnamic Acid Derivatives with Dioxiranes from Keto Bile Acids", J. Org. Chem, 2002, 67(16), pp. 5802-5806.
Brown, et al., "The antimicrobial natural product chuangxinmycin and Some synthetic analogues are potent and selective inhibitors of bacterial tryptophanyl tRNA synthetase", Bioorganic & Medicinal Chemistry Letters, 2002, 12, 21, pp. 3171-3174.
Carnell, et al., "Design, Synthesis, and In Vitro Testing of α-Methylacyl-CoA Racemase Inhibitors", J. Med. Chem., 2007, 50(11), pp. 2700-2707.
Classon, et al., "New halogenation reagent systems useful for the mild one-step conversion of alcohols into iodides or bromides", J. Org. Chem, 1988, (53)26, pp. 6126-6130.
D'Amore, et al. "Design, Synthesis, and Biological Evaluation of Potent Dual Agonists of Nuclear and Membrane Bile Acid Receptors" J. Med. Chem. 2014, 57(3), pp. 937-954.
Dauben, et al., "Stereocontrolled Synthesis of Steroidal Side Chains", J. Am. Chem. Soc., 1981, 103(1), pp. 237-238.
De, et al. "Regio- and stereoselective monoepoxidation of dienes using methyltrioxorhenium: synthesis of allylic epoxides" The Journal of Organic Chemistry, vol. 79, No. 21, 2014, pp. 10323-10333.
Dorwald, Side Reactions in Organic Synthesis, WILEY-VCH Verlag GmbH & Co. KGaA, Weinheim, Preface. 2005, p. IX.
Edelsz Ilin, et al., "Synthesis of C—C bonded dimeric steroids by olefin metathesis" Tetrahedron, 2009, vol. 65, 18, pp. 3615-3623.
Festa, et al., "Exploitation of Cholane Scaffold for the Discovery of Potent and Selective Farnesoid X Receptor (FXR) and G-Protein Coupled Bile Acid Receptor 1 (GP-BAR1) Ligands", J Med. Chem., 2014, 57(20), pp. 8477-8495.
Goldstein, "Synthesis and Bioevaluation of $\Delta^7$-5-Desaturase Inhibitors, an Enzyme Late in the Biosynthesis of the Fungal Sterol Ergosterol", J. Med. Chem, 1996, 39(26), pp. 5092-5099.
Hui, et al., A Short and Highly Stereoselective Synthesis of Squalamine from Methyl Chenodeoxycholanate, Chin. J. Chem., 2005, 23(2), pp. 176-181.
Jonker, et al., "FXR and PXR: Potential therapeutic targets in cholestasis", J. Steroid Biochem., Mol. Biol., 2012, 130, pp. 147-158.
Jourdan, et al. "Effects of C-17 heterocyclic substituents on the anticancer activity of 2-ethylestra-1,3,5(10)-triene-3-O-sulfamates: synthesis, in vitro evaluation and computational modelling", Org. Biomol. Chem., 2008, 6, pp. 4108-4119.
Kim, et al., "Efficient and selective cleavage of acetals and ketals using ferric chloride adsorbed on silica gel" J. Org. Chem. 1986, 51, 3, pp. 404-407.
Leppik R.A., "Improved synthesis of 3-keto, 4-ene-3-keto, and 4,6-diene-3-keto bile acids," Steroids, 1983, 41(4), pp. 475-484.
Marker, et al., "Sterols. CII. Chlorogenin", J. Am. Chem. Soc., 1940, 62(9), pp. 2537-2540.
Paulekuhn, et al., "Trends in Active Pharmaceutical Ingredient Salt Selection based on Analysis of the Orange Book Database", J. Med. Chem, 2007, 50(26), pp. 6665-6672.
Pellicari, et al., "Novel stereoselective synthesis and chromatographic evaluation of E-guggulsterone", Steroids, 2012, 77(3), pp. 250-254.
Schteingart, et al., "Synthesis of 24-nor-5β-cholan-23-oic acid derivatives: a convenient and efficient one-carbon degradation of the side chain of natural bile acids", Journal of Lipid Research, 1988, vol. 29, pp. 1387-1395.
Sepe, et al., "The First Total Synthesis of Solomonsterol B, a Marine Pregnane X Receptor Agonist", Eur. J. Org. Chem. 2012, pp. 5187-5194.
Shepherd, et al., "A Synthesis of Progesterone from Ergosterol", J. Am Chem. Soc., 1955, 77(5), pp. 1212-1215.
Shingate, et al., "A Concise Account of Various Approaches for Stereoselective Construction of the C—20(H) Stereogenic Center in Steroid Side Chain" Chem. Rev. 2014, 114(12), pp. 6349-6382.
Stocks, et al., on Medicinal Chemistry, Sci-Ink Limited 2007, ISBN 978-0-9550072-3-1, pp. 216.
Tochtrop, et al. "Synthesis of [3,4-$^{13}C_2$]-Enriched Bile Salts as NMR Probes of Protein-Ligand Interactions" The Journal of Organic Chemistry, vol. 67, No. 19, 2002, pp. 6764-6771.
Trost, et al., "Enol thioethers as enol substitutes. An alkylation sequence", J. Am Chem. Soc., 1983, 105(15), pp. 5075-5090.
Usui, et al., "Metabolic studies of bile acids. XLV[1]. The transformation of 3β,-7α-dihydroxychol-5-enic-24-$^{14}$C acid to

(56) References Cited

OTHER PUBLICATIONS chenodeoxycholic acid in the rat. The significance of the C-7α-hydroxyl group in bile acid formation," Steroids, 1964, (3)2, pp. 147-161.
Verlade, et al., "Steroids. CXIII. 6-Methyl Estrogens," J. Org. Chem., 1959, 24(3) pp. 311-313.
Wang, et al., "Targeting enterohepatic bile acid signaling as a novel approach to modulate hepatic autophagic activity in maintaining cholesterol homeostasis." Hepatology (Oct. 2015), 62 (S1), 280A.
Wikipedia, Steroid, recovered on Oct. 24, 2018 from https://en.wikipedia.org/wiki/Steroid#Species_distribution_and_function, pp. 1-14 (Year: 2018).
Zeng, et al., "Neurosteroid Analogues. 10. The Effect of Methyl Group Substitution at the C-6 and C-7 Positions on the GABA Modulatory and Anesthetic Actions of (3α,5α)- and (3α,5β)-3-Hydroxypregnan-20-one", J. M. Chem., 2005, 48(8), pp. 3051-3059.
Zhou, et al., "A stereoselective synthesis of squalamine", Tetrahedron, 2002, 58, pp. 10293-10299.
International Search Report issued in corresponding International Patent Application No. PCT/GB2017/051385 dated Sep. 17, 2017.
Gioiello et al., "Extending SAR of bile acids as FXR ligands: Discovery of 23-N-(carbocinnamyloxy)-3alpha,7alpha-dihydroxy-6alpha-ethyl-24-nor-5beta-cholan-23-amine," Bioorganic & Medicinal Chemistry, 19: 2650-2658 (2011).
Uekawa et al., "Short-step Synthesis of Chenodiol from Stigmasterol," Bioscience, Biotechnology, and Biochemistry, 68: 1332-1337 (2004).
Written Opinion issued in corresponding International Patent Application No. PCT/GB2017/051385 dated Sep. 17, 2017.

* cited by examiner

INTERMEDIATES FOR THE SYNTHESIS OF BILE ACID DERIVATIVES, IN PARTICULAR OF OBETICHOLIC ACID

CROSS-REFERENCE TO RELATED APPLICATIONS

This application claims the benefit of International Application No. PCT/GB2017/051385, filed May 18, 2017, which claims the benefit of GB Patent Application No. 1608777.7 filed May 18, 2016, the entire contents of which are hereby incorporated by reference herein in their entireties.

The present invention relates to compounds which are intermediates in the synthesis of bile acid derivatives with pharmacological activity. In particular, the invention relates to intermediates in the synthesis of obeticholic acid and its analogues. In addition, the invention relates to a method of synthesizing these intermediates and a method of preparing obeticholic acid and obeticholic acid analogues from the compounds of the invention.

Bile acids are steroid acids which are found in the bile of mammals and include compounds such as cholic acid, chenodeoxycholic acid, lithocholic acid and deoxycholic acid, all of which are found in humans. Many bile acids are natural ligands of the farnesoid X receptor (FXR) which is expressed in the liver and intestine of mammals, including humans.

Bile acids are derivatives of steroids and are numbered in the same way. The following shows the general numbering system for steroids and the numbering of the carbon atoms in chenodeoxycholic acid.

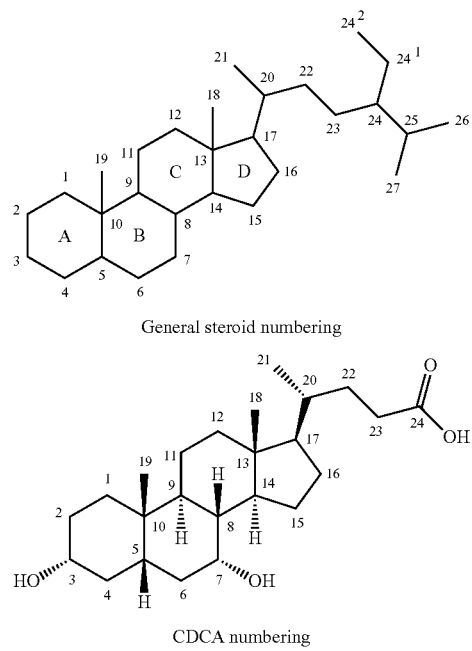

General steroid numbering

CDCA numbering

Agonists of FXR have been found to be of use in the treatment of cholestatic liver disorders including primary biliary cirrhosis and non-alcoholic steatohepatitis (see review by Jonker et al, in *Journal of Steroid Biochemistry & Molecular Biology*, 2012, 130, 147-158).

Ursodeoxycholic acid (UDCA), a bile acid originally isolated from the gall bladder of bears, is currently used in the treatment of cholestatic liver disorders, although it appears to be inactive at the FXR.

As well as their action at the FXR, bile acids and their derivatives are also modulators of the G protein-coupled receptor TGR5. This is a member of the rhodopsin-like superfamily of G-protein coupled receptors and has an important role in the bile acid signalling network, which complements the role of the FXR.

Because of the importance of FXR and TGR5 agonists in the treatment of cholestatic liver disorders, efforts have been made to develop new compounds which have agonist activity at these receptors. One particularly active compound is obeticholic acid, which is a potent agonist of both FXR and TGR5. Obeticholic acid is described in WO 02/072598 and EP1568706, both of which describe a process for the preparation of obeticholic acid from 7-keto lithocholic acid, which is derived from cholic acid. Further processes for the production of obeticholic acid and its derivatives are described in WO 2006/122977, US 2009/0062256 and WO 2013/192097 and all of these processes also start from 7-keto lithocholic acid.

It is clear from the number of patent publications directed to processes for the production of obeticholic acid that it is by no means simple to synthesise this compound and indeed the process which is currently used starts from cholic acid, has 12 steps and a low overall yield.

In addition to the inefficiency and high cost of this process, there are also problems with the cost and availability of the starting materials. Cholic acid, the current starting material for the production of obeticholic acid, is a natural bile acid which is usually obtained from the slaughter of cows and other animals. This means that the availability of cholic acid and other bile acids is limited by the number of cattle available for slaughter. Since the incidence of cholestatic liver disease is increasing worldwide, the demand for synthetic bile acids such as obeticholic acid is also likely to increase and it is doubtful whether the supply of naturally derived bile acids will continue to be sufficient to meet demand.

Furthermore, the use of a starting material derived from animals means that there is the possibility of the contamination of the material with infectious agents such as viruses or prions, which can not only be hazardous to workers but could potentially contaminate the end products if steps are not taken to prevent this.

Although some patients with cholestatic liver disease can be treated with ursodeoxycholic acid, this is also a natural bile acid and faces the same problems of limited availability and high cost.

In an attempt to solve the problems associated with the use of bile acids as starting materials, the present inventors have devised a process for the synthesis of synthetic bile acid derivatives, such as obeticholic acid, which uses plant sterols as starting materials.

The inventors have developed a process for the production of synthetic bile acids which proceeds via novel intermediates and which provides the final product in significantly higher yield than current processes. The process is flexible and can use a variety of different starting materials including animal, fungal and plant sterols.

Suitable animal sterols which can be used as starting materials include deoxycholic acid, cholic acid, while fungal sterols include ergosterol.

Plant sterols are widely available at significantly lower cost than bile acids and, indeed, are often waste products of other processes. Suitable plant sterol and plant sterol derivatives which can be used as starting materials include 3-ketobis-norcholenol (also known as 20-hydroxymethylpregn-4-en-3-one), androstenedione, androstadienedione, dehydroepiandrosterone, stigmasterol, brassicasterol, campesterol and R-sitosterol.

Our patent applications Nos. PCT/GB2015/053516 (WO2016/079517), PCT/GB2015/053517 (WO2016/079518), PCT/GB2015/053518 (WO2016/079519) and PCT/GB2015/053519 (WO2016/079520) relate to intermediates in the process as well as to processes for preparing the intermediates and processes for converting them to the desired products. The present application relates to further compounds which are analogues of the compounds described in WO2016/079517, WO2016/079518, WO2016/079519 and WO2016/079520.

In the present invention there is provided a compound of general formula (I):

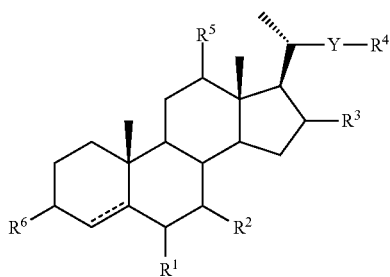

(I)

wherein:

⌇ is a carbon-carbon single or double bond;

$R^1$ is $C_{1-4}$ alkyl optionally substituted with one or more substituents selected from halo, $OR^{7a}$ and $NR^{7a}R^{7b}$;
  where each of $R^{7a}$ and $R^{7b}$ is independently selected from H and $C_{1-4}$ alkyl; or $R^1$ and $R^2$ together form an epoxide group;

$R^2$ is =O or OH or a protected OH or $R^2$ and $R^1$ together form an epoxide group;

$R^3$ is H, halo or OH or a protected OH;

when ⌇ is a carbon-carbon double bond, Y is a bond or an alkylene, alkenylene or alkynylene linker group having from 1 to 20 carbon atoms and optionally substituted with one or more groups $R^{13}$;

when ⌇ is a carbon-carbon single bond, Y is a bond or an alkylene linker group having from 1 to 20 carbon atoms and optionally substituted with one or more groups $R^{13}$;

each $R^{13}$ is independently halo, $OR^8$ or $NR^8R^9$;
  where each of $R^8$ and $R^9$ is independently selected from H and $C_{1-4}$ alkyl;

$R^4$ is halo, CN, $C(O)R^{10}$, $CH(OR^{10})(OR^{11})$, $CH(R^{10})(OR^{11})$, $CH(SR^{10})(SR^{11})$, $NR^{10}R^{11}$, $BR^{10}R^{11}$, $C(O)CH_2N_2$, —CH=CH$_2$, —C≡CH, $CH[C(O)OR^{10}]_2$, $CH(BR^{10}R^{11})_2$, azide or a carboxylic acid mimetic group;
  where each $R^{10}$ and $R^{11}$ is independently:
  a. hydrogen or
  b. $C_{1-20}$ alkyl, $C_{2-20}$ alkenyl or $C_{2-20}$ alkynyl, any of which is optionally substituted with one or more substituents selected from halo, $NO_2$, CN, $OR^{19}$, $SR^{19}$, $C(O)R^{19}$, $C(O)N(R^{19})_2$, $SO_2R^{19}$, $SO_3R^{19}$, $OSO_3R^{19}$, $N(R^{19})_2$ and a 6- to 14-membered aryl or 5 to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$ and $N(R^{19})_2$;
  or
  c. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$ and $N(R^{19})_2$;
  or
  d. a polyethylene glycol residue; or
  e. when $R^4$ is $CH(OR^{10})(OR^{11})$, $CH(R^{10})(OR^{11})$, $CH(SR^{10})(SR^{11})$, $NR^{10}R^{11}$, $BR^{10}R^{11}$, $CH[C(O)OR^{10}]_2$ or $CH(BR^{10}R^{11})_2$ an $R^{10}$ and an $R^{11}$ group, together with the atom or atoms to which they are attached, may combine to form a 3 to 10-membered heterocyclic ring;
  each $R^{19}$ is independently selected from H, $C_{1-6}$ alkyl, $C_{1-6}$ haloalkyl and a 6- to 14-membered aryl or 5 to 14-membered heteroaryl group either of which is optionally substituted with one or more substituents selected from halo, $C_{1-6}$ alkyl and $C_{1-6}$ haloalkyl; or
Y and $R^4$ together form a =CH$_2$ group;

$R^5$ is H or OH or a protected OH group;

$R^6$ is =O;

or a salt or an isotopic variant thereof.

Compounds of general formula (I) are intermediates in the synthesis of pharmaceutically active compounds such as obeticholic acid and its derivatives.

In the present specification, except where the context requires otherwise due to express language or necessary implication, the word "comprises", or variations such as "comprises" or "comprising" is used in an inclusive sense i.e. to specify the presence of the stated features but not to preclude the presence or addition of further features in various embodiments of the invention.

All publications, including but not limited to patents and patent applications, cited in this specification are herein incorporated by reference as if each individual publication were specifically and individually indicated to be incorporated by reference herein as though fully set forth.

In the present application the term "$C_{1-20}$" alkyl refers to a straight or branched fully saturated hydrocarbon group having from 1 to 20 carbon atoms. The term encompasses methyl, ethyl, n-propyl, isopropyl, n-butyl, isobutyl, s-butyl and t-butyl. Other alkyl groups, for example $C_{1-12}$ alkyl, $C_{1-10}$ alkyl, $C_{1-6}$ alkyl or $C_{1-3}$ alkyl are as defined above but contain different numbers of carbon atoms.

The terms "heterocyclic" and "heterocyclyl" refer to a non-aromatic cyclic group having 3 to 10 ring atoms and at least one heteroatom selected from N, O, S and B and optionally substituted with one or more =O moieties. Examples of heterocyclic groups include pyrrolidine, piperidine, morpholine, piperazine, tetrahydrofuran, dioxolane (e.g. 1,3-dioxolane), dioxane (e.g. 1,3-dioxane) and cyclic thioethers. The term also includes bicyclic and bridged groups such as 9-borabicyclo(3.3.1)nonane (9-BBN).

The term "halogen" refers to fluorine, chlorine, bromine or iodine and the term "halo" to fluoro, chloro, bromo or iodo groups.

The term "$C_{1-6}$ haloalkyl" refers to a straight or branched alkyl group as defined above having from 1 to 6 carbon atoms and substituted with one or more halo atoms, up to perhalo substitution. Examples include trifluoromethyl, chloroethyl and 1,1-difluoroethyl.

The term "$C_{2-20}$ alkenyl" refers to a straight or branched hydrocarbon group having from 2 to 20 carbon atoms and at least one carbon-carbon double bond. Examples include ethenyl, prop-1-enyl, hex-2-enyl etc. Other alkenyl groups, for example $C_{2-12}$ alkenyl, $C_{2-10}$ alkenyl, $C_{2-8}$ alkenyl, $C_{2-6}$ alkenyl, $C_{2-5}$ alkenyl, $C_{2-4}$ alkenyl or $C_{2-3}$ alkenyl are as defined above but contain different numbers of carbon atoms.

The term "$C_{2-20}$ alkynyl" refers to a straight or branched hydrocarbon group having from 2 to 20 carbon atoms and at least one carbon-carbon triple bond. Examples include ethynyl, prop-1-ynyl, hex-2-ynyl etc. Other alkynyl groups, for example $C_{2-12}$ alkynyl, $C_{2-10}$ alkynyl, $C_{2-8}$ alkynyl, $C_{2-6}$ alkynyl, $C_{2-5}$ alkynyl, $C_{2-4}$ alkynyl or $C_{2-3}$ alkynyl are as defined above but contain different numbers of carbon atoms.

The term "alkylene" refers to a straight or branched fully saturated hydrocarbon chain. Suitably alkylene is $C_{1-20}$ alkylene, $C_{1-12}$ alkylene, $C_{1-10}$ alkylene, $C_{1-8}$ alkylene, $C_{1-6}$ alkylene, $C_{1-5}$ alkylene, $C_{1-4}$ alkylene, $C_{1-3}$ alkylene, or $C_{1-2}$ alkylene. Examples of alkylene groups include —$CH_2$—, —$CH_2CH_2$—, —$CH(CH_3)$—$CH_2$—, —$CH_2CH(CH_3)$— —$CH_2CH_2CH_2$—, —$CH_2CH(CH_2CH_3)$— and —$CH_2CH(CH_2CH_3)CH_2$—.

The term "alkenylene" refers to a straight or branched hydrocarbon chain containing at least one carbon-carbon double bond. Suitably alkenylene is $C_{2-20}$ alkenylene, $C_{2-12}$ alkenylene, $C_{2-10}$ alkenylene, $C_{2-8}$ alkenylene, $C_{2-6}$ alkenylene, $C_{2-5}$ alkenylene, $C_{2-4}$ alkenylene, or $C_{2-3}$ alkenylene. Examples of alkenylene groups include —CH=CH—, —CH=C($CH_3$)—, —$CH_2$CH=CH—, —CH=CHCH$_2$—, —$CH_2CH_2$CH=CH—, —$CH_2$CH=C($CH_3$)— and —$CH_2$CH=C($CH_2CH_3$)—.

The term "alkynylene" refers to a straight or branched hydrocarbon chain containing at least one carbon-carbon triple bond. Suitably alkynylene is $C_{2-20}$ alkynylene, $C_{2-12}$ alkynylene, $C_{2-10}$ alkynylene, $C_{2-8}$ alkynylene, $C_{2-6}$ alkynylene, $C_{2-5}$ alkynylene, $C_{2-4}$ alkynylene, or $C_{2-3}$ alkynylene. Examples of alkynylene groups include —C≡C—, —$CH_2$C≡C—, —C≡C—$CH_2$—, —$CH_2CH_2$C≡C—, —$CH_2$C≡CCH$_2$— and —$CH_2$C—C≡C$CH_2CH_2$—.

The terms "aryl" and "aromatic" refer to a cyclic group with aromatic character having from 6 to 14 ring carbon atoms (unless otherwise specified) and containing up to three rings. Where an aryl group contains more than one ring, not all rings must be aromatic in character. Examples include phenyl, naphthyl and anthracenyl as well as partially saturated systems such as tetrahydronaphthyl, indanyl and indenyl.

The terms "heteroaryl" and "heteroaromatic" refer to a cyclic group with aromatic character having from 5 to 14 ring atoms (unless otherwise specified), at least one of which is a heteroatom selected from N, O and S, and containing up to three rings. Where a heteroaryl group contains more than one ring, not all rings must be aromatic in character. Examples of heteroaryl groups include pyridine, pyrimidine, indole, benzofuran, benzimidazole and indolene.

The term "isotopic variant" refers to isotopically-labelled compounds which are identical to those recited in formula (I) but for the fact that one or more atoms are replaced by an atom having an atomic mass or mass number different from the atomic mass or mass number most commonly found in nature, or in which the proportion of an atom having an atomic mass or mass number found less commonly in nature has been increased (the latter concept being referred to as "isotopic enrichment"). Examples of isotopes that can be incorporated into compounds of the invention include isotopes of hydrogen, carbon, nitrogen, oxygen, fluorine, iodine and chlorine such as $^2H$ (deuterium), $^3H$, $^{11}C$, $^{13}C$, $^{14}C$, $^{18}F$, $^{123}I$ or $^{125}I$, which may be naturally occurring or non-naturally occurring isotopes.

Polyethylene glycol (PEG) is a polyether compound, which in linear form has general formula H—[O—$CH_2$—$CH_2$]$_n$—OH. A polyethylene glycol residue is a PEG in which the terminal H is replaced by a bond linking it to the remainder of the molecule. Branched versions, including hyperbranched and dendritic versions are also contemplated and are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly (ethylene glycol) can be represented in general form as R(-PEG-OH)$_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; US 2003/0143596; WO 96/21469; and WO 93/21259 may also be used.

The PEG polymers may have an average molecular weight of, for example, 600-2,000,000 Da, 60,000-2,000,000 Da, 40,000-2,000,000 Da, 400,000-1,600,000 Da, 800-1,200,000 Da, 600-40,000 Da, 600-20,000 Da, 4,000-16,000 Da, or 8,000-12,000 Da.

The term "protected OH" relates to an OH group protected with any suitable protecting group.

Suitable protecting groups include esters such that, for example when $R^2$ and/or $R^3$ and/or $R^5$ is a protected OH group, $R^2$ and/or $R^3$ and/or $R^5$ and/or $R^6$ may independently be a group OC(O)$R^{14}$, where $R^{14}$ is a group $R^{10}$ as defined above.

Silyl ethers are also suitable, and in this case, $R^2$ and/or $R^3$ and/or $R^5$ may independently be a group OSi($R^{16}$)$_3$, where each $R^{16}$ is independently:

a. $C_{1-20}$ alkyl, $C_{2-20}$ alkenyl or $C_{2-20}$ alkynyl optionally substituted with one or more substituents selected from halo, $NO_2$, CN, $OR^{19}$, $SR^{19}$, $SO_2R^{19}$, $SO_3R^{19}$ or $N(R^{19})_2$, a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SO_2R^{19}$, $SO_3R^{19}$ or $N(R^{19})_2$; or b. a 6- to 14-membered aryl or 5 to 14-membered heteroaryl group optionally substituted with one or more substituents selected from $C_{1-6}$ alkyl, $C_{1-6}$ haloalkyl, halo, $NO_2$, CN, $OR^{19}$, $SR^{19}$, $SO_2R^{19}$, $SO_3R^{19}$ or $N(R^{19})_2$;

each $R^{19}$ is independently selected from H, $C_{1-6}$ alkyl or $C_{1-6}$ haloalkyl.

Silyl ethers are particularly suitable for the protection of OH at the $R^2$ position (J. Med. Chem., 2014, 57, 937-954). In this case, it is particularly suitable for each $R^{16}$ to be independently $C_{1-6}$ alkyl. An example of a silyl protected OH group $R^2$ is t-butyldimethylsilyloxy.

Other suitable protecting groups for OH are well known to those of skill in the art (see Wuts, P G M and Greene, T W (2006) "Greene's Protective Groups in Organic Synthesis", 4$^{th}$ Edition, John Wiley & Sons, Inc., Hoboken, N.J., USA).

References to a protecting group which is stable in basic conditions mean that the protecting group cannot be removed by treatment with a base.

Appropriate salts of the compounds of general formula (I) include basic addition salts such as sodium, potassium, calcium, aluminium, zinc, magnesium and other metal salts as well as choline, diethanolamine, ethanolamine, ethyl diamine, meglumine and other well-known basic addition salts as summarised in Paulekuhn et al., *J. Med. Chem.* 2007, 50, 6665-6672 and/or known to those skilled in the art.

The term "carboxylic acid mimetic group" relates to known carboxylic acid isosteres including tetrazole, —$SO_2$—$NHR^{30}$, $C(O)NH$—$SO_2R^{30}$, $NHC(O)NH$—$SO_2R^{30}$;

wherein $R^{30}$ is H, $C_{1-6}$ alkyl $C_{3-7}$ cycloalkyl or aryl (e.g. phenyl) optionally substituted, for example with $C_{1-4}$ alkyl, halo, OH, O($C_{1-4}$ alkyl), $SO_2$($C_{1-4}$ alkyl), $SO_2$-phenyl or $SO_2$-tolyl. Tetrazole groups include tetrazole-5-yl and tetrazole-1-yl and are optionally substituted, for example with $C_{1-4}$ alkyl, halo, OH, O($C_{1-4}$ alkyl), $SO_2$($C_{1-4}$ alkyl), $SO_2$-phenyl or $SO_2$-tolyl.

Such carboxylic acid mimetic groups are well known in the art and are discussed, for example in "On Medicinal Chemistry"; M Stocks, L Alcaraz, E Griffen; Pub: Sci-ink Ltd (April 2007).

Particularly suitable carboxylic acid mimetic groups include tetrazole, C(O)NH—$SO_2R^{30}$ and NHC(O)NH—$SO_2R^{30}$, with tetrazole being particularly suitable.

In some cases, the compound of general formula (I) is a compound of general formula (IA):

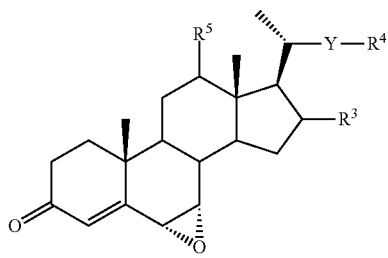

(IA)

wherein $R^3$, Y, $R^4$ and $R^5$ are as defined for general formula (I).

In other cases, the compound of general formula (I) is a compound of general formula (IB):

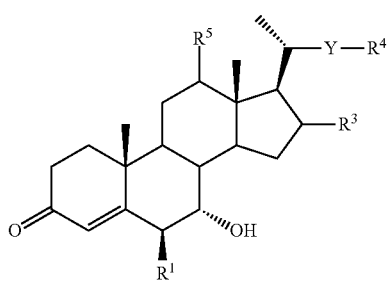

(IB)

wherein $R^1$, $R^3$, Y, $R^4$ and $R^5$ are as defined for general formula (I).

Alternatively, the compound of general formula (I) may be a compound of general formula (IC):

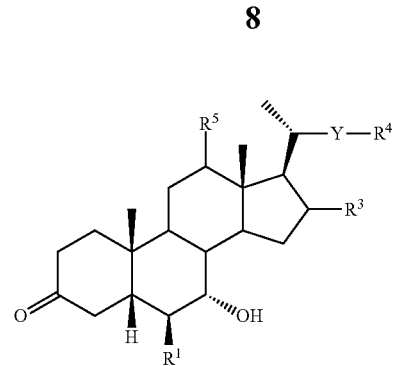

(IC)

wherein $R^1$, $R^3$, Y, $R^4$ and $R^5$ are as defined for general formula (I).

The compound of general formula (I) may be a compound of general formula (ID):

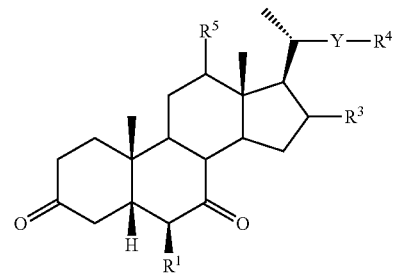

(ID)

wherein $R^1$, $R^3$, Y, $R^4$ and $R^5$ are as defined for general formula (I).

The compound of general formula (I) may also be a compound of general formula (IE):

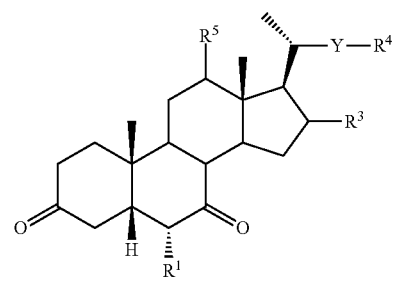

(IE)

wherein $R^1$, $R^3$, Y, $R^4$ and $R^5$ are as defined for general formula (I).

Compounds of general formula (I) may be converted to compounds of general formula (IF):

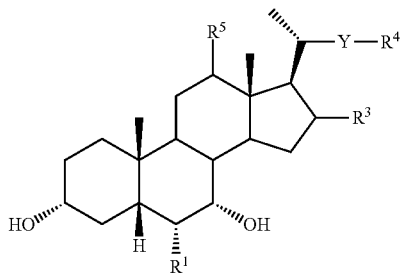

(IF)

wherein $R^1$, $R^3$, Y, $R^4$ and $R^5$ are as defined for general formula (I).

Compounds of general formula (IF) are analogues of obeticholic acid in which the side chain has a substituent $R^4$ as defined above.

In some suitable compounds of general formulae (I), (IB), (IC), (ID) and (IE):
$R^1$ is $C_{1-4}$ alkyl optionally substituted with one or more substituents selected from halo, $OR^{7a}$ or $NR^{7a}R^{7b}$;
where each of $R^{7a}$ and $R^{7b}$ is independently selected from H or $C_{1-4}$ alkyl.

In more suitable compounds of general formulae (I), (IB), (IC), (ID) and (IE), $R^1$ may be $C_{1-4}$ alkyl optionally substituted with one or more substituents selected from halo, $OR^{7a}$ or $NR^{7a}R^{7b}$, where $R^{7a}$ and $R^{7b}$ are each independently H, methyl or ethyl, especially H or methyl.

More suitably, $R^1$ is unsubstituted $C_{1-4}$ alkyl.

In particularly suitable compounds, $R^1$ is ethyl.

In some compounds of general formulae (I), (IA), (IB), (IC), (ID) or (IE), Y is a bond.

In some compounds of general formulae (I), (IA), (IB), (IC), (ID) or (IE), Y and $R^4$ together form a $=CH_2$ group.

In other compounds of general formula (I), particularly compounds of formula (IA) and (IB), Y is an alkylene or alkenylene linker group having from 1 to 15 carbon atoms, more suitably 1 to 12, 1 to 10 or 1 to 8 carbon atoms and optionally substituted with one or more groups $R^{13}$ as defined above. Typically, each $R^{13}$ is independently halo, $OR^8$ or $NR^8R^9$; where each of $R^8$ and $R^9$ is independently selected from H, methyl or ethyl, especially H or methyl.

In some more suitable compounds of general formula (I), particularly compounds of formulae (IA) and (IB), Y is a bond or an unsubstituted alkylene or alkenylene linker having from 1 to 15 carbon atoms, more suitably 1 to 12, 1 to 10 or 1 to 8 carbon atoms.

In other more suitable compounds of general formula (I), particularly compounds of formulae (IA) and (IB), Y is a bond, an unsubstituted $C_{1-3}$ alkylene group, a $C_{1-3}$ alkylene group substituted with OH, or a $C_{1-3}$ alkenylene group. For example, Y may be a bond, $-CH_2-$, $-CH_2-CH_2-$, $-CH(OH)-CH_2-$, $-CH=CH-$ or $-CH=C(CH_3)-$, especially $-CH_2-$, $-CH_2-CH_2-$, $-CH=CH-$ or $-CH=C(CH_3)-$.

In other suitable compounds of general formula (I), particularly compounds of general formulae (IC), (ID) and (IE), Y is an alkylene linker group having from 1 to 15 carbon atoms, more suitably 1 to 12, 1 to 10 or 1 to 8 carbon atoms and optionally substituted with one or more groups $R^{13}$ as defined above. Typically, each $R^{13}$ is independently halo, $OR^8$ or $NR^8R^9$; where each of $R^8$ and $R^9$ is independently selected from H, methyl or ethyl, especially H or methyl.

In some more suitable compounds of general formula (I), particularly compounds of general formulae (IC), (ID) and (IE), Y is a bond or an unsubstituted alkylene linker having from 1 to 15 carbon atoms, more suitably 1 to 12, 1 to 10 or 1 to 8 carbon atoms.

In other more suitable compounds of general formula (I), particularly compounds of formulae (IC), (ID) and (IE), Y is a bond or an alkylene group having 1 to 3 carbon atoms and is optionally substituted with one or two $R^{13}$ groups, wherein $R^{13}$ is suitably OH, for example Y is a bond, $-CH_2-$, $-CH_2-CH_2-$ or $-CH(OH)-CH_2-$, especially $-CH_2-$, or $-CH_2-CH_2-$.

In some suitable compounds of general formula (I), Y is an alkylene linker having from 1 to 15 carbon atoms, more suitably 1 to 12, 1 to 10 or 1 to 8 carbon atoms and substituted with an OH group. In this case, the OH group may be separated from the $R^4$ moiety by a single $CH_2$ group such that the linker Y is a group $Y^4-CH(OH)-CH_2-$, where $Y^4$ is as defined for Y, but is shorter by two carbon atoms. For example, Y may be $-CH(OH)-CH_2-$.

This Y linker is particularly suitable when $R^4$ is CN or $R^4$ is $CH(OR^{10})(OR^{11})$ wherein $R^{10}$ and $R^{11}$ are as defined above, but particularly wherein the $OR^{10}$ and $OR^{11}$ groups together with the carbon atom to which they are attached form a cyclic acetal group, e.g. a 1,3-dioxane or 1,3-dioxolane ring.

In some suitable compounds of general formula (I), $R^3$ is H.

In other suitable compounds of general formula (I), $R^3$ is OH.

In still other suitable compounds of general formula (I), $R^3$ is a protected OH group. When $R^3$ is a protected OH group, it may be a group which is not stable in a basic environment such that treatment with a base converts the protected OH group to OH. Examples of such groups are well known in the art and include a group $OC(O)R^{14}$ as defined above in which $R^{14}$ is a group $R^{10}$ as defined above for general formula (I).

In the compounds of general formula (I), when $R^3$ is other than hydrogen, it is suitably in the "up" position, i.e. in the beta configuration.

Particularly suitable $R^{14}$ groups are as defined below for $R^{10}$.

Alternatively, $R^3$ may be a protected OH group which is stable in a basic environment. Examples of such groups include $OSi(R^{16})_3$, where each $R^{16}$ is independently:

a. $C_{1-20}$ alkyl, $C_{2-20}$ alkenyl or $C_{2-20}$ alkynyl optionally substituted with one or more substituents selected from halo, $NO_2$, CN, $OR^{19}$, $SR^{19}$, $C(O)OR^{19}$, $C(O)N(R^{19})_2$, $SO_2R^{19}$, $SO_3R^{19}$ or $N(R^{19})_2$, or a 6- to 14-membered aryl or 5 to 14-membered heteroaryl group, either of which is optionally substituted with $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ or $N(R^{19})_2$; or b. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$ or $N(R^{19})_2$;

each $R^{19}$ is independently selected from H, $C_{1-6}$ alkyl or $C_{1-6}$ haloalkyl.

Suitably each $R^{16}$ is independently selected from:

a. $C_{1-10}$ alkyl, $C_{2-10}$ alkenyl or $C_{2-10}$ alkynyl optionally substituted with one or more substituents as described above; or b. a 6- to 10-membered aryl or 5 to 10-membered heteroaryl group optionally substituted with one or more substituents as described above.

More suitably, each $R^{16}$ is independently selected from:
  a. $C_{1-10}$ alkyl, $C_{2-10}$ alkenyl or $C_{2-10}$ alkynyl optionally substituted with one or more substituents as described above; or
  b. a 6- to 10-membered aryl group optionally substituted with one or more substituents as described above.

Still more suitably, each $R^{16}$ is independently selected from $C_{1-10}$ alkyl or phenyl, either of which is optionally substituted as described above. Examples of $OSi(R^{16})_3$ include trimethylsilyl (TMS), triethylsilyl (TES), triphenylsilyl (TPS), tri-isopropylsilyl (TIPS), dimethylhexylsilyl (TDS), tert-butyldiphenylsilyl (TBDPS), tert-butyldimethylsilyl (TBDMS or TBS), di-tert-butylmethylsilyl (DTBMS), diethylisopropylsilyl (DEIPS) and dimethylisopropylsilyl (DMIPS), in particular TMS, TES, TIPS, TBDMS and TBDPS.

In the compounds of general formulae (I), (IA), (IB), (IC), (ID) and (IE), $R^4$ is halo, CN, $C(O)R^{10}$, $CH(OR^{10})(OR^{11})$, $CH(R^{10})(OR^{11})$, $CH(SR^{10})(SR^{11})$, $NR^{10}R^{11}$, $BR^{10}R^{11}$, $C(O)CH_2N_2$, —CH=CH$_2$, —C≡CH, $CH[C(O)OR^{10}]_2$ or $CH(BR^{10}R^{11})_2$, azide or a carboxylic acid mimetic group such as tetrazole.

When present in the $R^4$ moiety, suitably, each $R^{10}$ and $R^{11}$ is independently:
  a. hydrogen or
  b. $C_{1-10}$ alkyl, $C_{2-10}$ alkenyl or $C_{2-10}$ alkynyl, any of which is optionally substituted with one or more substituents as described above; or
  c. a 6- to 10-membered aryl or 5 to 10-membered heteroaryl group either of which is optionally substituted with one or more substituents as described above; or
  d. a polyethylene glycol residue; or
  e. when $R^4$ is $CH(OR^{10})(OR^{11})$, $CH(R^{10})(OR^{11})$, $CH(SR^{10})(SR^{11})$, $NR^{10}R^{11}$, $BR^{10}R^{11}$, $CH[C(O)OR^{10}]_2$ or $CH(BR^{10}R^{11})_2$ an $R^{10}$ and an $R^{11}$ group, together with the atom or atoms to which they are attached, may combine to form a 3- to 10-membered heterocyclic ring.

More suitably, each $R^{10}$ and $R^{11}$ is independently
  a. hydrogen or
  b. $C_{1-10}$ alkyl, $C_{2-10}$ alkenyl or, $C_{2-10}$ alkynyl optionally substituted with one or more substituents as described above or
  c. a 6- to 10-membered aryl group optionally substituted with one or more substituents as described above; or
  e. when $R^4$ is $NR^{10}R^{11}$, an $R^{10}$ and an $R^{11}$ group, together with the nitrogen to which they are attached, combine to form a pyrrolidine or piperidine ring or when $R^4$ is $CH(OR^{10})(OR^{11})$, the $OR^{10}$ and $OR^{11}$ group, together with the carbon atom to which they are attached, combine to form a cyclic acetal, particularly a 1,3-dioxane or 1,3-dioxolane ring; or when $R^4$ is $BR^{10}R^{11}$, the $R^{10}$ and $R^{11}$ groups, together with the boron atom to which they are attached combine to form a bridged boron-containing ring such as 9-BBN.

Additionally, when $R^4$ is $NR^{10}R^{11}$, $R^{10}$ may be H or $C_{1-4}$ alkyl and $R^{11}$ may be a 5-10 membered heteroaryl group such as tetrazole.

Suitable substituents for alkyl, alkenyl and alkynyl $R^{10}$ and $R^{11}$ groups and alkyl, alkenyl and alkynyl $R^{16}$ groups include halo, $NO_2$, CN, $OR^{19}$, $SR^{19}$, $C(O)OR^{19}$, $SO_2R^{19}$, $SO_3R^{19}$, $OSO_3R^{19}$, $N(R^{19})_2$ and a 6- to 10-membered aryl or 5 to 14-membered heteroaryl group, either of which is optionally substituted with $C_{1-6}$ alkyl, $C_{1-6}$ haloalkyl, halo, $NO_2$, ON, $OR^{19}$, $SO_2R^{19}$, $SO_3R^{19}$ or $N(R^{19})_2$; where $R^{19}$ is as defined above.

More suitable substituents for these $R^{10}$, $R^{11}$ and $R^{16}$ groups include halo, $OR^{19}$, $C(O)OR^{19}$, $N(R^{19})_2$, $SO_3R^{19}$, $OSO_3R^{19}$ and a 6- to 10-membered aryl group optionally substituted as described above, more suitably optionally substituted with halo, $C_{1-4}$ alkyl, $C_{1-4}$ haloalkyl, —O—$C_{1-4}$ alkyl, —O—$C_{1-4}$ haloalkyl, C(O)OH, $SO_2OH$, —NH($C_{1-4}$ alkyl) or —N($C_{1-4}$ alkyl)$_2$; for example fluoro, chloro, methyl, ethyl, trifluoromethyl, methoxy, ethoxy, trifluoromethoxy, C(O)OH, $SO_2OH$, amino, methyl amino or dimethylamino.

Suitable substituents for aryl and heteroaryl $R^{10}$, $R^{11}$ and $R^{16}$ groups include $C_{1-6}$ alkyl, $C_{1-6}$ haloalkyl, halo, $NO_2$, CN, $OR^{19}$, $SR^{19}$ or $N(R^{19})_2$.

More suitable substituents for these $R^{10}$, $R^{11}$ and $R^{16}$ groups include $C_{1-4}$ alkyl, $C_{1-4}$ haloalkyl, halo, $OR^{19}$ or $N(R^{19})_2$; in particular, halo, $C_{1-4}$ alkyl, $C_{1-4}$ haloalkyl, —O—$C_{1-4}$ alkyl, —O—$C_{1-4}$ haloalkyl, —NH($C_{1-4}$ alkyl) or —N($C_{1-4}$ alkyl)$_2$.

Specific examples of substituents for aryl and heteroaryl $R^{10}$, $R^{11}$ and $R^{16}$ groups include fluoro, chloro, methyl, ethyl, trifluoromethyl, methoxy, ethoxy, trifluoromethoxy, amino, methyl amino and dimethylamino.

As set out above, each $R^{19}$ is independently selected from H, $C_{1-6}$ alkyl, $C_{1-6}$ haloalkyl, or a 6- to 14-membered aryl or 5 to 14-membered heteroaryl group either of which is optionally substituted with one or more halo, $C_{1-6}$ alkyl or $C_{1-6}$ haloalkyl substituents.

Suitably, $R^{19}$ is H, $C_{1-6}$ alkyl, $C_{1-6}$ haloalkyl, or a 6- to 10-membered aryl or 5 to 10-membered heteroaryl group optionally substituted with one or more halo, $C_{1-4}$ alkyl or $C_{1-4}$ haloalkyl substituents.

More suitably, $R^{19}$ is H, $C_{1-6}$ alkyl, $C_{1-6}$ haloalkyl or phenyl optionally substituted with one or more halo, $C_{1-4}$ alkyl or $C_{1-4}$ haloalkyl substituents.

Specific examples of $R^{19}$ include H, methyl, ethyl, trifluoromethyl or phenyl optionally substituted with one or more fluoro, chloro, methyl, ethyl or trifluoromethyl groups.

Suitably, $R^4$ is halo, CN, $C(O)R^{10}$, $CH(OR^{10})(OR^{11})$, $NR^{10}R^{11}$, $BR^{10}R^{11}$, —CH=CH$_2$, —C≡CH, $CH[C(O)OR^{10}]_2$, azide, a carboxylic acid mimetic group or $CH(BR^{10}R^{11})_2$ or Y and $R^4$ together form a =CH$_2$ group where $R^{10}$ and $R^{11}$ are as described above.

In other suitable compounds, $R^4$ is halo, CN, $C(O)R^{10}$, $CH(OR^{10})(OR^{11})$, $NR^{10}R^{11}$, $BR^{10}R^{11}$—CH=CH$_2$, —C≡CH, $CH[C(O)OR^{10}]_2$ or $CH(BR^{10}R^{11})_2$ or Y and $R^4$ together form a =CH$_2$ group where $R^{10}$ and $R^{11}$ are as described above.

More suitably, $R^4$ is halo, CN, $C(O)R^{10}$, $CH(OR^{10})(OR^{11})$, CH=CH$_2$, —C≡CH, $CH[C(O)OR^{10}]_2$, $BR^{10}R^{11}$, azide or a carboxylic acid mimetic group or Y and $R^4$ together form a =CH$_2$ group; where $R^{10}$ and $R^{11}$ are as described above.

When $R^4$ is a carboxylic acid mimetic group, it is suitably a tetrazole group. Other suitable carboxylic acid mimetic groups are known in the art and include $C(O)NH$—$SO_2R^{30}$ and $NHC(O)NH$—$SO_2R^{30}$, where $R^{30}$ is as defined above.

In other more suitable compounds, $R^4$ is halo, CN, C(O)$R^{10}$, $CH(OR^{10})(OR^{11})$, CH=CH$_2$, —C≡CH, $CH[C(O)OR^{10}]_2$, $BR^{10}R^{11}$ or Y and $R^4$ together form a =CH$_2$ group; where $R^{10}$ and $R^{11}$ are as described above.

In some particularly suitable compounds, $R^4$ is halo, CN, $C(O)R^{10}$, $CH(OR^{10})(OR^{11})$, $NR^{10}R^{11}$, $CH[C(O)OR^{10}]_2$ or azide;

where $R^{10}$ and $R^{11}$ are as described above but are suitably each independently H or $C_{1-10}$ alkyl, $C_{2-10}$ alkenyl or $C_{2-10}$ alkynyl optionally substituted as described above or, when $R^4$ is $NR^{10}R^{11}$, $R^{11}$ may also suitably be a heteroaryl group such as tetrazole; or when $R^4$ is $CH(OR^{10})(OR^{11})$, the $OR^{10}$ and $OR^{11}$ groups together with the carbon atom to which they are attached may form a cyclic acetal group, particularly a 1,3-dioxane or 1,3-dioxolane group.

In other particularly suitable compounds, $R^4$ is halo, CN, $C(O)R^{10}$, $CH(OR^{10})(OR^{11})$ or $CH[C(O)OR^{10}]_2$;

where $R^{10}$ is H or $C_{1-10}$ alkyl, $C_{2-10}$ alkenyl or $C_{2-10}$ alkynyl optionally substituted as described above or when $R^4$ is $CH(OR^{10})(OR^{11})$, the $OR^{10}$ and $OR^{11}$ groups together with the carbon atom to which they are attached may form a cyclic acetal group, particularly a 1,3-dioxane or 1,3-dioxolane group.

In still other particularly suitable compounds, $R^4$ is a carboxylic acid mimetic group, suitably tetrazole.

In some particularly suitable compounds, $R^4$ is halo, CN, $C(O)R^{10}$, $CH(OR^{10})(OR^{11})$ or $CH[C(O)OR^{10}]_2$; where each $R^{10}$ and $R^{11}$ is independently H or $C_{1-4}$ alkyl or $R^{10}$ and $R^{11}$ together with the carbon and oxygen atoms to which they are attached form a 5- or 6-membered cyclic group.

Examples of $R^4$ groups include Cl, Br, CN, C(O)H, $CH(OR^{10})_2$, 1,3-dioxane, 1,3-dioxolane and $CH[C(O)OR^{10}]_2$; where $R^{10}$ is methyl, ethyl, n-propyl, isopropyl, n-butyl, s-butyl, iso-butyl or t-butyl.

Other examples of $R^4$ groups include azide and tetrazole.

Still further examples of $R^4$ groups include —NH-tetrazole, —C(O)NHSO$_2$R$^{30}$ and —NHC(O)NHSO$_2$R$^{30}$; where $R^{30}$ is as defined above and tetrazoles substituted as defined above.

In some suitable compounds of general formulae (I), (IA), (IB), (IC), (ID) and (IE), $R^5$ is H.

In other suitable compounds of general formulae (I), (IA), (IB), (IC), (ID) and (IE), $R^5$ is OH.

In still other suitable compounds of general formulae (I), (IA), (IB), (IC), (ID) and (IE), $R^5$ is a protected OH group.

When $R^5$ is a protected OH group, it may be a group which is not stable in a basic environment such that treatment with a base converts the protected OH group to OH. Examples of such groups are well known in the art and include a group $OC(O)R^{14}$ as defined above in which $R^{14}$ is a group $R^{10}$ as defined above for general formula (I). Particularly suitable $R^{14}$ groups are as defined for $R^{10}$ above.

Alternatively, $R^5$ may be a protected OH group which is stable in a basic environment. Examples of such groups include $OSi(R^{16})_3$, where each $R^{16}$ is as defined above.

Particularly suitable $R^{16}$ groups are as defined above.

Specific compounds of general formula (I) include the following:
(6α, 7α, 20S)-20-(1-bromomethyl)-6,7-epoxy-pregn-4-en-3-one;
(6α, 7α, 20S)-6,7-epoxy-20-(ethylenedioxymethyl)-pregn-4-en-3-one;
(6α, 7α, 20S)-6,7-epoxy-20-azidomethyl-pregna-4-en-3-one;
(6α, 7α)-6,7-epoxy-3-oxo-4-cholen-23-carboxy-24-oic acid dimethyl ester;
(6β, 7α)-6-ethyl-7-hydroxy-3-oxo-4-cholen-23-carboxy-24-oic acid dimethyl ester;
(5β, 6β, 7α)-6-ethyl-7-hydroxy-3-oxo-cholan-23-carboxy-24-oic acid dimethyl ester;
(5β, 6β)-6-ethyl-3,7-dioxo-cholan-23-carboxy-24-oic acid dimethyl ester;
(5β, 6α)-6-ethyl-3,7-dioxo-cholan-23-carboxy-24-oic acid dimethyl ester;
(5β, 6α)-6-ethyl-3,7-dioxo-cholan-23-carboxy-24-oic acid;
(6α, 7α)-6,7-epoxy-3-oxo-4-choleno-24-nitrile;
(6β, 7α)-6-ethyl-7-hydroxy-3-oxo-4-choleno-24-nitrile;
(5β, 6β, 7α)-6-ethyl-7-hydroxy-3-oxo-cholano-24-nitrile;
(5β, 6β)-3,7-dioxo-6-ethyl-cholano-24-nitrile;
(3α, 5β, 6β)-6-ethyl-3-hydroxy-7-oxo-cholano-24-nitrile;
(6α, 7α, 20R)-20-(1-cyanomethyl)-6,7-epoxy-pregn-4-en-3-one;
(6β, 7α, 20R)-cyanomethyl-6-ethyl-7-hydroxy-4-pregnen-3-one;
(5β, 6β, 7α, 20R)-cyanomethyl-6-ethyl-7-hydroxy-pregna-3-one;
(5β, 6β, 20R)-cyanomethyl-6-ethyl-7-oxo-pregna-3-one;
(6β, 7α, 20S)-20-(ethylenedioxymethyl)-6-ethyl-7-hydroxy-pregna-4-en-3-one;
(5β, 6β, 7α, 20S)-20-(ethylenedioxymethyl)-6-ethyl-7-hydroxy-pregna-3-one;
(5β, 6β, 20S)-20-(ethylenedioxymethyl)-6-ethyl-pregna-3,7-dione;
(5β, 6α, 20S)-20-(ethylenedioxymethyl)-6-ethyl-pregna-3,7-dione;
or salts thereof.

As discussed in greater detail below, compounds of formula (IF) are analogues of obeticholic acid and similar compounds of general formula (XXI) and may be used as synthetic precursors of such compounds.

Compounds of general formula (IF) may be prepared from compounds of general formula (IE) by reduction of a compound of general formula (IE) using a suitable reducing agent and, where $R^3$ and/or $R^5$ is a protected OH, optional removal of the protecting group(s), to give a compound of general formula (IF) as defined above, wherein removal of the protecting group can take place before or after the reduction.

The reducing agent is typically a hydride, such as sodium borohydride which may be used in a solvent such as a mixture of tetrahydrofuran and water. Typically, this reaction is carried out under basic conditions, for example in the presence of a strong base such as sodium or potassium hydroxide and at a temperature of about 0 to 110° C., more usually 60 to 100° C.

Compounds of general formula (IE) may be prepared from compounds of general formula (ID) as defined above by epimerisation.

The epimerisation reaction suitably comprises treating the compound of general formula (ID) with a base. The compound of general formula (ID) may be dissolved in an alcoholic solvent, optionally mixed with water and contacted with a base, for example sodium or potassium hydroxide or a sodium or potassium alkoxide, typically an ethoxide.

If, in the compound of general formula (ID), $R^3$ and/or $R^5$ is a protected OH, for example a group $OC(O)R^{14}$, where $R^{14}$ is as defined above but is especially $C_{1-6}$ alkyl or phenyl, this will be removed during the epimerisation reaction to give a compound of general formula (IE) in which $R^3$ and/or $R^5$ is OH. Other protected OH groups which are stable in basic conditions (for example a group $OSi(R^{16})_3$ where each $R^{16}$ is independently as defined above but is especially $C_{1-6}$ alkyl or phenyl) may be removed subsequently to give a compound of general formula (IE) in which $R^3$ and/or $R^5$ is OH.

A compound of general formula (ID) can be prepared by oxidising a compound of general formula (IC) as defined above using any suitable method.

One suitable method is a Dess-Martin periodinane (1,1,1-triacetoxy-1,1-dihydro-1,2-benziodoxol-3-(1H)-one) oxidation, which may be carried out in a chlorinated solvent such as chloroform or dichloromethane at a temperature of about −5 to 40° C., suitably 0 to 30° C., for example 15 to 25° C., suitably at room temperature.

An alternative oxidation method is oxidation using a hypochlorite, for example sodium hypochlorite, under acidic conditions, for example provided by acetic acid. The reaction may be carried out in an aqueous solvent and at a temperature of 0 to 15° C., more usually at about 0 to 10° C.

Other oxidation methods include a Jones reaction using sodium dichromate or, more usually, chromic trioxide in dilute sulfuric acid. This process is known to be reliable for the clean conversion of bile acid hydroxyl groups to the corresponding keto derivatives (Bortolini et al, *J. Org. Chem.*, 2002, 67, 5802). Alternatively oxidation may be carried out using TEMPO ((2,2,6,6-Tetramethyl-piperidin-1-yl)oxy) or a derivative thereof.

Compounds of general formula (IC) may be prepared from compounds of general formula (IB) as defined above by reduction.

The reduction may be hydrogenation, usually catalytic hydrogenation. Suitable catalysts for the catalytic hydrogenation include a palladium/carbon, palladium/calcium carbonate, palladium/aluminium oxide, platinum/palladium or Raney nickel catalyst. The reaction may be carried out in an organic solvent, which may be an alcoholic solvent such as methanol, ethanol or isopropanol; ethyl acetate; pyridine; acetic acid; cyclopentyl methyl ether (CPME), acetonitrile (MeCN) or N,N-dimethylformamide (DMF). The organic solvent may optionally be mixed with a co-solvent such as acetone or water and/or a base such as triethylamine may also be added.

The choice of catalyst and solvent affects the ratio of the required product of general formula (IC):

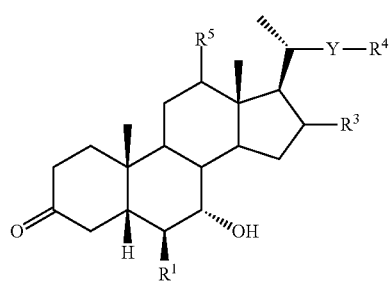

(IC)

to its isomer of general formula (IG):

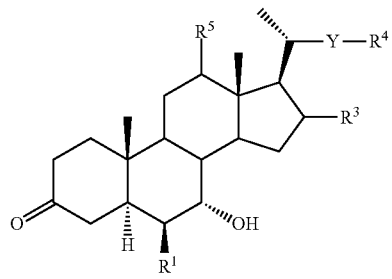

(IG)

It also affects the rate of conversion of the reaction intermediate to the product.

More suitably, a palladium/carbon or palladium/calcium carbonate catalyst is used. Typically, in the catalyst the palladium is present in an amount of 5-10% by weight with respect to the weight of the matrix (where the matrix is the carbon, calcium carbonate etc).

Particularly suitable solvents and catalysts used for the reaction included a mixture of DMF and MeCN with a palladium/calcium carbonate catalyst and DMF with a palladium/carbon catalyst.

Hydrogenation of a compound of formula (IB) will also reduce any alkene bonds, if present, in the linker Y.

Compounds of general formula (IB) may be prepared from compounds of general formula (IA) as defined above by selective alkylation with an organometallic reagent.

Suitable organometallic reagents include Gilman reagents formed by reaction of an alkyl lithium compound of formula (XXX):

$R^1$—Li     (XXX)

wherein $R^1$ is as defined for general formula (I);

and a copper (I) salt, particularly a copper (I) halide such as copper (I) iodide.

The reaction may be conducted in an organic solvent such as tetrahydrofuran, other ethers such as diethylether or a mixture thereof.

Alternatively, the addition can be carried out using Grignard reagents $R^1$MgX, where $R^1$ is as defined for general formula (I) and X is a halide, for example ethylmagnesium bromide and the reaction is suitably conducted in the presence of a zinc (II) salt such as zinc chloride and a catalytic amount of a copper (I) or copper(II) salt or complex, for example copper (I) chloride, copper (II) chloride or a copper(I) or copper (II) acetylacetonate (acac) complex.

The reaction may be carried out in an organic solvent, for example an ether such as THF, 2-methyl THF, methyl tert-butyl ether (tBME), diethyl ether. Surprisingly, the reaction temperature is not particularly significant and while in some cases the reaction may be carried out at reduced temperature, for example at about −25 to 0° C., it has also been successfully conducted at higher temperatures of up to about 55° C.

Compounds of general formula (IA) may be prepared from compounds of formula (II):

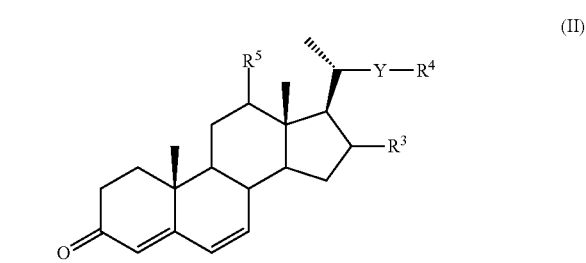

(II)

wherein $R^3$, $R^4$, $R^5$ and Y are as defined in general formula (I);

by oxidation, for example using methyltrioxorhenium (MTO), monoperoxyphthalate (MMPP) or 3-chloroperoxybenzoic acid, (mCPBA).

The reaction using MMPP may be carried out in an organic solvent such as ethyl acetate and if mCPBA is used, the reaction may be carried out in a solvent such as dichloromethane, ethyl acetate or toluene. Suitably, the reaction is conducted at or just below the reflux temperature of the solvent.

Compounds of general formula (II) may be prepared from compounds of general formula (III):

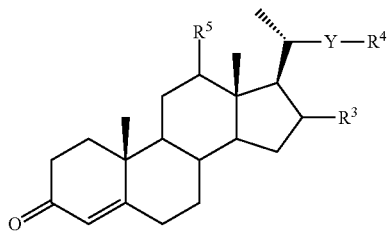

wherein $R^3$, $R^4$, $R^5$ and Y are as defined in general formula (I);

by reaction with an oxidizing agent such as chloranil.

The reaction may be carried out under acidic conditions, for example in the presence of acetic acid, and in an organic solvent such as toluene.

Analogues of compounds of general formulae (IA), (II) and (III) are known and, for example Uekawa et al in *Biosci. Biotechnol. Biochem.*, 2004, 68, 1332-1337 describe the synthesis of (22E)-3-oxo-4,22-choladien-24-oic acid ethyl ester from stigmasterol followed by its conversion to (22E)-3-oxo-4,6,22-cholatrien-24-oic acid ethyl ester, which has the formula:

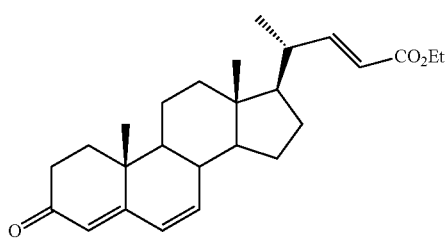

Uekawa et al then go on to describe the conversion of this compound to (6α, 7α, 22E)-6,7-epoxy-3-oxo-4,22-choladien-24-oic acid ethyl ester, an analogue of a compound of general formula (IA) in which $R^3$ and $R^5$ are H, Y is —CH=CH—, and the group in the $R^4$ position is C(O)OCH$_2$CH$_3$.

Other compounds of general formulae (IA), (II) and (III) may be prepared by analogous methods from phytosterols similar to stigmasterol.

Stigmasterol and other phytosterols are plant sterols and are readily available or may be prepared by known routes.

Compounds of general formula (III) may also be prepared from compounds of general formula (IV):

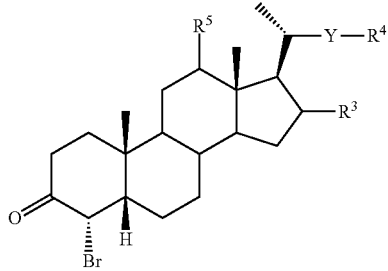

wherein $R^3$, $R^4$, $R^5$ and Y are as defined in general formula (I);

by reaction with lithium bromide and a base such as lithium carbonate. The reaction may be carried out in a solvent such as N,N-dimethylformamide (DMF) and at a temperature of about 120 to 180° C.

Compounds of general formula (IV) may be obtained by bromination of a compound of general formula (V):

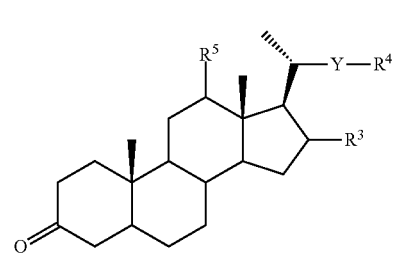

wherein $R^3$, $R^4$, $R^5$ and Y are as defined in general formula (I);

using, for example bromine in acetic acid.

Compounds of general formula (V) may be prepared from compounds of general formula (VI):

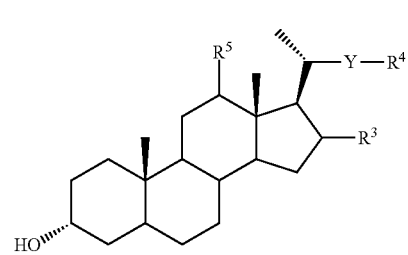

wherein $R^3$, $R^4$, $R^5$ and Y are as defined in general formula (I);

by oxidation, typically with a chromium-based oxidizing agent or with sodium hypochlorite.

Analogues of compounds of general formula (VI) in which the group at the $R^4$ position is C(O)OR$^{10}$b, where $R^{10b}$ is C$_{1-6}$ alkyl or benzyl may be prepared from analogues of compounds of general formula (VI) in which the group at the $R^4$ position is C(O)OH by esterification, typically by reaction with an appropriate alcohol under acidic conditions. The analogue may be converted to a compound of general formula (VI) by converting the group C(O)OR$^{10b}$ to a group $R^4$ as above defined using one of the methods described below.

Analogues of general formula (VI) in which the group at the $R^4$ position is C(O)OH and $R^5$ is H may be prepared from compounds of general formula (VII):

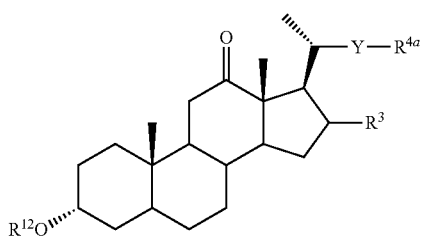

(VII)

wherein $R^3$ and Y are as defined in general formula (I); $R^{4a}$ is $C(O)OR^{10b}$, where $R^{10b}$ is $C_{1-6}$ alkyl or benzyl; and $R^{12}$ is a protecting group;

by reaction with a reducing agent, typically hydrazine under basic conditions and in an alcoholic or glycolic solvent, for example diethylene glycol. If required, the side chain may be converted to a desired $R^4$ group as above defined, as discussed in greater detail below.

Where $R^{12}$ is a protecting group which is stable under basic conditions, the reaction may be followed by a reaction to remove the protecting group $R^{12}$ to leave an OH group.

Protecting groups for OH are discussed above and, for example, $R^{12}$ may be a group $C(O)R^{14}$, where $R^{14}$ is as defined above, in particular, $C_{1-6}$ alkyl or benzyl. Silyl ethers are also suitable, and in this case, $R^{12}$ may be a group $Si(R^{16})_3$, where $R^{16}$ is as defined above but is especially $C_{1-6}$ alkyl or phenyl. Other suitable protecting groups for OH are well known to those of skill in the art (see Wuts, P G M and Greene, T W (2006) "Greene's Protective Groups in Organic Synthesis", 4th Edition, John Wiley & Sons, Inc., Hoboken, N.J., USA).

Particularly suitable $R^{12}$ groups include groups which are not stable in the presence of a base since this removes the need for the additional step of removing the protecting group. An example of a group $R^{12}$ which is not stable in basic conditions is a group $C(O)R^{14}$ where $R^{14}$ is as defined above, and is in particular $C_{1-6}$ alkyl or phenyl.

Alternatively, the reaction may be carried out in 2 steps such that the compound of general formula (VII) is reacted with a compound of general formula (VIII):

$R^{20}$—NH—NH$_2$ (VIII)

wherein $R^{20}$ is a leaving group such as toluene sulfonyl or methane sulfonyl;

to give a compound of general formula (IX):

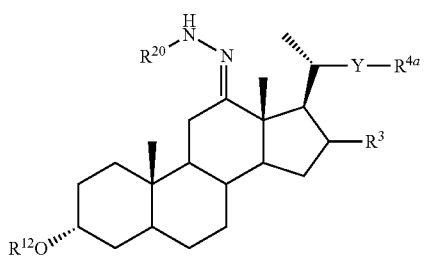

(IX)

wherein $R^3$ and Y are as defined in general formula (I); $R^{4a}$ and $R^{12}$ are as defined for general formula (VII); $R^{20}$ is as defined for general formula (VIII);

followed by reduction with a suitable reducing agent. Examples of reducing agents which can be used in this reaction include hydrides such as sodium borohydride, sodium cyanoborohydride, lithium aluminium hydride etc.

Compounds of general formula (VII) may be prepared from compounds of general formula (X):

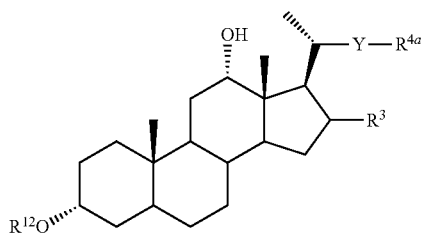

(X)

wherein $R^3$ and Y are as defined in general formula (I) $R^{4a}$ is as defined above for general formula (VII); and $R^{12}$ is as defined above for general formula (VII) and is suitably —$C(O)C_{1-6}$ alkyl;

by reaction with an oxidizing agent, for example sodium hypochlorite.

The reaction may be carried out under acidic conditions, for example in the presence of acetic acid, and in an organic solvent such as ethyl acetate.

Compounds of general formula (X) may be prepared from compounds of general formula (XII):

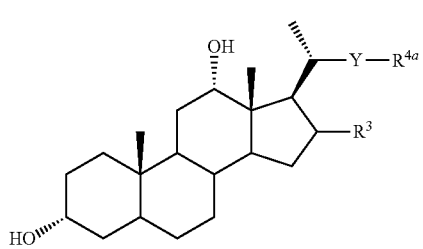

(XII)

wherein $R^3$ and Y are as defined for general formula (I); $R^{4a}$ is as defined above for general formula (VII);

by reaction with an agent suitable to introduce the protecting group $R^{12}$. For example, when $R^{12}$ is $C(O)R^{14}$, the compound of general formula (XII) may be reacted with a carboxylic acid anhydride or an acid chloride in the presence of a weak base such as pyridine, suitably catalysed by 4-dimethylaminopyridine (DMAP). The reaction may be conducted in a solvent such as ethyl acetate.

Compounds of general formula (XII) may be prepared by the esterification of compounds of general formula (XIII):

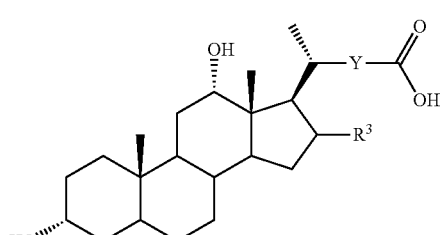

(XIII)

wherein $R^3$ and Y are as defined for general formula (I); followed by conversion of the ester group to a group $R^4$ as above defined.

The esterification reaction may be carried out by reacting the acid of general formula (XIII) with a suitable alcohol under acidic conditions.

Compounds of general formula (XIII) are known. For example, the compound of general formula (XIII) in which Y is —$CH_2CH_2$— and $R^3$ is H is deoxycholic acid, which is readily available from a number of sources.

Other compounds with different values for Y and $R^3$ can be used as alternative starting materials.

Any of compounds (I) to (VII) and (IX) to (XIII) as defined above can be obtained by converting a side chain carboxylic acid, ester, OH or protected OH group to a group $R^4$ as defined above. This conversion may be carried out by known methods. For example, in a compound of general formula (XII), the ester may firstly be reduced to give an alcohol of general formula (XIV):

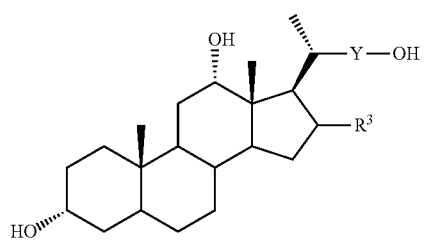

(XIV)

wherein Y is $Y^2$—$CH_2$— and $Y^2$ is as defined for Y except that it is shorter in length by at least one carbon atom;

and $R^3$ is as defined above for general formula (I).

The reaction may be carried out in two or more steps. In a first step, OH groups in the compound of general formula (XII) may be protected by reaction with a compound of general formula (XV):

wherein $R^{16}$ is as defined above and $X^1$ is a leaving group, for example a halide such as chloride or a sulfonate leaving group such as trifluoromethanesulfonate (triflate), methanesulfonate (mesylate) or toluene sulfonate (tosylate);

in the presence of a base such as 2,6-lutidine or triethylamine. In the second step, the product of this reaction is reduced, suitably using a hydride such as lithium aluminium hydride or lithium borohydride. This reaction is suitably conducted in an organic solvent, for example a mixture of methanol and tetrahydrofuran.

Analogues of compounds of general formula (III) in which $R^4$ is OH can also be prepared from plant sterols. For example, Scheme 3 of Example 1 illustrates the preparation of a compound of general formula (III) from stigmasterol via an Oppenauer oxidation followed by ozonolysis and reduction with sodium borohydride.

Alternatively, analogues of compounds of general formulae (I) to (VII) and (IX) to (XII) in which the group at the $R^4$ position is —OH may be prepared from an analogue of a compound of general formulae (I) to (VII) and (IX) to (XII) in which $R^4$ is $OC(O)R^{10}$ by reaction with a base, typically sodium hydroxide as shown in Scheme 3 and Example 1, step C, and Example 7, Scheme 8.

Alcohols with a side chain Y—OH ($Y^2$—$CH_2$—OH) can be converted to compounds of general formula (I) to (VII) and (IX) to (XII) in which the side chain is —$Y^2$—C(O)H by oxidation, for example using oxalyl chloride suitably in the presence of dimethyl sulfoxide and a base such as trimethylamine. Alternatively, the oxidation may be carried out using Dess-Martin periodinane as shown in Schemes 3 and 8 of Examples 1 and 6 or using sodium hypochlorite.

In compounds of general formulae (I) to (VII) and (IX) to (XII) in which the side chain is —$Y^2$—C(O)H, the side chain can be extended, for example using an olefination reaction with a compound of general formula (XVI):

where $Y^3$ is as defined for Y in general formula (I) except that it may have a shorter carbon chain such that the linker Y of general formula (I) can be a moiety —$Y^2$—$CH_2CH_2$—$Y^3$—, wherein $Y^2$ and $Y^3$ are as defined for Y except that they are shorter in length;

$R^{27}$ is suitably $C_{1-6}$ alkyl or benzyl;

To give a compound in which the side chain is $Y^2$—CH=CH—$Y^3$—$C(O)OR^{27}$.

The olefination reaction may be carried out at about 15 to 25° C., suitably room temperature, in a solvent such as dichloromethane. This reaction is illustrated in Scheme 8 of Example 7.

These compounds can, in turn, be converted to compounds in which $R^4$ is the carboxylic acid mimetic group $C(O)NHSO_2R^{30}$, wherein $R^{30}$ is as defined above, by reaction with:

wherein $R^{30}$ is as defined above, in the presence of a coupling agent such as 1-ethyl-3(3-dimethylaminopropyl) carbodiimide (EDCI).

Analogues of compounds of general formulae (I) to (VII) and (IX) to (XII) in which the group at the $R^4$ position is OH can be protected with a silyl protecting group. This may be achieved by reaction with a compound of general formula (XV) as described above, typically in an organic solvent and in the presence of a base, for example imidazole, or triethylamine. This reaction is shown in Example 1D.

As shown in Scheme 3 of Example 1, analogues of compounds of general formulae (I) to (VII) and (IX) to (XII) in which the group at the $R^4$ position is OH may also be converted to analogues of compounds of general formulae (I) to (VII) and (IX) to (XII) in which the group at the $R^4$ position is a sulfonate, for example methane sulfonate or toluene sulfonate, by reaction with a sulfonyl halide such as methane sulfonyl chloride, in the presence of a catalyst such as 4-dimethylaminopyridine (DMAP). Alternatively, they may be converted to compounds of general formulae (I) to (VII) and (IX) to (XII) in which $R^4$ is halo, for example bromo, by reaction with a halogenating agent, e.g. a brominating agent such as carbon tetrabromide as illustrated in Example 1J or N-bromosuccinimide, as illustrated in Example 3A.

Such sulfonate or halide compounds can then be converted to compounds of general formulae (I) to (VII) and (IX) to (XII) in which $R^4$ is cyano by reaction with a cyanide salt, for example sodium or potassium cyanide (see Example 1I and Example 5, Scheme 6). Alternatively, reaction with acetonitrile in the presence of a base such as n-butyl lithium leads to a chain lengthening reaction so that, for example, a side chain —$CH_2$—O— methanesulfonyl or —$CH_2$—Br is converted to a side chain —$CH_2CH_2$—CN (see Example 4, Scheme 5).

Compounds with a sulfonate or bromide side chain can also be converted to compounds in which $R^4$ is nitro by reaction with nitromethane in the presence of a base.

Compounds of general formulae (I) to (VII) and (IX) to (XIII) in which the side chain is $Y^2$—C(O)OH or an ester thereof may be converted to compounds in which the side chain is $Y^2$—CH=CH$_2$ by reaction with PhI(OAc)$_2$ in the presence of copper (II) acetate using a process similar to Hunsdiecker reaction (see J. Org. Chem., 1986, 51, 404-407 and V. C. Edelsztein et al. *Tetrahedron* 65 (2009), 3615-3623).

The compounds with side chain —$Y^2$—CH=CH$_2$ may in turn be oxidised using, for example, osmium tetroxide as described in J. Org. Chem., 1986, 51, 404-407 to give a compound in which the side chain is —$Y^2$—CH(OH)—CH$_2$—OH. Such compounds may be oxidised to compounds in which the side chain is $Y^2$—CH(OH)—C(O)H, which may then be protected as a 1,3-dioxane or 1,3-dioxolane by reaction with 1,3-propane diol or 1,2-ethandiol in the presence of an acid catalyst such as toluene sulfonic acid. Similar reactions can be used to prepare the equivalent cyclic thioethers.

Compounds of general formulae (I) to (VII) and (IX) to (XIII) with side chain —Y—CH=CH$_2$ may also be prepared by reduction of a compound with side chain —Y≡C—CH, typically by hydrogenation over a palladium catalyst, suitably Lindlar catalyst.

Compounds of general formulae (I) to (VII) and (IX) to (XIII) with side chain —Y—C≡CH may be prepared from compounds with side chain Y—X, where X is a halo group, particularly bromo, by reaction with an organometallic reagent, for example:

Li—C≡CH.

As described above, compounds of general formulae (I) to (VII) and (IX) to (XIII) wherein $R^4$ is halo may be prepared from a corresponding compound in which $R^4$ is OH (for example a compound of general formula (XIV)) by a halogenation reaction. For example, when $R^4$ is bromo, the compound of wherein $R^4$ is OH may be reacted with a brominating agent such as carbon tetrabromide, N-bromo-succinimide or phosphorus tribromide.

Compounds of general formulae (I) to (VII) and (IX) to (XIII) in which the side chain —Y—$R^4$ is —CH$_2$—OH may also be converted to compounds in which the side chain is =CH$_2$. This can be achieved by an elimination reaction in which the compound having side chain —Y—$R^4$ is —CH$_2$—OH is reacted with an acid such as phosphoric acid, sulphuric acid or toluene sulphonic acid. A similar reaction can be used to convert a compound with side chain —$Y^2$—CH$_2$—OH to a compound with side chain —$Y^2$—C=CH$_2$. Alternatively, compounds in which the side chain is =CH$_2$ can be prepared by oxidising —$Y^2$—CH$_2$—OH to $Y^2$—CH(O) and then converting this to an alkene using an olefination reaction.

Compounds of general formulae (I) to (VII) and (IX) to (XII) with side chain Y—C≡CH, =CH$_2$ or —$Y^2$—C=CH$_2$ may be reacted with a borane of formula:

H—BR$^{10}$R$^{11}$ to give compounds in which the side chain is —Y—CH$_2$—C(BR$^{10}$R$^{11}$)$_2$, —CH$_2$—BR$^{10}$R$^{11}$ or —$Y^2$—CH$_2$—BR$^{10}$R$^{11}$ respectively.

Compounds of general formulae (I) to (VII) and (IX) to (XII) in which the side chain is —CH$_2$—BR$^{10}$R$^{11}$ or —$Y^2$—CH$_2$—BR$^{10}$R$^{11}$ may be reacted with, for example phenoxy-acetic acid to give a corresponding compound in which the side chain is —CH$_2$—C(O)OH or —$Y^2$—CH$_2$—C(O)OH.

Compounds of general formulae (I) to (VII) and (IX) to (XII) in which $R^4$ is —CH[C(O)OR$^{10}$]$_2$ may be prepared from the corresponding compounds of general formulae (I) to (VII) and (IX) to (XII) in which $R^4$ is halo, for example bromo, by reaction with a malonate ester in the presence of a base such as sodium hydride. A reaction of this type is illustrated in Scheme 3 of Example 1 and described in Example 1K for a compound of general formula (II).

Compounds of general formulae (I) to (VII) and (IX) to (XII) in which $R^4$ is a malonate ester —CH[C(O)OR$^{10}$]$_2$ may be heated under basic or acidic conditions to give compounds in which $R^4$ is CH$_2$C(O)OH or, when basic conditions are used, a salt thereof. This reaction is shown in Example 3, Scheme 4 and Step L.

Compounds of general formulae (I) to (VII) and (IX) to (XIII) in which the side chain is —Y—C(O)OH may also be converted to compounds of general formulae (I) to (VII) and (IX) to (XIII) in which the side chain is —Y—C(O)—CH$_2$—N$_2$ by reaction with phosgene to form the acid chloride, followed by reaction with diazomethane.

The diazomethane may be formed in situ using conventional methods, e.g. the treatment of N-nitroso-N-methyl-urea with aqueous sodium or potassium hydroxide in diethyl ether. Suitably the diazomethane is used in excess, typically in an amount of greater than 2 equivalents compared with the acid chloride. The reaction is typically conducted in an organic solvent such as diethyl ether, toluene or a mixture thereof. The reaction is carried out at a temperature of about −5 to 15° C., typically 0-10° C.

The compound with side chain —Y—C(O)—CH$_2$—N$_2$ may be treated with an aqueous silver compound, for example silver nitrate, at an elevated temperature and in the presence of an alcohol of formula:

R$^{10a}$—OH wherein R$^{10a}$ is as defined for R$^{10}$ in general formula (I) except that it is not H. Most suitably, R$^{10a}$ is C$_{1-6}$ alkyl or benzyl. Under these conditions, the compound undergoes a Wolff rearrangement to give a compound of general formula (I) to (VII) and (IX) to (XIII) in which the side chain is —Y—CH$_2$—C(O)OH and thus this sequence can be used to lengthen the side chain.

Compounds of general formulae (I) to (VII) and (IX) to (XIII) in which the side chain is Y—C(O)OH, i.e. Y$^2$CH$_2$CH$_2$C(O)OH may be converted to compounds in which the side chain is —$Y^2$—CH$_2$—CN by reaction with sodium nitrite under acidic conditions, for example in the presence of trifluoroacetic acid and trifluroroacetic anhydride (C. D. Schteingart and A. T. Hofmann, *Journal of Lipid Research*, (1988), 29, 1387-1395; Valentina Sepe et al, *Eur. J. Org. Chem.* 2012, 5187-5194).

Compounds of general formulae (I) to (VII) and (IX) to (XII) in which the side chain is Y—C(O)H may be converted to compounds in which the side chain is —Y—CH(OR$^{10}$)(OR$^{11}$) or —Y—CH(SR$^{10}$)(SR$^{11}$) where R$^{10}$ and R$^{11}$ together with the atoms to which they are attached join to form a cyclic group. This can be achieved by reacting the compound in which the side chain is Y—C(O)H with a compound of formula:

HX$^3$—(CH$_2$)$_p$—X$^3$H where X$^3$ is O or S and p is 2 to 4 but usually is 2 or 3; or with a protected version of such a compound, for example in which OH or SH groups are protected with trimethylsilyl as shown in Scheme 3, Example 1F and in the first step of Scheme 7 of Example 6.

Compounds of general formulae (I) to (VII) and (IX) to (XII) in which the side chain is $Y^2$—C(O)H may also be converted to compounds with side chain —$Y^2$—CH(OH)—CH$_2$—CH(OR$^{10}$)(OR$^{11}$), —$Y^2$—CH(OH)—CH$_2$—CH(R$^{10}$)(OR$^{11}$) or —$Y^2$—CH(OH)—CH$_2$—CH(SR$^{10}$)(SR$^{11}$)

by reaction with an appropriate organometallic reagent, typically a Grignard reagent of formula:

XMg—CH$_2$—R$^{4c}$;

where X is halo, typically bromo, and R$^{4c}$ —CH(OR$^{10}$)(OR$^{11}$), —CH(R$^{10}$)(OR$^{11}$) or CH(SR$^{10}$)(SR$^{11}$).

An example of this reaction is shown in Scheme 3 of Example 1.

Compounds of general formulae (I) to (VII) and (IX) to (XII) in which the side chain is —Y$^2$—CH(OH)—CH$_2$—CH(R$^{10}$)(OR$^{11}$) can be converted to compounds in which the side chain is —Y$^2$—CH=CH—C(O)H by reaction with an acid. Following this, the aldehyde can be oxidised to give a carboxylic acid and/or the alkylenene bond can be reduced by hydrogenation to give a saturated side chain in which Y is —Y$^2$—CH$_2$CH$_2$—.

Compounds of general formulae (I) to (VII) and (IX) to (XII) in which R$^4$ is —N$_3$ may be prepared from analogues of compounds of general formulae (I) to (VII) and (IX) to (XII) in which R$^4$ is a leaving group such as toluene sulfonyl, methane sulfonyl or compounds of general formulae (I) to (VII) and (IX) to (XII) in which R$^4$ is halo (for example bromo) by reaction with sodium azide. This is illustrated in Example 1G.

Compounds of general formulae (I) to (VII) and (IX) to (XII) in which R$^4$ is NH$_2$ may be obtained by reduction of compounds of general formulae (I) to (VII) and (IX) to (XII) in which R$^4$ is azide as illustrated in Example 1G.

Compounds of general formulae (I) to (VII) and (IX) to (XII) in which R$^4$ is —NHC(O)NHSO$_2$R$^{30}$ may be prepared from compounds in which R$^4$ is NH$_2$ using a coupling reaction with a compound of formula:

NH$_2$SO$_2$R$^{30}$ wherein R$^{30}$ is as defined above;
in the presence of a reagent such as N,N'-carbonyldiimidazole (CDI) or phosgene.

Compounds of general formulae (I) to (VII) and (IX) to (XII) in which R$^4$ is tetrazol-5-yl may be prepared from compounds of general formulae (I) to (VII) and (IX) to (XII) in which R$^4$ is CN by reaction with azidotrimethylsilane/dibutylstannanone or Bu$_3$SnN$_3$ as described in US 2016/0145295. Alternatively, the compound in which R$^4$ is CN may be reacted with sodium azide in the presence of an acid. For example, NaN$_3$/NH$_4$Cl in toluene/DMF (*Organic and Biomolecular Chemistry,* 2008, 6, 4108) or NaN$_3$/NEt$_3$.HCl in DMF (Brown et al; *Bioorg Med Chem Lett,* 2002, vol 12, pg 3171). Alternatively, a compound of general formula (I) in which R$^4$ is azide may be reacted with a suitable cyanide compound, for example toluene sulfonyl cyanide, under reducing conditions to give a compound in which R$^4$ is tetrazol-1-yl.

Compounds of general formulae (I) to (VII) and (IX) to (XII) in which R$^4$ is amino tetrazole can be prepared from an analogue in which the group at the R$^4$ position is methane sulfonyl by reaction with 5-amino tetrazole.

Compounds of general formulae (I) to (VII) and (IX) to (XIII) in which the side chain is —Y$^2$—C(O)H may also be converted to compounds —Y$^2$—CH$_2$—NR$^{10}$R$^{11}$ by reductive amination, using a reducing agent such as a hydride, borohydride or cyanoborohydride (for example sodium borohydride, sodium triacetoxyborohydride or sodium cyanoborohydride) and an amine of formula:

H—NR$^{10}$R$^{11}$ where R$^{10}$ and R$^{11}$ are as defined above.

Other reactions for modifying the side chains of compounds with a steroid type structure, such as the compounds of general formulae (I) to (VII) and (IX) to (XII), are discussed by Shingate & Hazra, *Chem. Rev.* 2014, 114, 6349-6382, which is incorporated by reference.

An alternative route to analogues of compounds of general formula (III) in which the group at the R$^4$ position is an ester is as shown in Scheme 1 in which androstenedione is converted to a compound of general formula (V) in which R$^3$ and R$^5$ are H; R$^4$ is —C(O)OCH$_3$ and Y is either —CH$_2$CH$_2$— or —CH=CH—.

Scheme 1

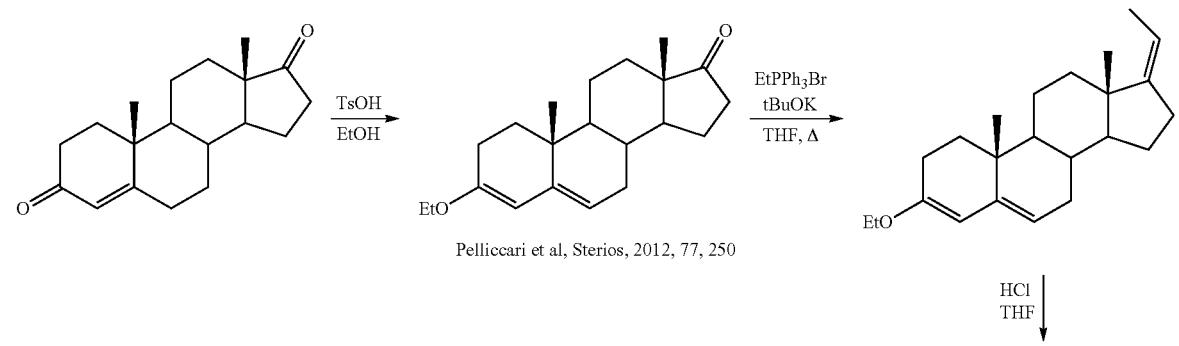

Pelliccari et al, Sterios, 2012, 77, 250

-continued

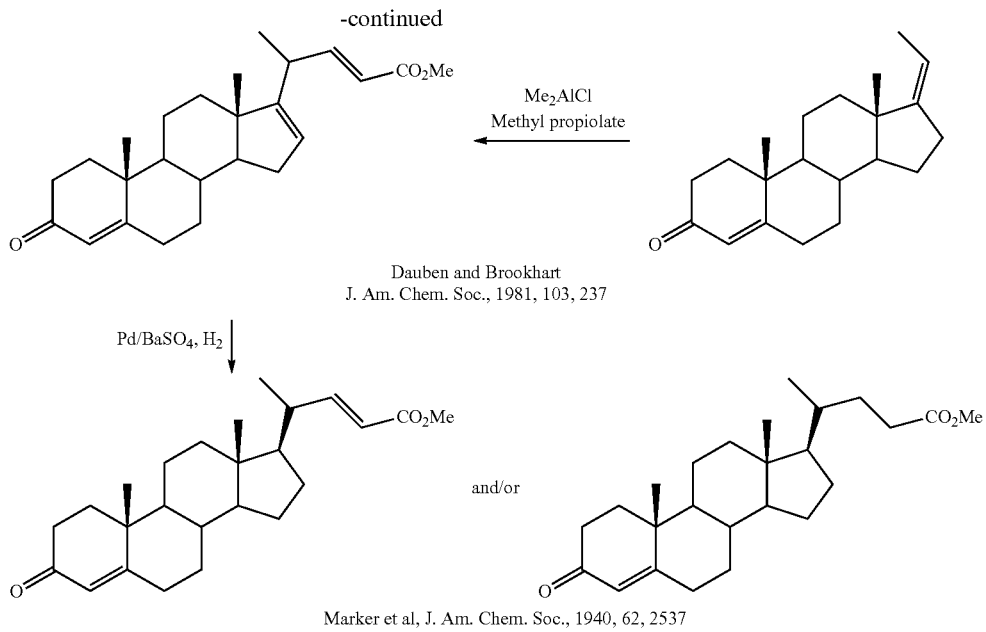

Dauben and Brookhart
J. Am. Chem. Soc., 1981, 103, 237

Marker et al, J. Am. Chem. Soc., 1940, 62, 2537

The ester group on the side chain may be converted to a group $R^4$ using the methods described above.

An alternative route to compounds of general formula (VI) in which Y is an alkenylene group is by use of an olefination reaction, for example a Horner-Wadsworth-Emmons (HWE) olefination of a compound of general formula (IIA):

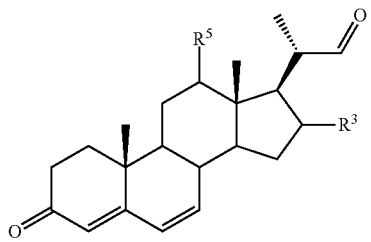

(IIA)

which is a compound of general formula (II) in which Y is a bond and $R^4$ is C(O)H and wherein $R^3$ and $R^5$ are as defined for general formula (I);

using a compound of general formula (XVII):

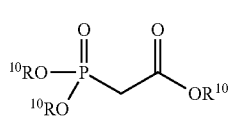

(XVII)

wherein $R^{10}$ is as defined for general formula (I).

The reaction may be carried out under standard HWE conditions, for example using a base such as sodium hydride.

Compounds of general formula (XVII) are readily available or may be prepared by methods known to those of skill in the art.

Other olefination reactions such as a Tebbe olefination, a Wittig type olefination or a Julia-Kocienski olefination would also give rise to compounds of general formula (III) in which Y is an alkenylene group. These olefination reactions are familiar to a chemist of skill in the art.

Compounds of general formula (IIA) may be prepared by reaction of a compound of general formula (XVIII) with ozone

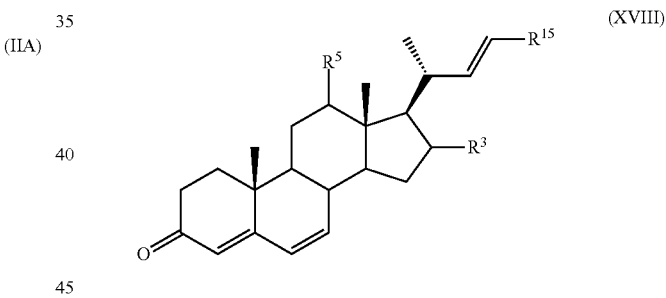

(XVIII)

wherein $R^3$ and $R^5$ are as defined for general formula (I) and $R^{15}$ is $C_{1-6}$ alkyl.

An example of a reaction of this type is given in U.S. Pat. No. 2,624,748.

Compounds of general formula (XVIII) may be prepared by reaction of a compound of general formula (XIX):

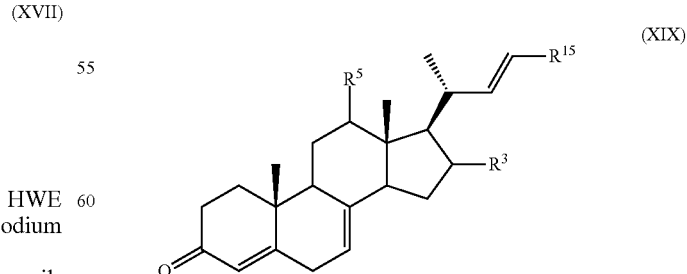

(XIX)

wherein $R^3$ and $R^5$ are as defined for general formula (I) and $R^{15}$ is $C_{1-6}$ alkyl;

with an acid in a solvent such as methanol.

Compounds of general formula (XIX) may be prepared by oxidation of a compound of general formula (XX):

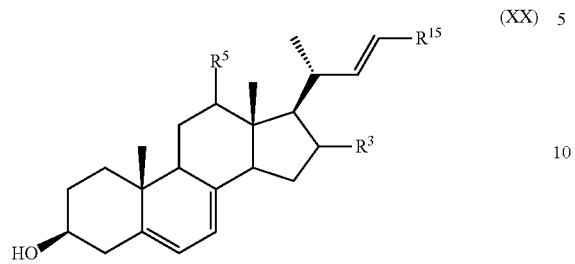

wherein $R^3$ and $R^5$ are as defined for general formula (I) and $R^{15}$ is $C_{1-6}$ alkyl using an Oppenauer oxidation.

Examples of the conversion of compounds of general formula (XX) to compounds of general formula (XVIII) are taught by Shepherd et al, *J. Am. Chem. Soc.* 1955, 77, 1212-1215 and Goldstein, *J. Med. Chem.* 1996, 39, 5092-5099.

One example of a compound of general formula (XX) is ergosterol, which is a fungal sterol and Scheme 2 below shows the conversion of ergosterol to a compound similar to general formula (II) in which both $R^3$ and $R^5$ are H, Y is $CH=CH_2$ but in which $R^4$ is replaced by $C(O)OR^{10}$, where $R^{10}$ is ethyl.

Scheme 2

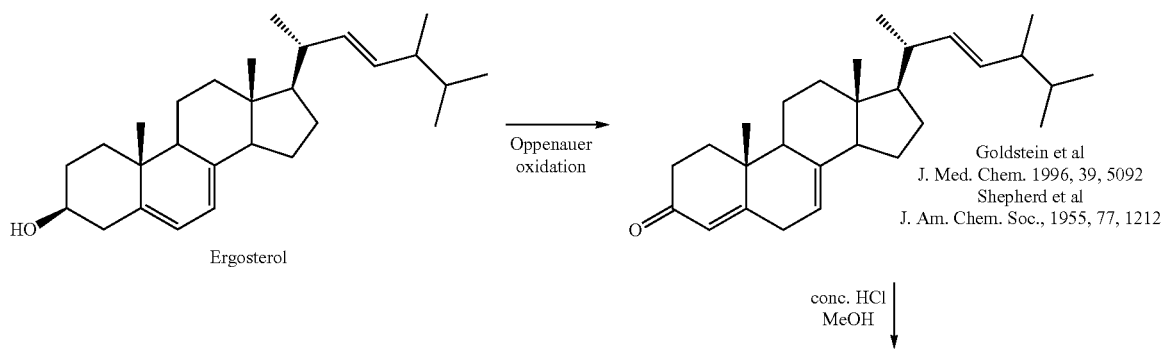

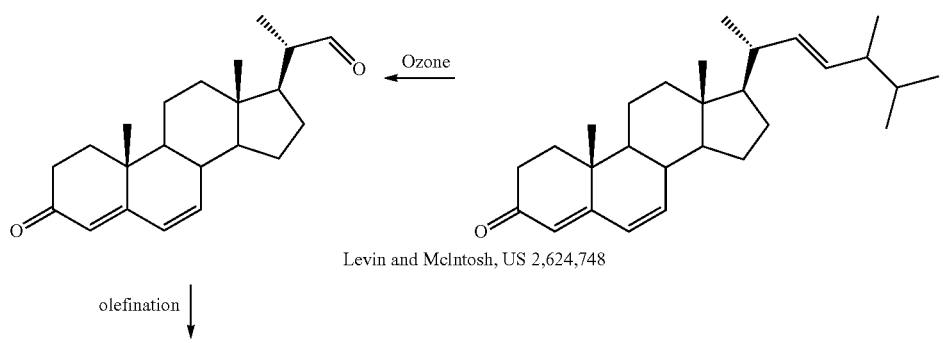

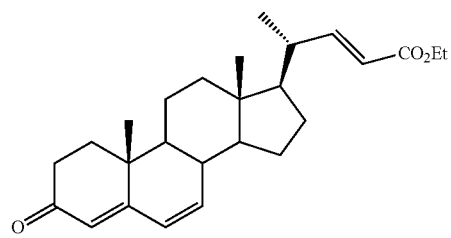 [SMILES: CCOC(=O)/C=C/[C@@H](C)[C@H]1CCC2C3C=CC4=CC(=O)CC[C@]4(C)C3CC[C@@]21C]

This compound can be converted to a compound of general formula (II) by modifying the side chain, for example as described above.

Compounds of general formula (I) are synthetic precursors of compounds of general formula (XXI):

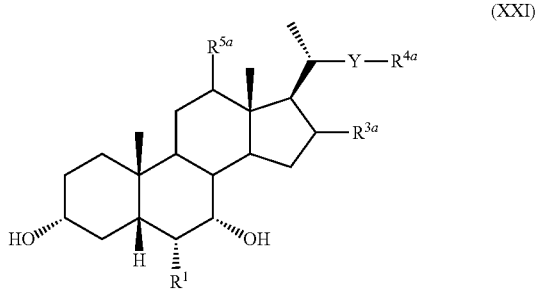

(XXI)

wherein $R^1$, and Y are as defined in general formula (I);
$R^{3a}$ is H, halo or OH;
$R^{4a}$ is $C(O)OR^{10}$, $C(O)NR^{10}R^{11}$, $S(O)R^{10}$, $SO_2R^{10}$, or $OSO_2R^{10}$; and
$R^{5a}$ is H or OH.

Compounds of general formula (XXI) are potent agonists of FXR and TGR5 and include, in particular, compounds in which $R^1$ is ethyl. Also included are the following.

Compounds in which $R^4$ is C(O)OH, for example:
  obeticholic acid, which is a compound of formula (XXI) in which $R^1$ is ethyl, $R^{3a}$ and $R^{5a}$ are both H, Y is —$CH_2CH_2$—, and $R^{4a}$ is C(O)OH; and
  the compound of formula (XXI) in which $R^1$ is ethyl, $R^{3a}$ and $R^{5a}$ are both H, Y is —$CH_2CH(CH_3)$—, and $R^{4a}$ is C(O)OH; and
  the compound of formula (XXI) in which $R^1$ is ethyl, $R^{3a}$ is H, $R^{5a}$ is OH, Y is —$CH_2CH(CH_3)$—, and $R^{4a}$ is C(O)OH.

Compounds in which $R^{4a}$ is $OSO_3H$ or a salt thereof, for example:
  the compound of formula (XXI) in which $R^1$ is ethyl, $R^{3a}$ and $R^{5a}$ are both H, Y is —$CH_2CH_2$—, and $R^{4a}$ is $OSO_3H$ or a salt thereof; and
  the compound of formula (XXI) in which $R^1$ is ethyl, $R^{3a}$ is H, $R^{5a}$ is OH, Y is —$CH_2CH_2CH_2$—, and $R^{4a}$ is $OSO_3H$ or a salt thereof; and
  the compound of formula (XXI) in which $R^1$ is ethyl, $R^{3a}$ is OH, $R^{5a}$ is H, Y is —$CH_2CH_2$—, and $R^{4a}$ is $OSO_3H$ or a salt thereof.

Therefore, in a further aspect of the invention there is provided a process for the preparation of a compound of general formula (XXI) as defined above, the process comprising converting a compound of general formula (I) to a compound of general formula (XXI) by a process comprising the step of converting the side chain substituent —$R^4$ of a compound of general formula (I) to a group $R^{4a}$ as defined above for general formula (XXI).

When $R^3$ and/or $R^5$ of the compound of general formula (I) is an OH protecting group, this protecting group will also be removed at an appropriate stage of the process to give a compound of general formula (XXI) in which $R^{3a}$ and/or $R^{5a}$ is OH.

The conversion of the side chain substituent —$R^4$ of a compound of general formula (I) to a group $R^{4a}$ as defined above for general formula (XXI) can take place at any stage of the process. For example, a compound of general formula (IA) may be converted to an analogue in which the side chain substituent is a group $R^{4a}$ as defined above and this analogue may be converted in turn to analogues of compounds of general formula (IB), (IC), (ID) and (IE), which may then be reduced as described above for the conversion of a compound of general formula (IE) to (IF) to obtain a compound of general formula (XXI).

Alternatively, a compound of general formula (IB) may be converted to an analogue in which the side chain substituent is a group $R^{4a}$ as defined above and this analogue may be converted in turn to analogues of compounds of general formula (IC), (ID) and (IE), which may then be reduced as described above for the conversion of a compound of general formula (IE) to (IF) to obtain a compound of general formula (XXI).

Alternatively, a compound of general formula (IC) may be converted to an analogue in which the side chain substituent is a group $R^{4a}$ as defined above and this analogue may be converted in turn to analogues of compounds of general formula (ID) and (IE), which may then be reduced as described above for the conversion of a compound of general formula (IE) to (IF) to obtain a compound of general formula (XXI).

Alternatively, a compound of general formula (ID) may be converted to an analogue in which the side chain substituent is a group $R^{4a}$ as defined above and this analogue may be converted to an analogue of the compound of general formula (IE), which may then be reduced as described above for the conversion of a compound of general formula (IE) to (IF) to obtain a compound of general formula (XXI).

Alternatively, a compound of general formula (IE) may be converted to an analogue in which the side chain substituent is a group $R^{4a}$ as defined above and this may then be reduced as described above for the conversion of a compound of general formula (IE) to (IF) to obtain a compound of general formula (XXI).

Alternatively, a compound of general formula (IE) may be converted to a compound of general formula (IF) by a process as described above and the compound of general formula (IF) may be converted to a compound of general formula (XXI) by converting the side chain substituent —$R^4$ to a group $R^{4a}$ as defined above for general formula (XXI).

For example, compounds of general formula (IF) in which the side chain is —$Y^2$—$C(OH)CH_2$—$CH(OR^{10})(OR^{11})$, particularly such compounds in which $R^{10}$ and $R^{11}$ form a cyclic ether group, may be deprotected to give a compound in which the side chain is —$Y^2$—$C(OH)CH_2$—C(O)H. Elimination of water gives a compound with side chain —$Y^2$—CH=CH—C(O)H and this compound can be oxidised to a compound with side chain —$Y^2$—CH=CH—C(O)OH, which is a compound of general formula (XXI).

Hydrogenation of this compound leads to saturation of the side chain double bond, giving a compound of general formula (XXI) in which the side chain is —$Y^2$—$CH_2CH_2$—C(O)OH.

Compounds of general formula (IF) in which the side chain is —$Y^2$—$CH_2$—CN may be hydrolysed to give a compound in which the side chain is —$Y^2$—$CH_2$—C(O)OH.

Compounds of formula (XXI) can be prepared from other compounds of general formula (XXI). For example, a compound of general formula (XXI) in which $R^{4a}$ is $C(O)OR^{10}$ may be converted to a compound of general formula (XXI) in which $R^{4a}$ is $C(O)NR^{10}R^{11}$, $S(O)R^{10}$, $SO_2R^{10}$, $OSO_2R^{10}$, $SO_3R^{10}$, or $OSO_3R^{10}$.

Compounds of general formula (XXI) in which $R^{4a}$ is $SO_3R^{10}$ may be synthesised from compounds of general formula (XXI) in which $R^{4a}$ is C(O)OH by the methods taught in WO2008/002573, WO2010/014836 and WO2014/066819.

Thus a compound of formula (XXI) in which $R^{4a}$ is C(O)OH may be reacted with a $C_{1-6}$ alkanoyl or benzoyl chloride or with a $C_{1-6}$ alkanoic anhydride to protect the OH groups. The protected compound may then be reacted with a reducing agent such as a hydride, suitably lithium aluminium hydride or sodium borohydride in order to reduce the carboxylic acid group to OH. The alcohol group may be replaced by a halogen, for example bromine or iodine, using the triphenyl phosphine/imidazole/halogen method described by Classon et al, *J. Org. Chem.*, 1988, 53, 6126-6130. The halogenated compound may then be reacted with sodium sulphite in an alcoholic solvent to give a compound with a $SO_3^-$ $Na^+$ substituent.

A compound of general formula (XXI) in which $R^{4a}$ is $OSO_3R^{10}$ can be obtained by reacting the alcohol obtained from reducing the protected carboxylic acid as described above with chlorosulfonic acid in the presence of a base such as triethylamine to yield the protected triethylamine salt. Protecting groups can be removed using base hydrolysis as described above. Reduction of the carboxylic acid followed by reaction of the resultant alcohol with sulfonyl chloride acid yields a compound of general formula (XXI) in which $R^4$ is $OSO_2R^{10}$.

Compounds of general formula (XXI) in which $R^{4a}$ is $C(O)NR^{10}R^{11}$ may be prepared from the carboxylic acid by reaction with an amine of formula $H-NR^{10}R^{11}$ in a suitable solvent with heating. Compounds of general formula (XXI) in which $R^{4a}$ is $C(O)NR^{10}R^{11}$ or $OSO_3R^{10}$ may also be prepared by methods similar to those described by Festa et al, *J. Med. Chem.*, 2014, 57, 8477-8495.

The methods for modifying the side chains also apply to compounds of general formulae (I) to (VII) and (IX) to (XIII).

The invention will now be further described with reference to the following examples.

ABBREVIATIONS USED IN EXAMPLES

| | |
|---|---|
| AcOH | Acetic acid |
| Aq. | Aqueous |
| nBuLi | n-Butyl lithium |
| DCM | Dichloromethane |
| DMF | N,N-dimethylformamide |
| DMAP | 4-Dimethylaminopyridine |
| DMP | Dess-Martin periodinane |
| EtOAc | Ethyl acetate |
| EtOH | Ethanol |
| EtMgBr | Ethyl magnesium bromide |
| h | Hour |
| HFIP | 1,1,1,3,3,3-Hexafluoro-2-propanol |
| HMPO | (20S)-20-hydroxymethyl-pregna-4-en-3-one also known as 20-hydroxymethylpregn-4-en-3-one and 3-keto-bis-norcholenol |
| IPA | Isopropanol |
| mCPBA | meta-chloroperoxybenzoic acid |
| MeCN | Acetonitrile |
| MeOH | Methanol |
| Mesyl | Methane sulfonyl |
| MsCl | Methane sulfonylchloride |
| MTO | Methyltrioxorhenium(VI) |
| NaOMe | Sodium methoxide |
| PhMe | Toluene |
| PTFE | Polytetrafluoroethylene |
| Py | Pyridine |
| TBDMSCl | tert-Butyldimethylsilyl chloride |
| TBME | tert-butyl methyl ether |
| TEPA | Triethyl phosphonoacetate |
| THF | Tetrahydrofuran |
| TLC | Thin layer chromatography |
| TMSOTf | Trimethyl silyl trifluoromethanesulfonate |
| Tosyl | Toluene sulfonyl |
| pTSA•H$_2$O | para toluene sulfonic acid monohydrate |
| UHP | Urea hydrogen peroxide |

Example 1—Preparation of Compounds of General Formula (II)

Scheme 3 below shows the conversion of an analogue of a compound of general formula (III) in which the side chain is —CH$_2$OH to analogues of a compound of general formula (II) in which the side chain is —CH$_2$OC(O)CH$_3$ and —CH$_2$OH and the subsequent conversion of this compound into other compounds of general formula (II) with different side chains.

Scheme 3
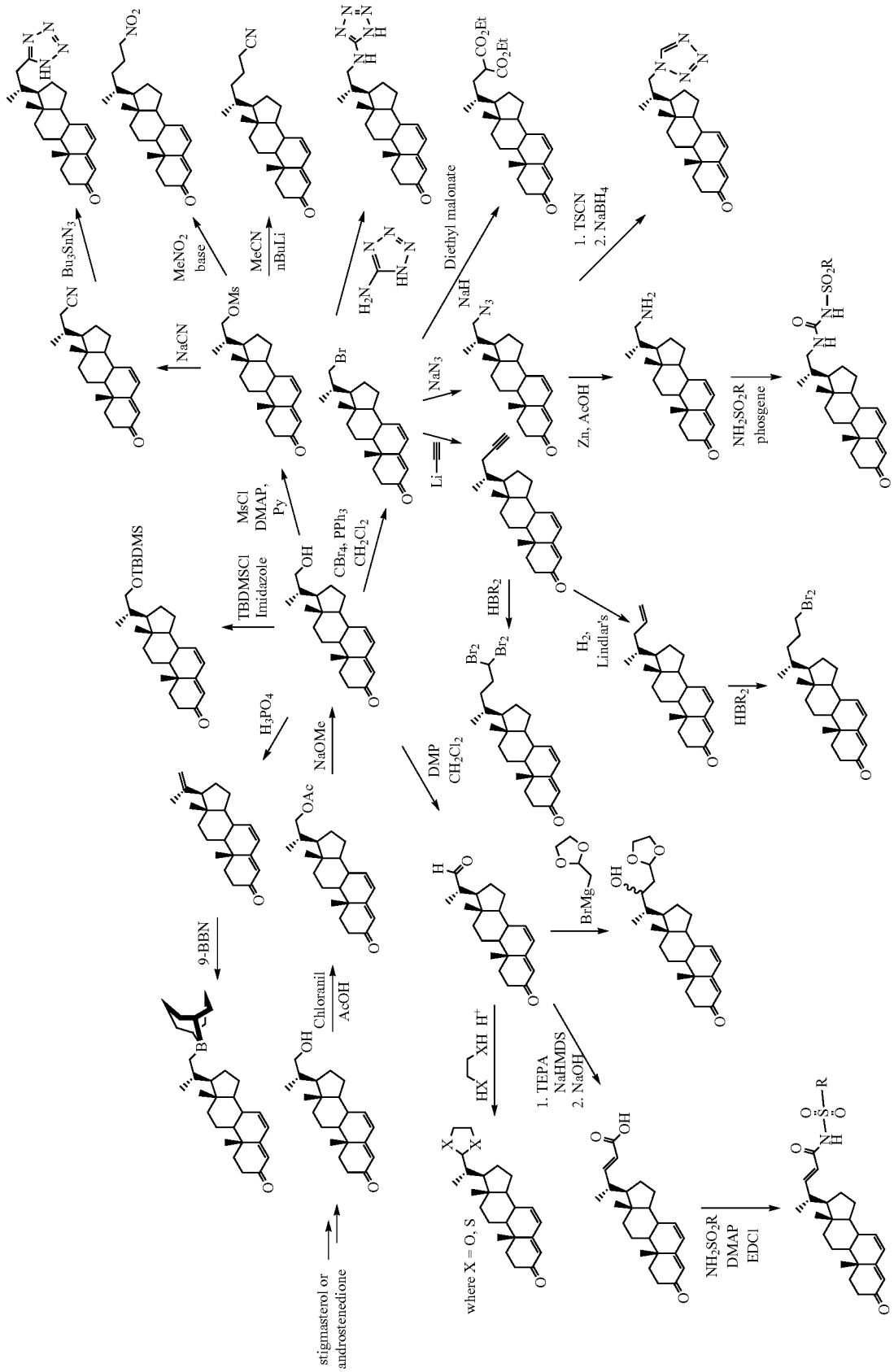

As shown in Scheme 3, the general formula (II) analogue with the —CH$_2$OH side chain can be converted to compounds of general formula (II) with side chains including —CH$_2$-9-borabicyclo(3.3.1) nonyl, —CH$_2$CH$_2$CH[B(alkyl)$_2$]$_2$, —CH$_2$CN, —CH$_2$CH$_2$CN, —CH$_2$Br, —CH$_2$CH[C(O)OEt]$_2$, —CH$_2$—C≡CH, —CH$_2$—CH═CH$_2$, ═CH$_2$, —C(O)H, —CH$_2$NH$_2$,

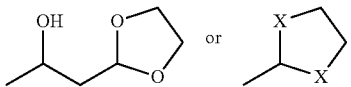

where X is O or S alkyl may be C$_{1-6}$ alkyl and Et is ethyl; and also carboxylic acid mimetic groups including —C(O)NHSO$_2$R$^{30}$ and —NHC(O)NH—SO$_2$R$^{30}$.

Synthesis of compounds of general formula (II) shown in Scheme 3 is described below.

A. Synthesis of (20S)-20-hydroxymethyl-pregna-4-en-3-one

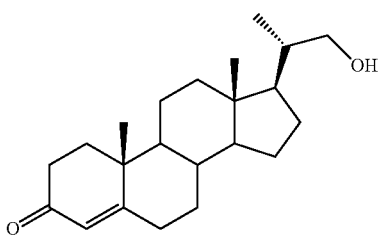 [SMILES: C[C@H](CO)[C@H]1CCC2C3CCC4=CC(=O)CC[C@]4(C)C3CC[C@@]21C]

(20S)-20-Hydroxymethyl-pregna-4-en-3-one (HMPO) can be prepared by chemoselective reduction of dinorcholenaldehyde ((20S)-20-formyl-pregn-4-en-3-one) with NaBH$_4$ in primary alcohol (Barry M. Trost, Alvin C. Lavoie *J. Am. Chem. Soc.*, 1983, 105(15), 5075-5090).

B. Synthesis of (20S)-20-acetoxymethyl-pregna-4,6-dien-3-one

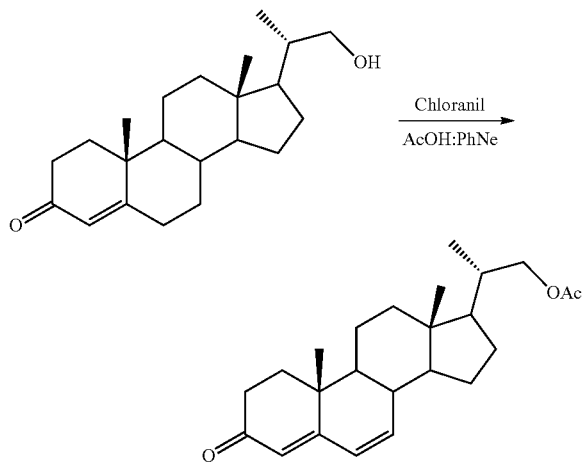

HMPO (300 g, 0.913 mol) was charged to a reaction vessel, followed by AcOH (0.9 L) and toluene (0.3 L) with stirring. p-Chloranil (245 g, 1.00 mol) was then charged and the reaction mixture heated to 110° C. and maintained at this temperature for 6 h. The mixture was then cooled to 5° C. and held at that temperature for 2 h. The resulting solid was filtered and the filter-cake washed with cold, premixed 3:1 AcOH:Toluene (4×150 mL) and the filtrate was concentrated in-vacuo. The residue was dissolved in acetone (900 mL), then 3.5% w/w aqueous NaOH (3.0 L) was charged dropwise with stirring, maintaining the temperature below 30° C. The resulting solids were collected by filtration and the filter cake was washed with premixed 1:1 acetone:water (1.5 L). The filter cake was then slurried in 1:1 acetone:water (600 mL) at 20° C., filtered and washed with premixed 1:1 acetone:water (1.0 L). The solid was dried under vacuum at 65-70° C. to give the desired product (224 g, 67%) as a tan solid. δH (400 MHz, CDCl$_3$); 6.17-6.12 (1H, m, C6-CH), 6.10 (1H, dd, J 9.9, 2.0, C7-CH), 5.68 (1H, s, C4-CH), 4.10 (1H, dd, J 10.7, 3.5, C22-CH$_a$H$_b$), 3.79 (1H, dd, J 10.7, 7.4, C22-CH$_a$H$_b$), 2.58 (1H, ddd, J 17.9, 14.4, 5.4, C2-CH$_a$H$_b$), 2.49-2.39 (1H, m, C2-CH$_a$H$_b$), 2.20 (1H, brt, J 10.2, C8-CH), 2.10-1.97 (1H, m), 2.06 (3H, s, OC(O)CH$_3$), 1.96-1.66 (4H, m), 1.62-1.53 (1H, m), 1.52-1.16 (8H, m), 1.12 (3H, s, C19-CH$_3$), 1.04 (3H, d, J 6.6, C21-CH$_3$), 0.79 (3H, s, C18-CH$_3$); δC (100 MHz, CDCl$_3$); 199.6, 171.3, 163.8, 141.2, 127.9, 123.6, 69.4, 53.2, 52.6, 50.7, 43.6, 39.4, 37.7, 36.1, 35.8, 33.9, 33.9, 27.6, 23.8, 21.0, 20.7, 17.1, 16.3, 11.9.

C. Synthesis of (20S)-20-hydroxymethyl-pregna-4,6-dien-3-one

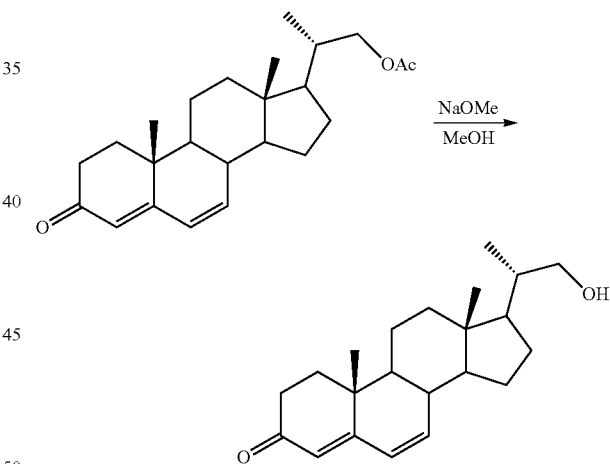

(20S)-20-Acetoxymethyl-pregna-4,6-dien-3-one (25 g, 67.5 mmol) was suspended in MeOH (250 mL) and sodium methoxide (25% w/v solution in MeOH) was added until pH 12 was achieved. The resulting mixture was stirred at room temperature for 4 h. The pH was adjusted to pH 4 by addition of Finex CS08GH$^+$ resin. The mixture was filtered and the filtrate was concentrated under reduced pressure, co-evaporating with PhMe (2×250 mL). The residue was dried in a vacuum oven at 30° C. for 48 h to give the desired product (22.15 g, 99%) as a light brown solid. δH (400 MHz, CDCl$_3$); 6.16-6.11 (1H, m, C7-CH), 6.09 (1H, dd, J 9.9, 2.3, C6-CH), 5.67 (1H, s, C4-CH), 3.65 (1H, dd, J 10.5, 3.3, C22-CH$_a$H$_b$), 3.59 (1H, dd, J 10.5, 6.7, C22-CH$_a$H$_b$), 2.57 (1H, ddd, J 18.0, 14.4, 5.5, C2-CH$_a$H$_b$), 2.45-2.38 (1H, m, C2-CH$_a$H$_b$), 2.19 (1H, brt, J 10.4, C8-CH), 2.11-1.76 (5H, m), 1.71 (1H, td, J 13.9, 5.3, C1-CH$_a$H$_b$), 1.65-1.16 (9H, m), 1.11 (3H, s, C19-CH$_3$), 1.06 (3H, d, J 6.6, C21-CH$_3$), 0.78 (3H, s, C18-CH$_3$); δC (100 MHz, CDCl$_3$); 199.7, 164.0, 141.4, 127.9, 123.5, 67.8, 53.2, 52.3, 50.7, 43.5, 39.4, 38.7, 37.8, 36.1, 33.9, 33.9, 27.6, 23.8, 20.7, 16.7, 16.3, 12.0;

D. Synthesis of (20S)-20-tertbutyldimethylsilyloxymethyl-pregna-4,6-dien-3-one

E. Synthesis of (20S)-20-formyl-pregna-4,6-dien-3-one

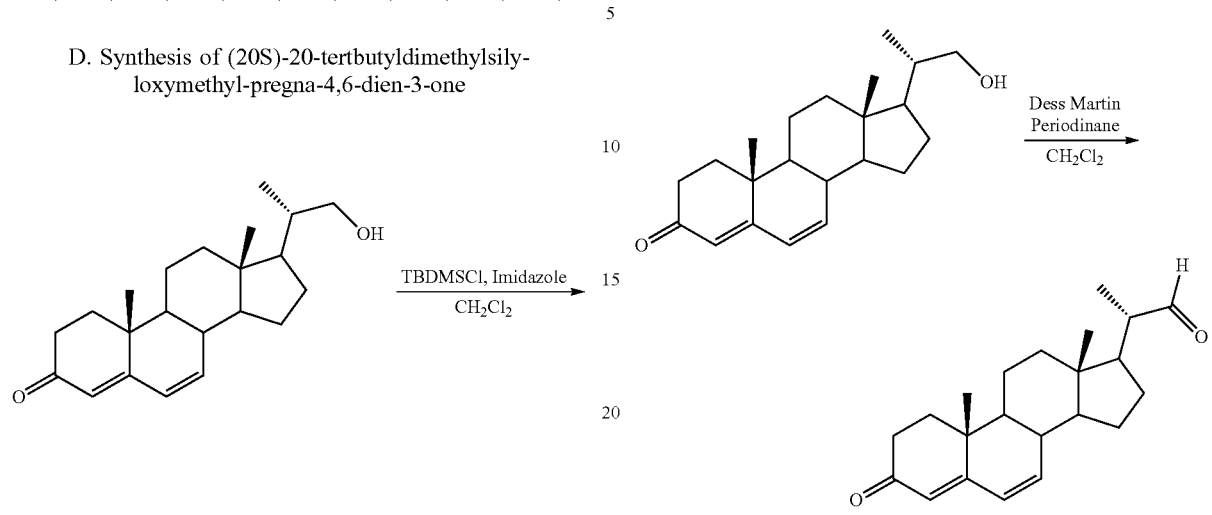

(20S)-20-Hydroxymethyl-pregna-4,6-dien-3-one (1.00 g, 3.04 mmol) was dissolved in anhydrous CH$_2$Cl$_2$ (10 mL) and the solution was cooled to 0° C. Imidazole (414 mg, 6.09 mmol) and TBDMSCl (551 mg, 3.65 mmol) were added and the reaction was stirred at 0° C. for 4 h. The reaction was warmed to room temperature and CH$_2$Cl$_2$ (10 mL) and water (20 mL) were added. The layers were separated and the organic phase was washed with water (20 mL), saturated aqueous sodium chloride (20 mL), dried over sodium sulfate and was concentrated under reduced pressure. The residue was purified by column chromatography on silica gel (0-25% EtOAc in heptane) to give the desired product (890 mg, 66%) as a light yellow solid. δH (400 MHz, CDCl$_3$); 6.14 (1H, dd, J 9.9, 1.3, C7-CH), 6.09 (1H, dd, J 9.8, 2.4, C6-CH), 5.66 (1H, s, C4-CH), 3.58 (1H, dd, J 9.7, 3.4, C22-CH$_a$H$_b$), 3.28 (1H, dd, J 9.7, 7.2, C22-CH$_a$H$_b$), 2.57 (1H, ddd, J 17.9, 14.4, 5.4, C2-CH$_a$H$_b$), 2.47-2.37 (1H, m, C2-CH$_a$H$_b$), 2.19 (1H, brt, J 10.3, C8-CH), 2.07 (1H, dt, J 12.9, 3.3), 2.00 (1H, dd, J 8.5, 2.1), 1.94-1.63 (3H, m), 1.60-1.15 (9H, m), 1.11 (3H, s, C19-CH$_3$), 1.00 (3H, d, J 6.7, C21-CH$_3$), 0.89 (9H, s, SiC(CH$_3$)$_3$), 0.77 (3H, s, C18-CH$_3$), 0.03 (6H, s, Si(CH$_3$)$_2$); δC (100 MHz, CDCl$_3$); 199.6, 163.9, 141.5, 127.8, 123.5, 67.7, 53.2, 52.5, 50.7, 43.5, 39.4, 39.0, 37.8, 36.1, 34.0, 33.9, 27.6, 25.9, 25.9, 25.9, 23.9, 20.7, 18.4, 16.9, 16.3, 12.0, −5.3, −5.4; (IR) ν$_{max}$(cm$^{-1}$): 3027, 2956, 2930, 2891, 2857, 1677, 1077, 753; HRMS (ESI-TOF) m/z: (M+H)$^+$ calculated for C$_{28}$H$_{46}$O$_2$Si 442.3267, found 443.3338.

(20S)-20-Hydroxymethyl-pregna-4,6-dien-3-one (3.01 g, 9.16 mmol) was dissolved in anhydrous CH$_2$Cl$_2$ (60 ml) and the solution was cooled to 0° C. Dess-Martin periodinane (5.83 g, 13.7 mmol) was added portion-wise over 10 minutes and the reaction was allowed to slowly warm to room temperature and was stirred for 22 h. The mixture was cooled to 0° C. and a 1:1 mixture of 10% aq. Na$_2$S$_2$O$_3$ and 2% aq. NaHCO$_3$ (75 ml) was added portionwise. CH$_2$Cl$_2$ (50 mL) was added and the layers were separated. The aqueous phase was extracted with CH$_2$Cl$_2$ (2×50 mL) and the combined organics were dried over sodium sulfate and concentrated under reduced pressure. The residue was purified by column chromatography on silica gel (0-25% EtOAc in heptane) to give the desired product (1.23 g, 41%) as a pale yellow solid. δH (400 MHz, CDCl$_3$); 9.59 (1H, d, J 3.2, CHO), 6.12 (2H, s, C6-CH and C7-CH), 5.68 (1H, s, C4-CH), 2.58 (1H, ddd, J 17.9, 14.4, 5.4), 2.49-2.36 (2H, m), 2.22 (1H, t, J 10.6, C8-CH), 2.08-1.81 (4H, m), 1.73 (1H, td, J 13.8, 5.1, C1-CH$_a$H$_b$), 1.65-1.20 (8H, m), 1.15 (3H, d, J 6.9, C21-CH$_3$), 1.13 (3H, s, C19-CH$_3$), 0.82 (3H, d, C18-CH$_3$); δC (100 MHz, CDCl$_3$); 204.6, 199.5, 163.6, 140.8, 128.1, 123.7, 52.8, 50.8, 50.7, 49.4, 44.0, 39.2, 37.6, 36.0, 33.9, 33.9, 27.0, 24.1, 20.6, 16.3, 13.5, 12.3; (IR) ν$_{max}$ (cm$^{-1}$): 3030, 2934, 2706, 1717, 1655, 1615, 15811; HRMS (ESI-TOF) m/z: (M+H)$^+$ calculated for C$_{22}$H$_{30}$O$_2$ 326.2246; found 327.2318.

F. Synthesis of (20S)-20-(ethylenedioxymethyl)-pregna-4,6-dien-3-one

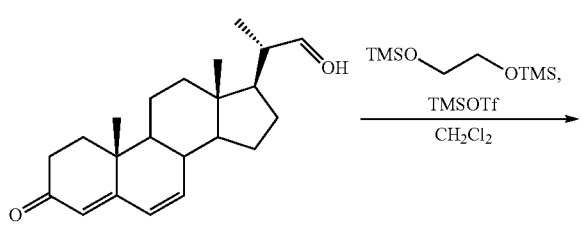

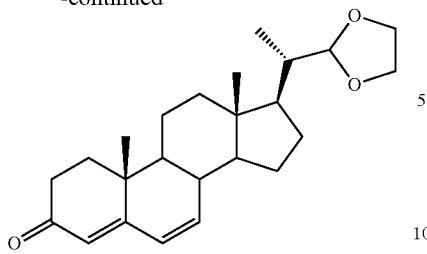

To a solution of (20S)-20-formyl-pregna-4,6-dien-3-one (3.89 g, 12 mmol) in CH$_2$Cl$_2$ (5 vol, 20 mL) under an argon atmosphere was added 1,2-bis (trimethylsilyloxy) ethane (2.94 mL, 12 mmol). The reaction mixture was cooled to −78° C. and TMSOTf (108 µL, 0.6 mmol) was added. After 2 h the reaction mixture was diluted with CH$_2$Cl$_2$ (100 mL) and washed with water (2×100 mL) and 5% aq. NaCl (100 mL). The organic phase was dried over Na$_2$SO$_4$ and was concentrated under reduced pressure. Purification by column chromatography on silica gel gave the desired product (2.42 g, 55%) as a colourless crystalline solid. δH (700 MHz, CDCl$_3$); 6.12 (2H, m), 5.67 (1H, m), 4.86 (1H, d, J 2.0), 3.94 (2H, m), 3.86 (2H, m), 2.56 (1H, m), 2.43 (1H, m), 2.19 (1H, t, J 10.6), 2.05-1.95 (3H, m), 1.85 to 1.20 (12H, m), 1.11 (3H, s), 0.95 (3H, d, J=6.7), 0.77 (3H, s). δC (176 MHz, CDCl$_3$); 199.7, 163.9, 141.4, 127.9, 123.6, 105.6, 65.3, 65.1, 52.9, 52.2, 50.6, 43.7, 39.3, 39.3, 37.8, 36.1, 34.0, 33.9, 27.3, 23.9, 20.67, 16.3, 11.7, 11.6.

G. Synthesis of (20S)-20-(1-aminomethyl)-pregna-4,6-dien-3-one

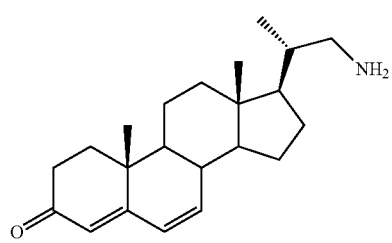 [SMILES: C[C@H](CN)[C@H]1CCC2C3C=CC4=CC(=O)CC[C@]4(C)C3CC[C@@]21C]

(i) Synthesis of (20S)-tosyloxymethyl-pregna-4,6-dien-3-one

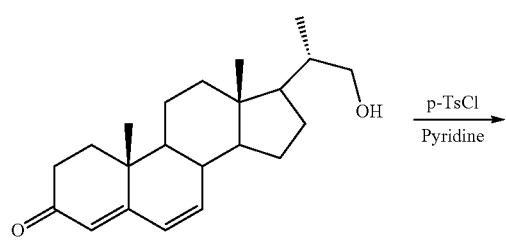

To a solution of (20S)-hydroxymethyl-pregna-4,6-dien-3-one (1.50 g, 4.58 mmol) in pyridine (50 mL) at 0° C. was added p-toluenesulfonyl chloride (1.79 g, 9.39 mmol). The reaction was stirred at 0° C. for 1 h and ambient for 17 h. The reaction was quenched with 1 M aq. HCl (75 mL) and was diluted with ethyl acetate (150 mL). The organic phase was separated and washed with water (50 mL), 5% aq. sodium bicarbonate (75 mL), 5% aq. NaCl (50 mL) and was concentrated in vacuo. The residue was purified by column chromatography on silica gel (heptane-EtOAc) to give the desired product (1.59 g, 72%) as a yellow powder. R$_f$: 0.36 (3:2, heptane:ethyl acetate); $^1$H NMR (700 MHz, CDCl$_3$): δ=7.78 (2H, d, J 8.2, Ar—H), 7.35 (2H, d, J 8.2, Ar—H), 6.10 (2H, br. s, C6H and C7H), 5.67 (1H, s, C4H), 3.97 (1H, dd, J 9.3, 3.2, C22H), 3.80 (1H, dd, J 9.3, 6.4, C22H), 2.56 (1H, ddd, J 17.6, 14.6, 5.6, C2H), 2.45-2.41 (4H, m, C2H and Ts-CH$_3$), 2.17 (1H, t, J 10.5), 2.01-1.96 (2H, m), 1.80-1.67 (4H, m), 1.54 (1H, dq, J 13.5, 3.1), 1.41 (1H, qd, J 13.1, 3.9), 1.30-1.23 (3H, m), 1.23-1.17 (3H, m), 1.10 (3H, s, C19H), 1.00 (3H, d, J 6.7, C21H), 0.73 (3H, s, C18H). $^{13}$C NMR (176 MHz, CDCl$_3$): δ=197.9, 162.0, 142.9, 139.2, 131.3, 128.0, 126.2, 126.1, 121.9, 73.6, 51.3, 49.9, 48.8, 41.7, 37.4, 35.9, 34.4, 34.3, 32.2, 32.1, 25.6, 21.9, 20.0, 18.8, 15.1, 14.5, 10.1.

(ii) Synthesis of (20S)-azidomethyl-pregna-4,6-dien-3-one

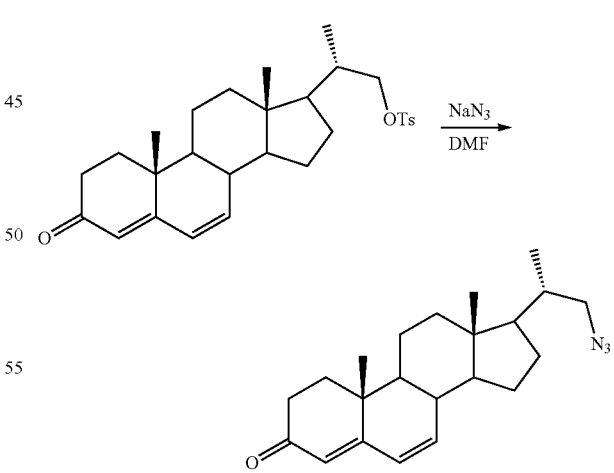

To a suspension of (20S)-tosyloxymethyl-pregna-4,6-dien-3-one (1.58 g, 3.27 mmol) in DMF (24 mL) and water (59 µL) was added sodium azide (273 mg, 4.20 mmol). The reaction was heated to 70° C. and stirred for 1 h. The reaction was quenched with 2% aq. sodium bicarbonate solution (50 mL) at 40° C., and was diluted with ethyl acetate (100 mL). The layers were separated and the organic layer was washed with 2% aq. sodium bicarbonate (50 mL), 5% aq. NaCl (50 mL) and was concentrated in vacuo. The residue was purified by column chromatography on silica gel (heptane-EtOAc) to give the desired product (1.01 g, 91% yield) as a colourless crystalline solid. $R_f$: 0.54 (3:2, heptane:ethyl acetate); $^1$H NMR (700 MHz, CDCl$_3$): δ=6.12 (1H, d, J 9.9, C6H), 6.10 (1H, dd, J 9.9, 2.1, C7H), 5.67 (1H, s, C4H), 3.38 (1H, dd, J 11.9, 3.3, C22H), 3.07 (1H, dd, J 11.9, 7.3, C22H), 2.57 (1H, ddd, J 17.8, 14.7, 5.4, C2H), 2.46-2.41 (1H, m, C2H), 2.17 (1H, t, J 10.6), 2.04 (1H, dt, J 12.8, 3.3), 2.00 (1H, ddd, J 13.2, 5.4, 2.1), 1.93-1.86 (1H, m), 1.86-1.81 (1H, m), 1.75-1.65 (2H, m), 1.56 (1H, dq, J 13.4, 3.7), 1.44 (1H, qd, J 13.0, 4.0), 1.40-1.28 (6H, m), 1.11 (3H, s, C19H), 1.06 (3H, d, J 6.7, C21H), 0.77 (3H, s, C18H). $^{13}$C NMR (176 MHz, CDCl$_3$): δ=199.9, 163.8, 141.1, 128.0, 123.6, 57.9, 53.2, 53.0, 50.6, 43.6, 39.3, 37.7, 36.9, 36.0, 34.0, 33.9, 27.8, 23.8, 20.6, 17.8, 16.3, 12.0.

(iii) Synthesis of (20S)-aminomethyl-pregna-4,6-dien-3-one

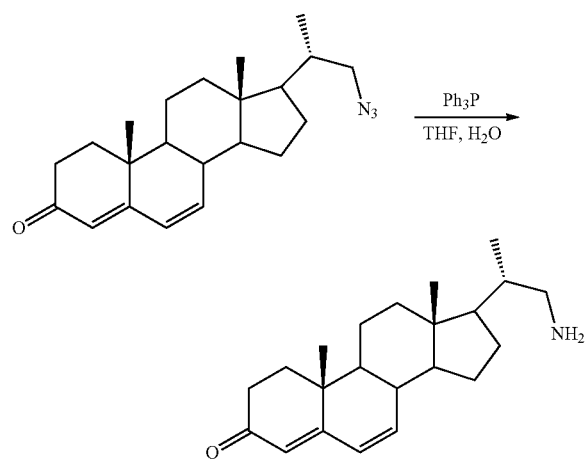

To a solution of (20S)-azidomethyl-pregna-4,6-dien-3-one (99 mg, 0.29 mmol) and triphenylphosphine (106 mg, 0.40 mmol) in THF (1.1 mL) under an argon atmosphere, acetone (300 μL) was added. The reaction mixture was stirred at 18° C. for 64 h. The reaction mixture was diluted with EtOAc (10 mL) and aq. hydrochloric acid solution (10 mL, 2M). The aq. phase was basified with aq. sodium hydroxide solution (6.5 mL, 2M) to pH 11, and extracted with EtOAc (10 mL). The organic phase was separated and concentrated in vacuo. The residue was purified by flash chromatography on silica gel to afford (20S)-aminomethyl-pregna-4,6-dien-3-one as an off-white powder (28 mg, 30% yield), $R_f$ 0.23 (4:1, CH$_2$Cl$_2$:MeOH); $^1$H NMR (700 MHz, CDCl$_3$): δ=6.12-6.07 (2H, m, C6H and C7H), 5.67 (1H, s, C4H), 3.05 (1H, dd, J 12.7, 3.1, C22H$_a$H$_b$), 2.74 (1H, dd, J 12.7, 8.3, C22H$_a$H$_b$), 2.58 (1H, ddd, J 17.9, 14.5, 5.4, C2H$_a$H$_b$), 2.46-2.41 (1H, m, C2H$_a$H$_b$), 2.18 (1H, t, J 10.5), 2.05-1.94 (3H, m), 1.90-1.81 (2H, m), 1.68 (1H, td, J 13.9, 5.6), 1.55 (1H, dq, J 13.4, 3.4), 1.45-1.17 (9H, m), 1.20 (3H, obscured d, J 6.7, C21H), 1.11 (3H, s, C18H), 0.78 (3H, s, C19H). $^{13}$C NMR (140 MHz, CDCl$_3$): δ=199.5, 163.6, 140.8, 128.0, 123.7, 53.2, 52.8, 50.6, 45.3, 43.6, 39.3, 37.6, 36.0, 36.0, 35.1, 34.0, 33.9, 27.8, 23.7, 20.7, 17.3, 16.3.

H. Synthesis of (20S)-20-(1-mesyloxymethyl)-pregna-4,6-dien-3-one

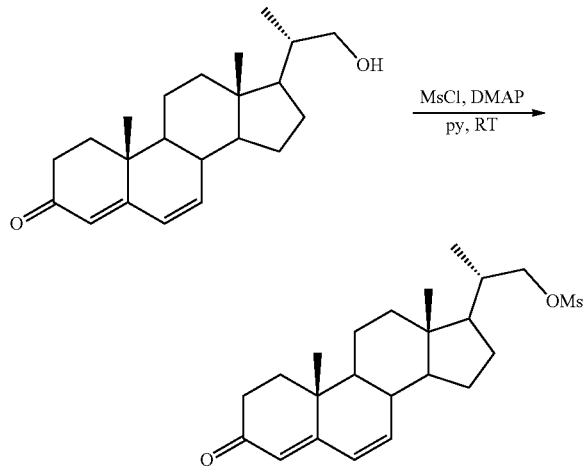

To a solution of (20S)-20-hydroxymethyl-pregna-4,6-dien-3-one (1.00 g, 3.05 mmol) in pyridine (10 mL) was added DMAP (19 mg, 0.15 mmol). MsCl (1.18 mL, 15.2 mmol) was added dropwise and the reaction was stirred at room temperature for 18 h. The reaction was cooled in an ice bath and water (10 mL) was added dropwise. EtOAc (20 mL) was added and the layers were separated. The aqueous layer was extracted with EtOAc (3×20 mL). The combined organic phases were washed with 2 M aq. HCl (20 mL), dried over sodium sulfate and were concentrated under reduced pressure. The residue was purified by column chromatography on silica gel (0-50% EtOAc in heptane) to give the desired product (1.01 g, 82%) as an orange solid. δH (400 MHz, CDCl$_3$); 6.12 (2H, brs, C6-CH and C7-CH), 5.68 (1H, s, C4-CH), 4.21 (1H, dd, J 9.4, 3.2, C22-CH$_a$H$_b$), 4.01 (1H, dd, J 9.4, 6.6, C22-CH$_a$H$_b$), 3.01 (3H, s, OS(O$_2$)CH$_3$), 2.58 (1H, ddd, J 18.0, 14.4, 5.5, C2-CH$_a$H$_b$), 2.49-2.39 (1H, m, C2-CH$_a$H$_b$), 2.21 (1H, brt, J 10.5, C8-CH), 2.09-1.80 (5H, m), 1.73 (1H, td, J 13.8, 5.2, C1-CH$_a$H$_b$), 1.63-1.53 (1H, m), 1.52-1.18 (7H, m), 1.13 (3H, s, C19-CH$_3$), 1.12 (3H, d, J 6.1, C21-CH$_3$), 0.80 (3H, s, C18-CH$_3$); δC (100 MHz, CDCl$_3$); 199.5, 163.6, 140.9, 128.0, 123.7, 74.8, 53.1, 51.8, 50.6, 43.6, 39.3, 37.7, 37.2, 36.3, 36.0, 33.9, 33.9, 27.5, 23.8, 20.6, 16.9, 16.3, 12.0.

I. Synthesis of (20R)-20-(1-cyanomethyl)-pregna-4,6-dien-3-one

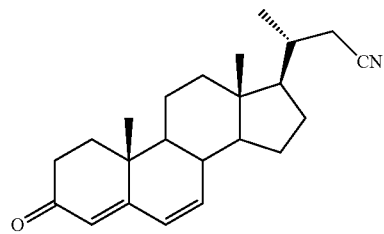 [SMILES: C[C@H](CC#N)[C@H]1CCC2C3C=CC4=CC(=O)CC[C@]4(C)C3CC[C@@]21C]

(i) Synthesis of (20S)-20-bromomethyl-4-pregnen-3-one

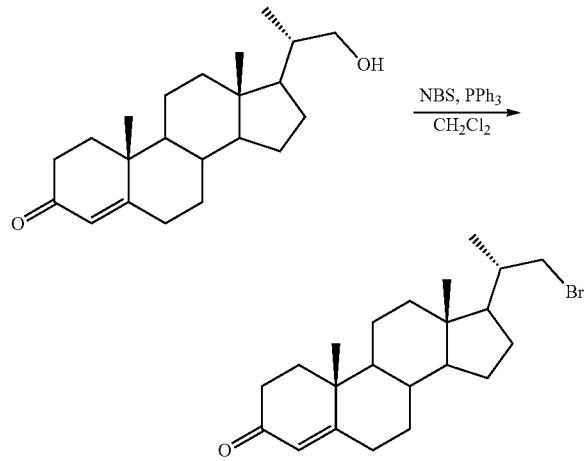

To a solution of (20S)-hydroxymethyl-4-pregnen-3-one (50 g, 0.15 mol) in $CH_2Cl_2$ (350 mL) at 0° C. was added triphenylphosphine (43.6 g, 0.17 mol). N-bromosuccinimide (29.6 g, 0.17 mol) was added portionwise and the reaction mixture was stirred at 18° C. After 18 h, the reaction mixture was cooled to 0° C. and triphenylphosphine (19.8 g, 0.08 mol) was added, followed by N-bromosuccinimide (13.5 g, 0.08 mol) portionwise. The mixture was warmed to 18° C. After 2 h the reaction mixture was washed with water (350 mL) and the aqueous phase extracted with $CH_2Cl_2$ (350 mL). The combined organic phases were washed with 5% aq. sodium bicarbonate (350 mL), and the aqueous phase extracted with $CH_2Cl_2$ (100 mL). The combined organic phases were washed with 5% aq. sodium chloride (150 mL), dried over sodium sulfate and were concentrated in vacuo. The residue was purified by column chromatography on silica gel (heptane-EtOAc) to give the desired product (47.1 g, 79%) as a yellow solid. $^1H$ NMR (700 MHz, $CDCl_3$): δ=5.72 (1H, s), 3.50 (1H, dd, J=9.8, 2.7, C22-$CH_aH_b$), 3.35 (1H, dd, J=9.8, 5.9, C22-$CH_aH_b$), 2.45-2.32 (3H, m), 2.27 (1H, ddd, J=14.6, 4.1, 2.5), 2.04-1.98 (2H, m), 1.91-1.82 (2H, m), 1.72-1.64 (3H, m), 1.56-1.50 (2H, m), 1.43 (1H, qd, J=13.1, 4.1), 1.33-1.27 (2H, m), 1.22 (1H, dd, J=13.0, 4.2), 1.20-1.13 (1H, m), 1.18 (3H, s), 1.09 (3H, d, J=6.4), 1.09-1.00 (2H, m), 0.94 (1H, ddd, J=12.3, 10.9, 4.1), 0.74 (3H, s); $^{13}C$ NMR (176 MHz, $CDCl_3$): δ=197.5, 169.3, 121.8, 53.5, 51.6, 51.6, 41.4, 40.4, 37.3, 36.5, 35.7, 33.6, 33.6, 31.9, 30.8, 29.9, 25.5, 22.0, 18.9, 16.6, 15.3, 10.3.

(ii) Synthesis of (20R)-cyanomethyl-4-pregnen-3-one

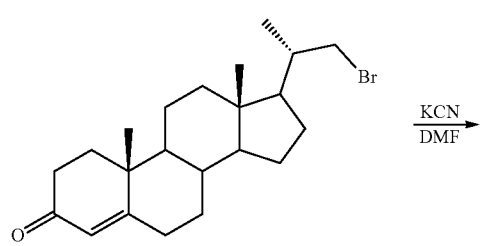

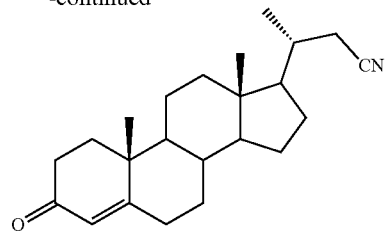

To a suspension of (20S)-20-bromomethyl-4-pregnen-3-one (15 g, 38.1 mmol) in DMF (225 mL) was added potassium cyanide (7.5 g, 114 mmol). The suspension was stirred at 80° C. for 41 h before cooling to room temperature. EtOAc (250 mL) and water (500 mL) were added and the layers were separated. The aqueous layer was extracted with EtOAc (2×250 mL) and the combined organic phases were washed with 5% aq. NaCl (250 mL) and were concentrated under reduced pressure. The residue was purified by column chromatography on silica gel (heptane/EtOAc) to afford the desired product (9.7 g, 75%) as a white solid. δH (700 MHz, $CDCl_3$); 5.73 (1H, s, C4-CH), 2.45-2.32 (4H, m), 2.27 (1H, ddd, J=14.6, 4.2, 2.7), 2.24 (1H, dd, J=16.8, 7.1), 2.04-1.99 (2H, m), 1.89-1.78 (3H, m), 1.72-1.65 (2H, m), 1.57-1.51 (2H, m), 1.43 (1H, qd, J=13.2, 4.0), 1.31-1.16 (4H, m), 1.18 (3H, s), 1.17 (3H, d, J=6.7), 1.11-1.01 (2H, m), 0.94 (1H, ddd, J=12.3, 10.7, 4.1), 0.74 (3H, s); δC (176 MHz, $CDCl_3$); 199.5, 171.2, 123.9, 118.9, 55.7, 54.7, 53.6, 42.5, 39.2, 38.5, 35.7, 35.6, 34.0, 33.6, 32.8, 31.9, 28.0, 24.8, 24.1, 20.9, 19.3, 17.4, 12.1.

(iii) Synthesis of (20R)-cyanomethyl-4,6-pregnadien-3-one

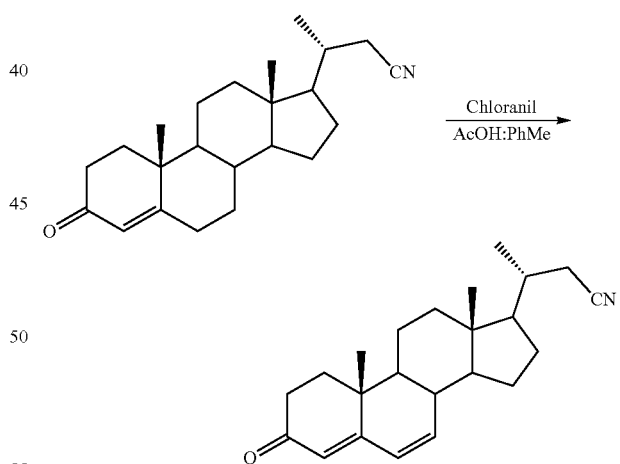

To a suspension of (20R)-cyanomethyl-4-pregnen-3-one (9.1 g, 26.8 mmol) in toluene (36 mL) and acetic acid (0.15 mL) was added p-chloranil (7.2 g, 39.5 mmol). The mixture was heated at reflux for 90 minutes before allowing to cool to room temperature. The suspension was filtered, washing with toluene (25 mL). The filtrate was concentrated under reduced pressure and the residue was purified by column chromatography on silica gel (heptane/EtOAc). The material was then dissolved in acetone (35 mL) and methanol (23 mL) and 0.5 M aq. NaOH (200 mL) was added dropwise. Water (100 mL) was added and the resulting solid was filtered, washing with water (2×50 mL) and 2:1 acetone:water (2×20 mL). The solid was dried in vacuo to afford the desired product (5.4 g, 60%) as a pale brown solid. δH (700 MHz, CDCl₃); 6.11 (2H, s), 5.67 (1H, s), 2.57 (1H, ddd, J=18.0, 14.4, 5.4), 2.45-2.42 (1H, m), 2.37 (1H, dd, J=16.7, 3.7), 2.25 (1H, dd, J=16.7, 7.2), 2.01 (1H, t, J=10.4), 2.03 (1H, dt, J=12.8, 3.3), 2.00 (1H, ddd, J=13.2, 5.4, 2.1), 1.96-1.91 (1H, m), 1.88-1.81 (1H, m), 1.74-1.70 (1H, m), 1.58 (1H, dq, J=13.4, 3.6), 1.44 (1H, qd, J=4.4, 3.9), 1.36-1.20 (7H, m), 1.18 (3H, d, J=6.7), 1.11 (3H, s), 0.79 (3H, s); δC (176 MHz, CDCl₃); 199.6, 163.67, 140.8, 128.1, 123.7, 118.8, 54.6, 53.2, 50.5, 43.5, 39.1, 37.6, 36.0, 33.9, 33.9, 33.5, 28.0, 24.8, 23.6, 20.6, 19.3, 16.3, 12.0.

J. Synthesis of (20S)-20-(1-bromomethyl)-pregna-4,6-dien-3-one

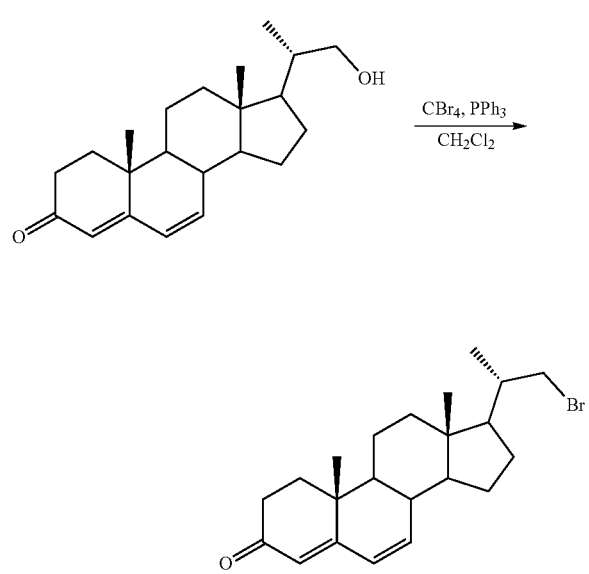

To a solution of (20S)-20-hydroxymethyl-pregna-4,6-dien-3-one (1.00 g, 3.05 mmol) in anhydrous CH₂Cl₂ (10 mL) was added carbon tetrabromide (1.52 g, 4.57 mmol). Triphenylphosphine (1.20 g, 4.57 mmol) was added and the mixture was heated at reflux for 2 h. The reaction was allowed to cool to room temperature and water (20 mL) was added. The layers were separated and the organic layer was washed with 5% aq. NaHCO₃ (20 mL), 10% aq NaCl (20 mL) and was concentrated under reduced pressure. The residue was purified by column chromatography on silica gel (0-25% acetone in heptane) to give the desired product (980 mg, 82%) as a light yellow crystalline solid. δH (400 MHz, CDCl₃); 6.09-6.00 (2H, m, C6-CH and C7 CH), 5.59 (1H, s, C4-CH), 3.43 (1H, dd, J 9.8, 2.7, C22-CH$_a$H$_b$), 3.29 (1H, dd, J 9.8, 5.8, C22-CH$_a$H$_b$), 2.50 (1H, ddd, J 17.9, 14.4, 5.4, C2-CH$_a$H$_b$), 2.40-2.30 (1H, m, C2-CH$_a$H$_b$), 2.13 (1H, brt, J 9.8, C8-CH), 2.01-1.57 (5H, m), 1.55-1.45 (1H, m), 1.44-1.10 (8H, m), 1.05 (3H, s, C19-CH₃), 1.03 (3H, d, J 6.5, C21-CH₃), 0.72 (3H, s, C18-CH₃); δC (100 MHz, CDCl₃); 199.2, 163.6, 141.0, 127.9, 123.6, 53.5, 53.1, 50.6, 43.4, 43.3, 39.2, 37.7, 37.6, 36.0, 33.9, 33.9, 27.4, 23.6, 20.6, 18.6, 16.3, 12.3.

K. Synthesis of 23-ethoxyformyl-3-oxo-4,6-choladien-24-oic Acid Ethyl Ester

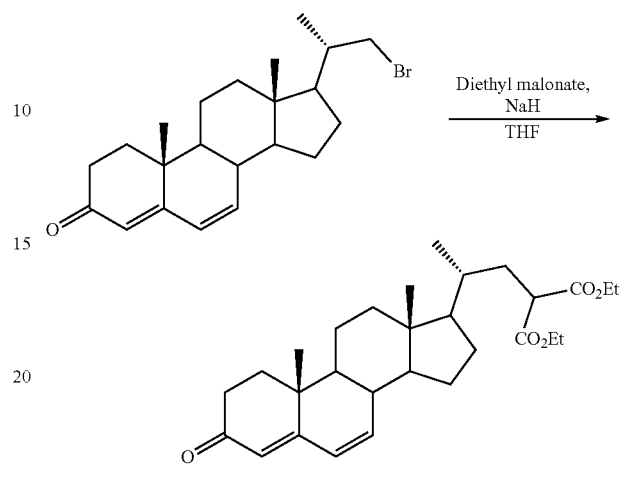

Sodium hydride (60% dispersion in mineral oil, 226 mg, 5.64 mmol) was suspended in anhydrous THF (10 mL) and the mixture was cooled to 0° C. Diethyl malonate (1.17 mL, 7.68 mmol) was added drop-wise and the mixture was stirred at 0° C. for 15 minutes. A solution of (20S)-20-(bromomethyl)-pregna-4,6-dien-3-one (1.00 g, 2.56 mmol) in anhydrous THF (10 mL) was added drop-wise and the reaction was heated at reflux for 18 h. The reaction was allowed to cool to room temperature and water (10 mL) was added. EtOAc (25 mL) was added and the layers were separated. The aqueous layer was extracted with EtOAc (3×50 mL) and the combined organics were washed with 10% aq. NaCl (50 mL), dried over sodium sulfate and were concentrated under reduced pressure. The residue was purified by column chromatography on silica gel (0-25% acetone in heptane) to give the desired product (1.00 g, 83%) as a clear oil. δH (400 MHz, CDCl₃); 6.17-6.07 (2H, m, C6-CH and C7-CH), 5.67 (1H, s, C4-CH), 4.29-4.14 (4H, m, 2×C(O)OCH₂), 3.44 (1H, dd, J 10.9, 3.7, EtO₂CCH), 2.57 (1H, ddd, J 17.9, 14.4, 5.4, C2-CH$_a$H$_b$), 2.43 (1H, dddd, J 17.8, 5.1, 2.0, 0.8, C2-CH$_a$H$_b$), 2.24-2.12 (2H, m), 2.10-1.93 (3H, m), 1.87-1.77 (1H, m), 1.71 (1H, td, J 16.2, 5.2, C1-CH$_a$H$_b$), 1.59-1.35 (4H, m), 1.34-1.14 (12H, m), 1.11 (3H, s, C18-CH₃), 0.96 (3H, d, J 6.2, C21-CH₃), 0.75 (3H, s, C19-CH₃); δC (100 MHz, CDCl₃); 199.5, 170.0, 169.6, 163.8, 141.3, 127.9, 123.6, 61.4, 61.2, 56.2, 53.4, 50.6, 49.8, 43.5, 39.5, 37.7, 36.1, 35.0, 34.3, 34.0, 33.9, 28.0, 23.7, 20.7, 18.2, 16.3, 14.2, 14.1, 11.9.

L. Synthesis of (20S)-20-(5-Tosyltetrazol-1-yl) methyl-pregna-4,6-dien-3-one

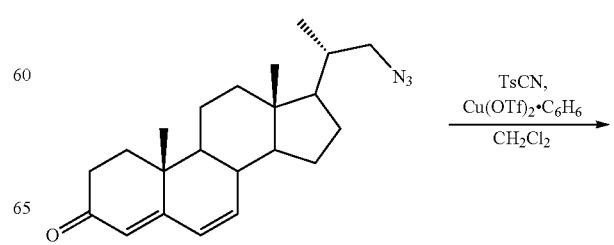

-continued

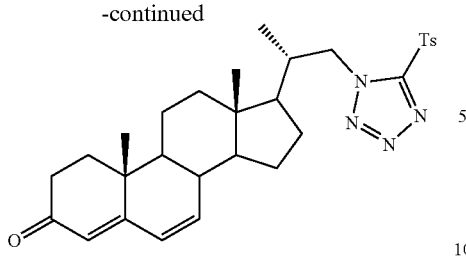

To a solution of (20S)-azidomethyl-pregna-4,6-dien-3-one (500 mg, 1.41 mmol) in CH₂Cl₂ (5 mL) was added p-toluenesulfonyl cyanide (282 mg, 1.55 mmol). Copper(I) trifluoromethanesulfonate benzene complex (71 mg, 0.141 mmol) was added and the mixture was stirred at room temperature for 18 h. Toluene (5 mL), added p-toluenesulfonyl cyanide (128 mg, 0.708 mmol) and copper(I) trifluoromethanesulfonate benzene complex (71 mg, 0.141 mmol) were added and the mixture was heated to 60° C. for 24 h. Water (10 mL) and CH₂Cl₂ (30 mL) were added and the layers were separated. The organic layer was washed with 10% aq. Na₂S₂O₃/2% aq. NaHCO₃ (2×20 mL), 10% aq. NaCl (20 mL), was dried over sodium sulfate and was concentrated under reduced pressure. The residue was purified by column chromatography on silica gel (0-50% EtOAc in heptane) to give the desired product (381 mg, 50%) as a light yellow solid. δH (400 MHz, CDCl₃); 8.03-7.97 (2H, m, ArH), 7.46 (2H, m, ArH), 6.14 (2H, brs, C6-CH and C7-CH), 5.69 (1H, s, C4-CH), 4.80 (1H, dd, J 13.4, 3.9, C22-CH$_a$H$_b$), 4.45 (1H, dd, J 13.4, 10.5, C22-CH$_a$H$_b$), 2.26-2.53 (1H, m), 2.51 (3H, s, ArCH₃), 2.49-2.28 (2H, m), 2.24 (1H, appt, J, 10.5), 2.13-1.97 (2H, m), 1.96-1.87 (1H, m), 1.79-1.63 (2H, m), 1.53-1.18 (8H, m), 1.13 (3H, s, C19-CH₃), 0.89 (3H, d, J 6.6, C21-CH₃), 0.86 (3H, s, C18-CH₃); δC (100 MHz, CDCl₃); 199.5, 163.6, 147.5, 140.8, 134.3, 130.4, 129.3, 128.1, 123.7, 55.1, 53.9, 53.2, 50.7, 44.0, 39.4, 37.8, 37.6, 36.0, 33.9, 33.9, 31.9, 27.5, 23.8, 22.7, 21.9, 20.6, 16.5, 16.3, 12.0.

M. Synthesis of N-((22E)-3,24-dioxo-4,6,22-cholatrien-24-yl)cyclopropyl Sulfonamide (i) Synthesis of (22E)-3-Oxo-4,6,22-cholatrien-24-oic Acid

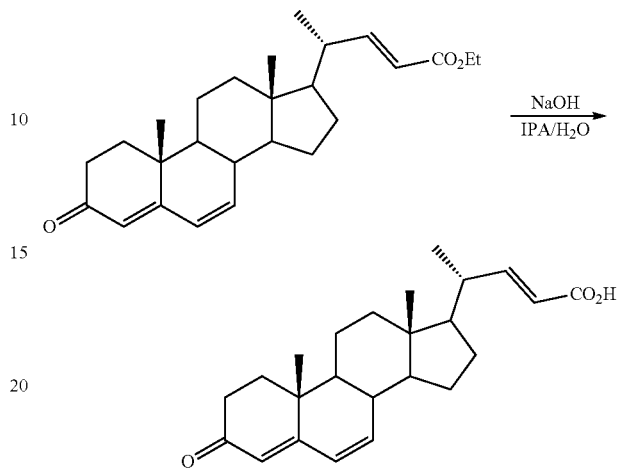

(22E)-3-Oxo-4,6,22-cholatrien-24-oic acid ethyl ester (10 g, 25.2 mmol) was suspended in IPA (100 mL) and the mixture was heated to 60° C. 0.5 M aq. NaOH (60 mL, 30 mmol) was added and the mixture was stirred at 60° C. for 3 h. The volatiles were removed under reduced pressure and EtOAc (250 mL) was added. The mixture was acidified to pH 1 using 2 M aq. HCl, and further EtOAc (100 mL) was added. The layers were separated and the organic layer was washed with water (3×100 mL) and concentrated under reduced pressure. The residue was dissolved in EtOAc (200 mL) with heating and was then cooled to −20° C. for 18 h. The solid formed was filtered, washing with EtOAc (20 mL). The solid was then dried under reduced pressure to give the desired product (4.55 g, 49%) as a tan solid. δH (400 MHz, CDCl₃); 6.94 (1H, dd, J 15.6, 9.0, C23-CH), 6.11 (2H, brs, C6-CH and C7-CH), 5.77 (1H, dd, J 15.6, 0.6, C22-CH), 5.68 (1H, s, C4-CH), 2.58 (1H, ddd, J 18.0, 14.4, 5.4, C2-CH$_a$H$_b$), 2.51-2.40 (1H, m, C2-CH$_a$H$_b$), 2.40-2.28 (1H, m), 2.21 (1H, appt, J 10.1), 2.10-1.95 (2H, m), 1.89-1.65 (3H, m), 1.64-1.53 (1H, m), 1.53-1.39 (1H, m), 1.38-1.18 (7H, m), 1.12 (3H, s, C19-CH₃), 1.12 (3H, d, J 6.6, C21-CH₃), 0.81 (3H, s, C18-CH₃); δC (100 MHz, CDCl₃); 199.7, 171.8, 163.9, 156.9, 141.1, 128.0, 123.6, 118.6, 54.7, 53.2, 50.7, 43.7, 39.7, 39.3, 37.7, 36.1, 33.9, 33.9, 27.8, 23.7, 20.6, 19.1, 16.3, 12.1.

(ii) Synthesis of N-((22E)-3,24-dioxo-4,6,22-cholatrien-24-yl)cyclopropylsulfonamide

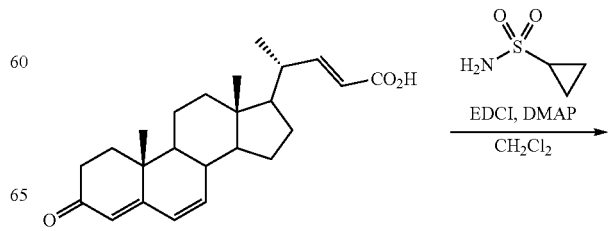

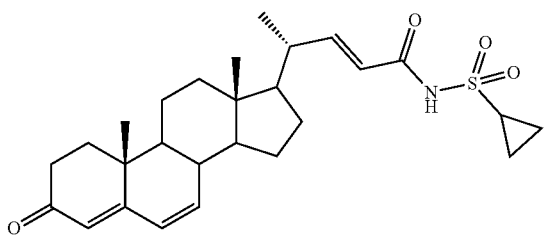

To a solution of (22E)-3-oxo-4,6,22-cholatrien-24-oic acid (2.00 g, 5.43 mmol) in CH$_2$Cl$_2$ (40 mL) was added EDCI (1.69 g, 10.9 mmol) and DMAP (1.33 g, 10.9 mmol). Cyclopropane sulfonamide (1.97 g, 16.3 mmol) was added and the reaction was stirred at room temperature for 22 h. Water (25 mL) was added and the layers were separated. The aqueous layer was extracted with CH$_2$Cl$_2$ (2×25 mL) and the combined organics were washed with 2 M aq HCl (20 mL), 10% aq. NaCl (10 mL), dried over sodium sulfate and concentrated under reduced pressure. The residue was purified by column chromatography on silica gel (0-10% acetone in toluene) to give the desired product (1.68 g, 66%) as an off-white solid. δH (400 MHz, CDCl$_3$); 8.90 (1H, s, NH), 6.95 (1H, dd, J 15.5, 9.0, C23-CH), 6.11 (2H, brs, C6-CH and C7-CH), 5.86 (1H, dd, J 15.5, 0.5, C22-CH), 5.68 (1H, s, C4-CH), 3.00 (1H, dddd, J 12.8, 9.5, 8.1, 4.8, SO$_2$CH), 2.64 (1H, ddd, J 18.1, 14.4, 5.4, C2-CH$_a$H$_b$), 2.51-2.41 (1H, m, C2-CH$_a$H$_b$), 2.40-2.28 (1H, m), 2.25-2.15 (1H, m), 2.09-1.96 (2H, m), 1.85-1.64 (3H, m), 1.63-1.52 (1H, m), 1.51-1.17 (9H, m), 1.17-1.07 (5H, m), 1.12 (3H, s, C19-CH$_3$), 0.80 (3H, s, C18-CH$_3$); δC (100 MHz, CDCl$_3$); 200.0, 164.2, 164.1, 155.5, 141.3, 127.9, 123.6, 119.4, 54.7, 53.2, 50.6, 43.8, 39.8, 39.3, 37.8, 36.1, 33.9, 33.9, 31.5, 28.1, 23.7, 20.6, 19.1, 16.3, 12.2, 6.3, 6.3.

N. Synthesis of N-((22E)-3,24-dioxo-4,6,22-cholatrien-24-yl)-4-(trifluoromethoxy)benzenesulfonamide

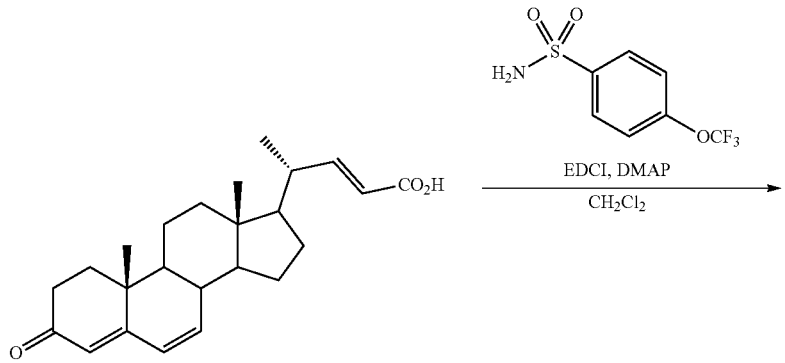

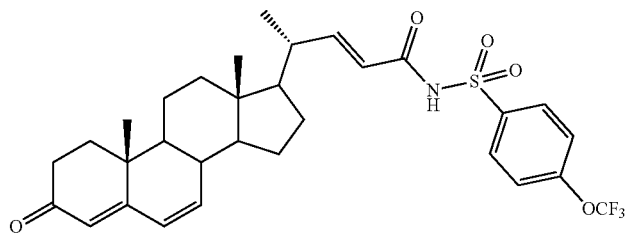

To a solution of (22E)-3-oxo-4,6,22-cholatrien-24-oic acid (2.00 g, 5.43 mmol) in $CH_2Cl_2$ (40 mL) was added EDCI (1.69 g, 10.9 mmol) and DMAP (1.33 g, 10.9 mmol). 4-(Trifluoromethoxy)benzene sulfonamide (3.93 g, 16.3 mmol) was added and the reaction was stirred at room temperature for 22 h. Water (25 mL) was added and the layers were separated. The aqueous layer was extracted with $CH_2Cl_2$ (2×25 mL) and the combined organics were washed with 2 M aq HCl (20 mL), 10% aq. NaCl (10 mL), dried over sodium sulfate and concentrated under reduced pressure. The residue was used in the next step without purification. A portion was purified by column chromatography on silica gel (0-50% EtOAc in heptane) to give the desired product as an off-white solid. δH (400 MHz, MeOD); 8.16-8.11 (2H, m, ArH), 7.52-7.46 (2H, m, ArH), 6.82 (1H, dd, J 15.4, 9.0, C23-CH), 6.20 (1H, brdd, J 9.8, 1.4, C6-CH), 6.15 (1H, dd, J 9.9, 1.4, C7-CH), 5.82 (1H, dd, J 15.4, 0.7, C22-CH), 5.64 (1H, s, C4-CH), 2.62 (1H, ddd, J 18.2, 14.5, 5.4, C2-$CH_aH_b$), 2.42-2.20 (3H, m), 2.12-1.98 (2H, m), 1.88-1.63 (3H, m), 1.63-1.55 (1H, m), 1.49 (1H, dd, J 12.6, 3.8), 1.40-1.18 (7H, m), 1.14 (3H, s, C19-$CH_3$), 1.08 (3H, d, J 6.6, C21-$CH_3$), 0.81 (3H, s, C18-$CH_3$); δC (100 MHz, MeOD); 202.3, 167.2, 165.9, 156.7, 154.0, 143.3, 139.7, 131.8, 128.8, 123.9, 123.0 (q, J 254), 121.9, 120.6, 56.0, 54.6, 52.2, 44.9, 40.9, 40.6, 39.1, 37.4, 35.0, 34.7, 30.2, 29.0, 24.7, 21.7, 19.5, 16.6, 12.5.

O. Synthesis of (20S)—(N-benzyl)aminomethyl-pregna-4,6-dien-3-one

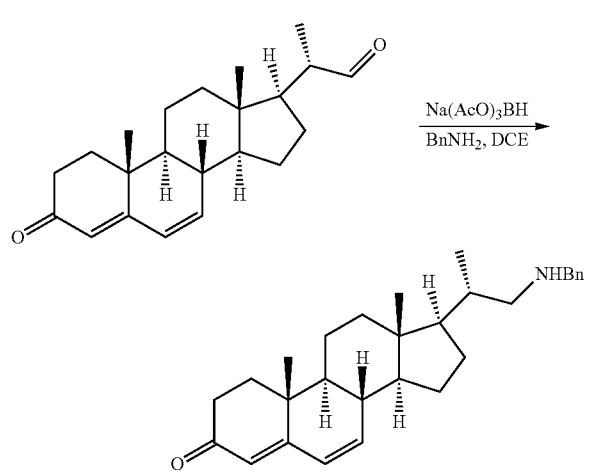

(20S)-Formyl-pregna-4,6-dien-3-one (98 mg, 0.30 mmol) and benzylamine (21 µL, 0.30 mmol) were dissolved in 1,2-dichloroethane (1.0 mL) under an argon atmosphere. Sodium triacetoxyborohydride (96 mg, 0.45 mmol) was added. The reaction mixture was stirred at 20° C. for 2 h, then quenched with aq. sodium bicarbonate solution (5%, 2 mL). The mixture was diluted with EtOAc (10 mL) and water (5 mL). The aq. phase was separated and extracted with EtOAc (2×5 mL). The organic phases were combined and concentrated in vacuo. The residue was purified by silica column chromatography (heptane-EtOAc) to yield (20S)—(N-benzyl)aminomethyl-pregna-4,6-dien-3-one as a beige powder (51 mg, 41% yield). $R_f$ 0.15 (EtOAc); $^1$H NMR (500 MHz, $CDCl_3$): δ=7.34 (4H, d, J 4.5, Bn-CH), 7.29-7.23 (1H, m, Bn-CH), 6.15 (1H, d, J 10.2, C6), 6.11 (1H, dd, J 9.6, 2.0, C7H), 5.68 (1H, s, C4H), 3.84 (1H, d, J 13.1, Bn-$CH_aH_b$), 3.75 (1H, d, J 13.1, Bn-$CH_aH_b$), 2.69 (1H, dd, J 11.6, 3.0, C22$H_aH_b$), 2.58 (1H, ddd, J 17.2, 14.5, 5.3, C2$H_aH_b$), 2.44 (1H, dd, J 17.4, 4.4, C2$H_aH_b$), 2.35 (1H, dd, J 11.5, 8.3, C22$H_aH_b$), 2.20 (1H, t, J 10.7, H8), 2.07 (1H, dt, J 12.6, 3.0), 2.04-1.97 (1H, m, C1$H_aH_b$), 1.92-1.68 (3H, m), 1.68-1.60 (1H, m, C20H), 1.60-1.52 (1H, m), 1.44 (1H, qd, J 12.8, 3.9), 1.40-1.18 (7H, m), 1.13 (3H, s, C18H), 1.04 (3H, d, J 6.6, C21H), 0.78 (3H, s, C19H). $^{13}$C NMR (126 MHz, $CDCl_3$): δ=199.7, 164.0, 141.4, 140.5, 128.4, 128.1, 127.8, 126.9, 123.5, 54.9, 54.2, 54.0, 53.3, 50.7, 43.5, 39.5, 37.7, 36.5, 36.0, 34.0, 33.9, 27.9, 23.8, 20.7, 17.8, 16.3, 12.0.

Example 2—Preparation of Compounds of General formula (IA)

A. Epoxidation of (22E)-3-oxo-4,6,22-cholatrien-24-oic Acid Ethyl Ester Using Methyltrioxorhenium to Form (6α, 7α, 22E)-6,7-epoxy-3-oxo-4,22-chola-dien-24-oic Acid Ethyl Ester

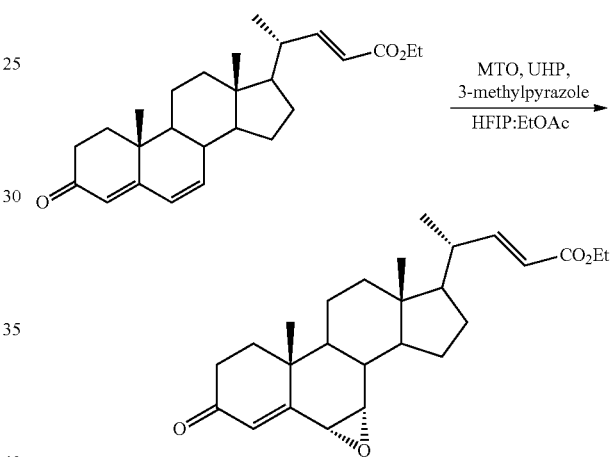

To a solution of (22E)-3-oxo-4,6,22-cholatrien-24-oic acid ethyl ester (5.00 g, 12.6 mmol) in HFIP (20 mL, 4 volumes) and EtOAc (10 mL, 2 volumes) was added MTO (37 mg, 0.126 mmol) and 3-methylpyrazole (122 µl, 1.51 mmol) and the mixture was cooled to 5° C. UHP (1.30 g, 13.9 mmol) was added portion-wise and the mixture was stirred at 5° C. for 24 h. After 24 h, a second addition of MTO (37 mg, 0.126 mmol) and UHP (1.30 g, 13.9 mmol) was conducted and the reaction was stirred at 5° C. for 18 h. The reaction was then quenched by the portion-wise addition of 12% aq. $NaHSO_3$ (15 mL) maintaining the temperature <25° C. The mixture stirred for 0.5 h whilst warming to ambient temperature, to ensure all peroxide was quenched. Water (12.5 mL) and EtOAc (5 mL) were added and the layers separated. The organic phase was washed with 5% aq. $NaHCO_3$ (20 mL), water (20 mL) and then concentrated under reduced pressure. The crude material (5.72 g) was crystallised from EtOAc (15 mL).

Further Epoxidation Reactions of Compounds of Formula (II)

General Procedure A: MTO Catalyzed Epoxidation

To a solution of a compound of general formula (II) (1 eq.) and MTO (1 mol %) in EtOAc (2 vol) and HFIP (4 vol) was added 3-methylpyrazole (0.12 eq.) and the mixture was cooled to 5° C. UHP (1.1 eq) was added and the mixture was stirred for 18-50 h until deemed complete by TLC analysis.

The reaction mixture was then quenched with the addition of 12% aq. NaHSO$_3$ (3 vol) then partitioned between water (2.5 vol) and EtOAc (1 vol). The phases were separated and the organic phase washed with 5% aq. NaHCO$_3$ (4 vol) and water (4 vol). After concentration under reduced pressure the crude residue was purified by column chromatography (SiO$_2$, eluting with heptane:EtOAc gradient).

B. Epoxidation of (20S)-20-hydroxymethyl-pregna-4,6-dien-3-one to Form (6α, 7α, 20S)-6,7-epoxy-20-hydroxymethyl-pregn-4-en-3-one

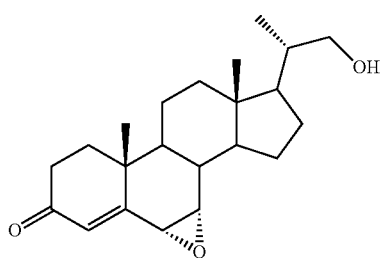

(20S)-20-hydroxymethyl-pregna-4,6-dien-3-one (500 mg, 1.52 mmol) was epoxidized using MTO according to the General Procedure A to yield the title compound (210 mg, 40%) as a light yellow solid.

δH (400 MHz, CDCl$_3$); 6.11 (1H, s, C4-CH), 3.66 (1H, dd, J 10.4, 3.3, C22-CH$_a$H$_b$), 3.45 (1H, d, J 3.7, C6-CH), 3.42-3.32 (2H, m, C7-CH and C22-CH$_a$H$_b$), 2.56 (1H, ddd, J 18.2, 14.1, 5.5, C2-CH$_a$H$_b$), 2.45 (1H, dddd, J 18.0, 5.3, 2.0, 0.8, C2-CH$_a$H$_b$), 2.02 (1H, dt, J 12.8, 2.7, C12-CH$_a$H$_b$), 1.98-1.83 (4H, m), 1.71 (1H, td, J 13.6, 5.5, C1-CH$_a$H$_b$), 1.65-1.16 (10H, m), 1.10 (3H, s, C19-CH$_3$), 1.06 (3H, d, J 6.6, C21-CH$_3$), 0.77 (3H, s, C18-CH$_3$); δC (100 MHz, CDCl$_3$); 198.3, 162.7, 131.1, 67.8, 54.6, 52.5, 52.5, 51.1, 43.2, 40.6, 39.2, 38.8, 35.6, 34.7, 34.1, 33.9, 27.8, 23.8, 19.9, 17.2, 16.7, 11.9.

C. Epoxidation of (20S)-20-(1-bromomethyl)-pregna-4,6-dien-3-one to Form (6α, 7α, 20S)-20-(1-bromomethyl-6,7-epoxy-pregn-4-en-3-one

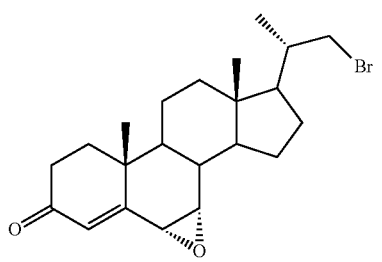 [SMILES: C[C@H](CBr)C1CCC2C3C(CC[C@@]21C)[C@@]1(C)CCC(=O)C=C1[C@H]1O[C@@H]31]

(20S)-20-(1-bromomethyl)-pregna-4,6-dien-3-one (500 mg, 1.28 mmol) was epoxidized using MTO according to General Procedure A to yield the title compound (290 mg, 56%) as a light brown solid.

δH (400 MHz, CDCl$_3$); 6.12 (1H, s, C4-CH), 3.52 (1H, dd, J 9.8, 2.6, C22-CH$_a$H$_b$), 3.46 (1H, d, J 3.7, C6-CH), 3.39-3.17 (2H, m, C7-CH and C22-CH$_a$H$_b$), 2.56 (1H, ddd, J 18.1, 14.0, 5.4, C2-CH$_a$H$_b$), 2.47 (1H, dddd, J 18.0, 5.5, 2.2, 0.9, C2-CH$_a$H$_b$), 2.05-1.84 (5H, m), 1.79-1.66 (2H, m), 1.58-1.46 (1H, m), 1.44-1.19 (7H, m), 1.11 (3H, d, J 6.3, C21-CH$_3$), 1.10 (3H, s, C19-CH$_3$), 0.78 (3H, s, C18-CH$_3$); δC (100 MHz, CDCl$_3$); 198.2, 162.6, 131.2, 54.5, 53.5, 52.5, 51.2, 43.1, 43.0, 40.6, 39.0, 37.8, 35.6, 34.7, 34.1, 33.9, 27.6, 34.6, 19.9, 18.6, 17.2, 12.2.

D. Epoxidation of (20S)-20-(1-mesyloxymethyl)-pregna-4,6-dien-3-one to Form (6α, 7α, 20S)-20-(1-mesyloxymethyl)-6,7-epoxy-pregn-4-en-3-one

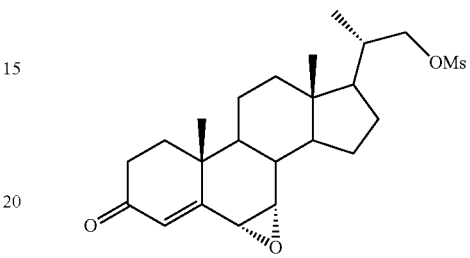

(20S)-20-(1-mesyloxymethyl)-pregna-4,6-dien-3-one (500 mg, 1.24 mmol) was epoxidized using MTO according to General Procedure A to yield the title compound (460 mg, 88%) as a light yellow solid.

δH (400 MHz, CDCl$_3$); 6.12 (1H, s, C4-CH), 4.22 (1H, dd, J 9.4, 3.2, C22-CH$_a$H$_b$), 3.99 (1H, dd, J 9.4, 6.9, C22-CH$_a$H$_b$), 3.46 (1H, brd, J 3.7, C6-CH), 3.34 (1H, brd, J 3.6, C7-CH), 3.01 (3H, s, OS(O$_2$)CH$_3$), 2.56 (1H, ddd, J 18.2, 14.1, 5.5, C2-CH$_a$H$_b$), 2.50-2.41 (1H, m), 2.05-1.80 (6H, m), 1.72 (1H, td, J 13.6, 5.6, C1-CH$_a$H$_b$), 1.65-1.17 (8H, m), 1.11 (3H, d, J 6.5, C21-CH$_3$), 1.10 (3H, C19-CH$_3$), 0.76 (3H, s, C18-CH$_3$); δC (100 MHz, CDCl$_3$); 198.2, 162.5, 131.2, 74.7, 54.5, 52.5, 51.8, 51.1, 43.3, 40.6, 39.1, 37.3, 36.4, 35.6, 34.7, 34.1, 33.9, 27.7, 23.7, 19.9, 17.2, 16.8, 11.9.

E. Epoxidation of (20S)-20-(1-tertbutyldimethylsilyloxymethyl)-pregna-4,6-dien-3-one to form (6α, 7α, 20S)-20-(1-tert-butyldimethylsilyloxymethyl)-6,7-epoxy-pregn-4-en-3-one

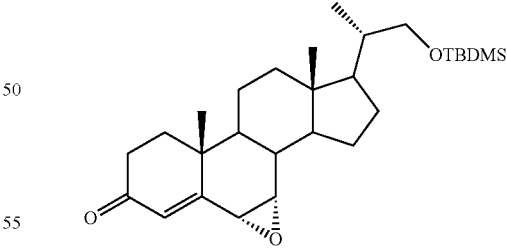

(20S)-20-(1-tertbutyldimethylsilyloxymethyl)-pregna-4,6-dien-3-one (500 mg, 1.13 mmol) was epoxidized using MTO according to General Procedure A to yield the title compound (100 mg, 19%) as a light brown solid.

δH (400 MHz, CDCl$_3$); 6.11 (1H, s, C4-CH), 3.58 (1H, dd, J 9.6, 3.3, C22-CH$_a$H$_b$), 3.45 (1H, d, J 3.7, C6-CH), 3.42 (1H, brd, J 3.5, C7-CH), 3.28 (1H, dd, J 9.6, 7.2, C22-CH$_a$H$_b$), 2.55 (1H, ddd, J 18.2, 14.1, 5.5, C2-CH$_a$H$_b$), 2.49-2.40 (1H, m, C2-CH$_a$H$_b$), 2.02 (1H, td, J 12.8, 3.0, C12-CH$_a$H$_b$), 1.98-1.82 (4H, m), 1.71 (1H, td, J 13.6, 5.5, C1-CH$_a$H$_b$), 1.61-1.14 (9H, m), 1.10 (3H, s, C19-CH$_3$), 1.00 (3H, d, J 6.6, C21-CH$_3$), 0.89 (9H, s, SiC(CH$_3$)$_3$), 0.75 (3H, s, C18-CH$_3$), 0.06 (6H, d, J 0.6, 2×SiCH$_3$); δC (100 MHz, CDCl$_3$); 198.3, 162.8, 131.1, 67.7, 54.7, 52.6, 52.3, 51.1, 43.1, 40.7, 39.2, 39.0, 35.6, 34.7, 34.1, 33.9, 27.8, 26.0, 26.0, 26.0, 23.8, 19.9, 18.4, 17.2, 16.9, 11.9, −5.3, −5.4.

F. Epoxidation of (20S)-20-acetoxymethyl-pregna-4,6-dien-3-one to Form (6α, 7α, 20S)-20-acetoxymethyl-6,7-epoxy-pregn-4-en-3-one

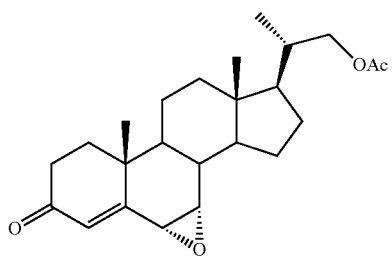 [SMILES: CC(=O)OC[C@@H](C)[C@H]1CCC2C3C(CC[C@@]21C)[C@@]1(C)CCC(=O)C=C1[C@H]1O[C@@H]31]

The product was prepared according to the general procedure for MTO catalysed epoxidation on 200 g scale, isolated in 50% yield (105 g) as a tan solid.

$^1$H NMR (700 MHz, CDCl$_3$): δ=6.11 (1H, s), 4.09 (1H, dd, J 10.7, 3.4), 3.79 (1H, dd, J 10.7, 7.4), 3.45 (1H, d, J 3.7), 3.34 (1H, d, J 3.5), 2.55 (1H, m), 2.46 (1H, m), 2.05 (3H, s), 2.02-1.85 (5H, m), 1.78-1.68 (2H, m), 1.55-1.20 (8H, m), 1.10 (3H, s), 1.02 (3H, d, J 6.6), 0.76 (3H, s); $^{13}$C NMR (175 MHz, CDCl$_3$): δ=198.3, 171.3, 162.7, 131.1, 69.3, 54.6, 52.5, 52.4, 51.1, 43.2, 40.6, 39.1, 35.8, 35.6, 34.6, 34.1, 33.9, 27.7, 23.7, 21.0, 19.9, 17.2, 17.1, 11.8.

G. Epoxidation of (20S)-20-(ethylenedioxymethyl)-pregna-4,6-dien-3-one (Example 1F) to Form (6α, 7α, 20S)-6,7-epoxy-20-(ethylenedioxymethyl)-pregn-4-en-3-one

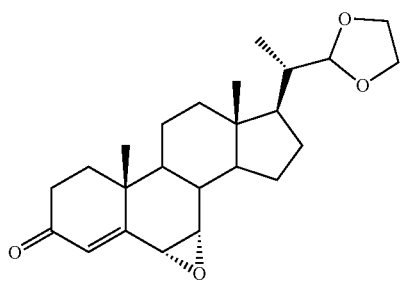 [SMILES: C[C@H](C1OCCO1)[C@H]1CCC2C3C(CC[C@@]21C)[C@@]1(C)CCC(=O)C=C1[C@H]1O[C@@H]31]

(20S)-20-(ethylenedioxymethyl)-pregna-4,6-dien-3-one (3.15 g, 8.5 mmol) and BHT (57 mg, 0.26 mmol) were charged to a flask under argon, followed by EtOAc (8 vol, 25 mL) and water (2.5 vol, 7.9 mL) and the mixture heated to 80° C. mCPBA 70% (3.69 g, 15 mmol) in EtOAc (5 vol, 16 mL) was added dropwise over 10 minutes and the reaction mixture then stirred at 70° C. for 1 h (TLC, eluant 1:1 EtOAc:Heptane; visualized with Cerium Ammonium Molybdate stain). The reaction mixture was allowed to cool to room temperature and washed with 1M aq. NaOH (3×50 mL) and 10% aq. Na$_2$S$_2$O$_3$ (3×50 mL). After a negative test for peroxides the organic phase was dried over Na$_2$SO$_4$ and concentrated in-vacuo at 40° C. Purification by column chromatography and concentration in-vacuo at 40° C. gave (6α, 7α, 20S)-6,7-epoxy-20-(ethylenedioxymethyl)-pregna-4-en-3-one as a white crystalline solid (1.15 g). $^1$H NMR (700 MHz, CDCl$_3$): δ=6.31 (1H, s), 4.85 (1H, d, J 2.0), 4.0-3.8 (2H, m), 3.45 (1H, d, J 3.7), 3.35 (1H, d, J 3.6), 2.59-2.43 (2H, m), 2.05-1.68 (8H, m), 1.55-1.20 (10H, m), 1.10 (3H, s), 0.93 (3H, d, J 6.6), 0.75 (3H, s). $^{13}$C NMR (176 MHz, CDCl$_3$): δ=198.6, 163.0, 131.0, 105.9, 65.2, 65.0, 54.7, 52.5, 51.9, 50.8, 43.4, 40.6, 39.3, 39.0, 35.6, 34.6, 34.1, 33.8, 27.4, 23.8, 19.9, 17.2, 11.6, 11.6.

H. Epoxidation of (20S)-azidomethyl-pregna-4,6-dien-3-one to form (6α, 7α, 20S)-6,7-epoxy-20-azidomethyl-pregna-4-en-3-one

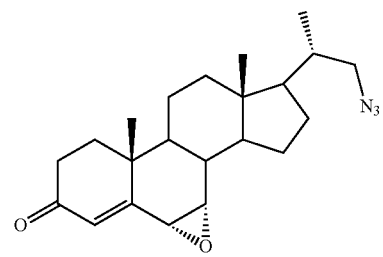 [SMILES: C[C@H](CN=[N+]=[N-])C1CCC2C3C(CC[C@@]21C)[C@@]1(C)CCC(=O)C=C1[C@H]1O[C@@H]31]

To a solution of (20S)-azidomethyl-pregna-4,6-dien-3-one (203 mg, 0.598 mmol) and 3-methylpyrazole (3 μL, 0.04 mmol) in HFIP (0.8 mL) under argon atmosphere at 10° C., MTO (3.2 mg, 0.013 mmol) and UHP (64 mg, 0.68 mmol) were added. The reaction was stirred at 10° C. for 2 h, and quenched with 5% aq. sodium bisulfite solution (1.0 mL). The reaction was diluted with ethyl acetate (10 mL) and washed with water (10 mL) and 10% aq. sodium bicarbonate solution (10 mL). The organic phase was separated and concentrated in vacuo. The residue was purified by column chromatography on silica gel (heptane-EtOAc, R$_f$ in 3:2 heptane:EtOAc=0.42) to the desired product (99 mg, 47%) as a white powder. $^1$H NMR (700 MHz, CDCl$_3$): δ=6.11 (1H, s, C4-CH), 3.46 (1H, d, J=3.7, C6-CH), 3.39 (1H, dd, J=11.9, 3.3, C22-CH$_a$H$_b$), 3.34 (1H, d, J=3.7, C7-CH), 3.06 (1H, dd, J=11.9, 7.5, C22-CH$_a$H$_b$), 2.55 (1H, ddd, J=18.0, 14.3, 5.5, C2-CH$_a$H$_b$), 2.48-2.44 (1H, m, C2-CH$_a$H$_b$), 2.00 (1H, dt, J=11.9, 3.3), 1.97-1.90 (3H, m), 1.87 (1H, td, J=10.8, 1.4, C8-CH), 1.74-1.63 (2H, m), 1.53 (1H, dq, J=12.7, 3.5), 1.49-1.45 (1H, m), 1.41-1.23 (5H, m), 1.22 (1H, td, J=12.7, 3.5), 1.10 (3H, s, C18-CH$_3$), 1.06 (3H, d, J=6.6, C21-CH$_3$), 0.78 (3H, s, C19-CH$_3$). $^{13}$C NMR (140 MHz, CDCl$_3$): δ=198.3, 162.6, 131.1, 57.9, 54.6, 52.9, 52.5, 51.2, 43.2, 40.6, 39.1, 36.9, 35.6, 34.6, 34.1, 33.9, 28.0, 23.7, 19.9, 17.7, 17.2 11.9.

I. Epoxidation of N-((22E)-3,24-dioxo-4,6,22-cholatrien-24-yl)cyclopropyl Sulfonamide to Form N-((6α, 7α, 22E)-3,24-dioxo-6,7-epoxy-4,22-choladien-24-yl)cyclopropylsulfonamide

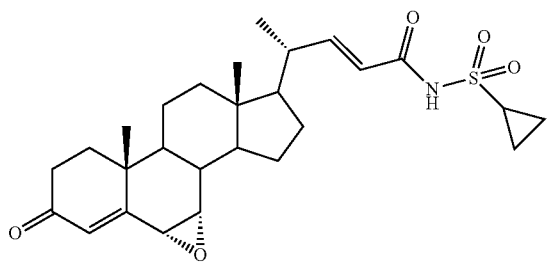 [SMILES: C[C@H](/C=C/C(=O)NS(=O)(=O)C1CC1)C1CCC2C3C(CC[C@@]21C)[C@@]1(C)CCC(=O)C=C1[C@H]1O[C@@H]31]

The product was prepared according to the general procedure for MTO catalysed epoxidation on 1 g scale, isolated in 68% yield (697 mg) as an off white solid.

δH (400 MHz, CDCl$_3$); 8.69 (1H, brs, NH), 6.93 (1H, dd, J 15.4, 9.6, C23-CH), 6.12 (1H, s, C4-CH), 5.83 (1H, m, C22-CH), 3.47 (1H, d, J 14.7, C6-CH), 3.36-3.32 (1H, m, C7-CH), 3.00 (1H, dddd, J 12.8, 9.5, 8.1, 4.8, SO$_2$CH), 2.67-2.40 (2H, m), 2.39-2.27 (1H, m), 2.09-1.64 (7H, m), 1.62-1.18 (11H, m), 1.11 (3H, d, J 6.1, C21-CH$_3$), 1.10 (3H, s, C19-CH$_3$), 0.78 (3H, s, C18-CH$_3$); δC (100 MHz, CDCl$_3$); 198.6, 164.0, 162.8, 156.6, 131.1, 119.3, 54.6, 54.5, 52.6, 51.2, 43.4, 40.6, 39.8, 39.1, 35.6, 34.6, 34.1, 33.9, 31.5, 28.2, 23.7, 19.9, 19.1, 17.2, 12.1, 6.3, 6.3.

J. Epoxidation of N-((22E)-3,24-dioxo-4,6,22-cholatrien-24-yl)-4-(trifluoromethoxy)benzenesulfonamide to Form N-((6α, 7α, 22E)-3,24-dioxo-6,7-epoxy-4,22-choladien-24-yl)-4-(trifluoromethoxy)benzenesulfonamide

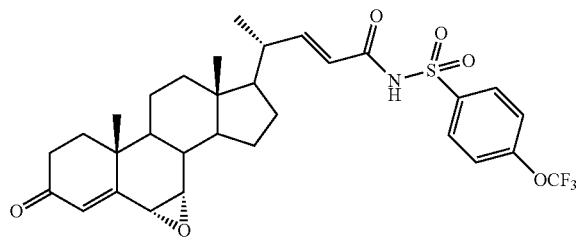 [SMILES: C[C@H](/C=C/C(=O)NS(=O)(=O)c1ccc(OC(F)(F)F)cc1)C1CCC2C3C(CC[C@@]21C)[C@@]1(C)CCC(=O)C=C1[C@H]1O[C@@H]31]

The product was prepared according to the general procedure for MTO catalysed epoxidation on 1 g scale, isolated in 5% yield (50 mg) as a colourless solid.

δH (400 MHz, MeOD); 8.17-8.09 (2H, m, ArH), 7.52-7.46 (2H, m, ArH), 6.82 (1H, dd, J 15.4, 8.9, 3.7, C23-CH), 6.07 (1H, s, C4-CH), 5.84 (1H, dd, J 15.4, 0.7, C22-CH), 3.49 (1H, d, J 3.8, C6-CH), 3.37-3.33 (1H, m, C7-CH), 2.62 (1H, ddd, J 18.2, 14.6, 5.6, C2-CH$_a$H$_b$), 2.44-2.27 (2H, m), 2.08-1.88 (3H, m), 1.85-1.60 (2H, m), 1.60-1.49 (1H, m), 1.48-1.17 (9H, m), 1.12 (3H, s, C19-CH$_3$), 1.07 (3H, d, J 6.6, C21-CH$_3$), 0.80 (3H, s, C18-CH$_3$); δC (100 MHz, MeOD); 201.0, 166.2, 166.1, 156.5, 153.9, 139.8, 131.8, 131.4, 122.0, 121.7 (q, J 256), 120.8, 55.9, 55.7, 53.6, 52.8, 44.6, 42.3, 41.0, 40.5, 36.9, 35.9, 35.2, 35.0, 29.2, 24.6, 21.0, 19.5, 17.3, 12.4.

K. Epoxidation of (20S)-20-(5-Tosyltetrazol-1-yl)methyl-pregna-4,6-dien-3-one to Form (6α, 7α, 20S)-20-(5-Tosyltetrazol-1-yl)methyl-6,7-epoxy-pregna-4-en-3-one

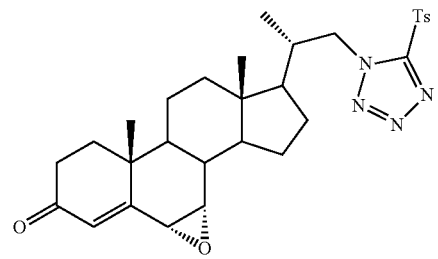 [SMILES: Cc1ccc(S(=O)(=O)c2nnnn2C[C@@H](C)C2CCC3C4C(CC[C@@]32C)[C@@]2(C)CCC(=O)C=C2[C@H]2O[C@@H]42)cc1]

The product was prepared according to the general procedure for MTO catalysed epoxidation on 300 mg scale, isolated in 33% yield (103 mg) as a colourless solid.

δH (400 MHz, CDCl$_3$); 8.00-7.94 (2H, m, ArH), 7.47-7.41 (2H, m, ArH), 6.10 (1H, s, C4-CH), 4.77 (1H, dd, J 13.4, 3.9, C22-CH$_a$H$_b$), 4.42 (1H, dd, J 13.4, 3.9, C22-CH$_a$H$_b$), 3.46 (1H, d, J 3.7, C6-CH), 3.37-3.33 (1H, m, C7-CH), 2.61-2.37 (3H, m), 2.48 (3H, s, ArCH$_3$), 2.37-2.24 (1H, m), 2.11-1.80 (3H, m), 1.76-1.61 (2H, m), 1.58-1.17 (8H, m), 1.09 (3H, s, C19-CH$_3$), 0.85 (3H, d, J 7.0, C21-CH$_3$), 0.81 (3H, s, C18-CH$_3$); δC (100 MHz, CDCl$_3$); 198.2, 162.5, 153.3, 147.5, 134.4, 131.1, 130.4, 129.3, 55.1, 54.5, 53.8, 52.5, 51.2, 43.6, 40.6, 39.1, 37.7, 35.5, 34.6, 34.1, 33.9, 27.6, 23.8, 21.9, 19.9, 17.2, 16.4, 11.9.

Example 3—Preparation of Compounds of General Formula (XXI) Via Compounds of General Formula (I) with Malonate Side Chain The compounds of general formula (II) may be converted to compounds of general formula (IA) as described above and these compounds may then be converted to compounds of general formula (IB), (IC), (ID), (IE) and (IF) by the methods described below. A compound of general formula (IF) may be converted to a compound of general (XXI).

The following illustrates the conversion of a compound of general formula (II) in which —YR$^4$ is CH$_2$OH via compounds of formulae (IA), (IB), (IC), (ID) and (IE) in which —YR$^4$ is —CH$_2$CH[C(O)OMe]$_2$ to a compound of general formula (XXI) in which R$^{4a}$ is C(O)OH is shown in Scheme 4 below.

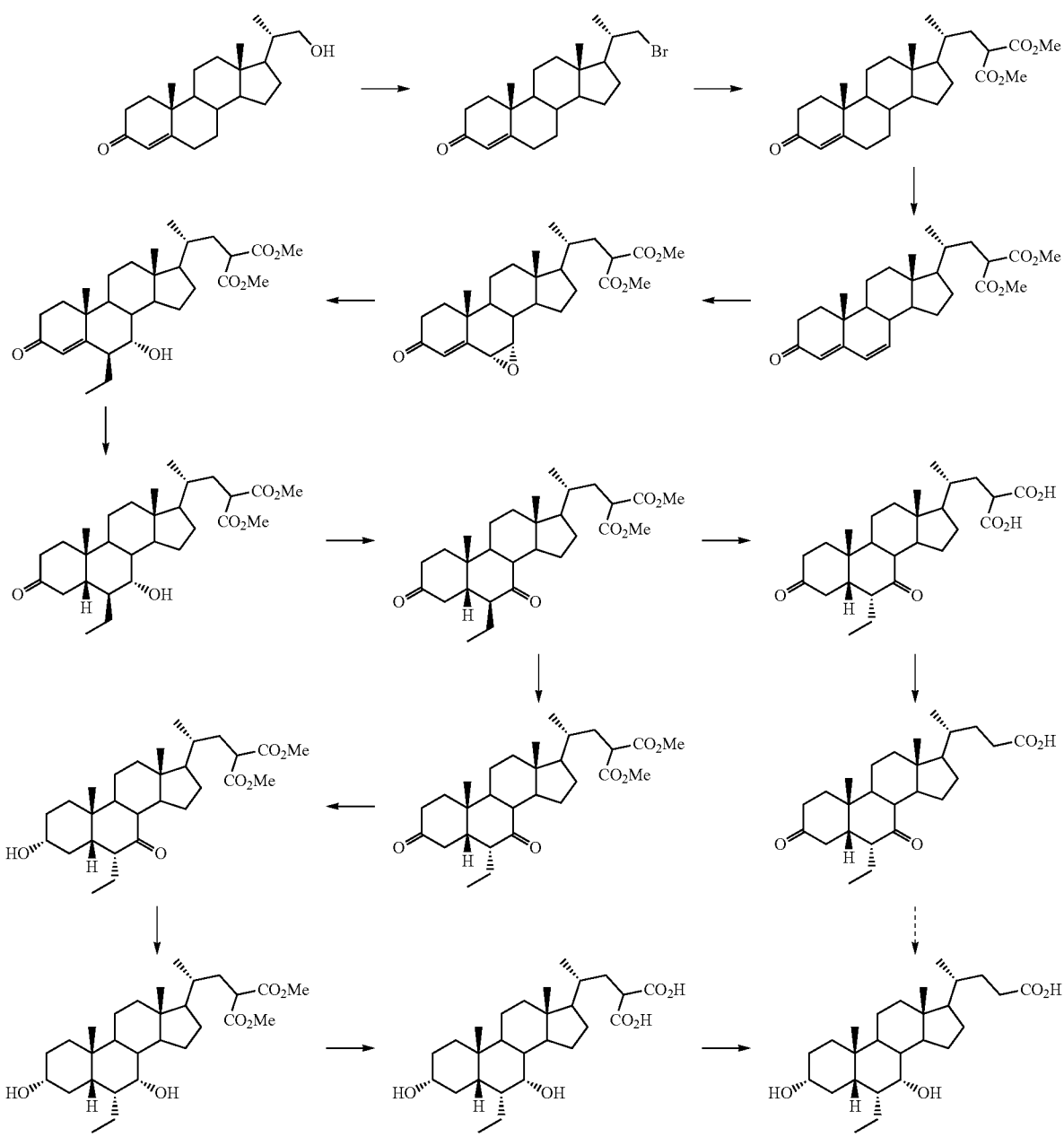
A. Synthesis of 23-carboxy-3-oxo-4-cholen-24-oic Acid Dimethyl Ester
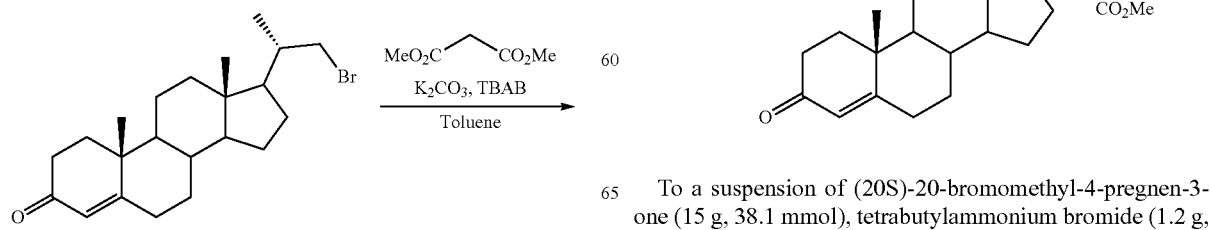
To a suspension of (20S)-20-bromomethyl-4-pregnen-3-one (15 g, 38.1 mmol), tetrabutylammonium bromide (1.2 g, 3.8 mmol) and potassium carbonate (26.3 g, 191 mmol) in toluene (150 mL) was added dimethylmalonate (13.1 mL, 114 mmol) and the reaction mixture was stirred at 80° C. for 91 h. The reaction mixture was then cooled to room temperature and was poured onto water (150 mL). The layers were separated and the aqueous phase was extracted with EtOAc (2×100 mL). The combined organic phases were washed with 5% aq. sodium chloride (100 mL) and were concentrated under reduced pressure. The residue was purified by column chromatography on silica gel (heptane-EtOAc) to give the desired product (14.8 g, 87%) as a yellow solid. $^1$H NMR (700 MHz, CDCl$_3$): δ=5.72 (1H, s), 3.75 (3H, s), 3.72 (3H, s), 3.48 (1H, dd, J=11.0, 4.0), 2.44-2.36 (2H, m), 2.33 (1H, dt, J=17.0, 3.6), 2.27 (1H, ddd, J=14.6, 4.1, 2.4), 2.18 (1H, ddd, J=13.7, 11.1, 2.5), 2.03-2.00 (2H, m), 1.95-1.89 (1H, m), 1.85-1.82 (1H, m), 1.71-1.67 (1H, m), 1.64-1.60 (1H, m), 1.54-1.39 (4H, m), 1.37-1.30 (2H, m), 1.19-1.09 (3H, m), 1.18 (3H, s), 1.05-0.99 (2H, m), 0.94-0.90 (1H, m), 0.93 (3H, d, J=6.5), 0.70 (3H, s); $^{13}$C NMR (176 MHz, CDCl$_3$): δ=199.6, 171.5, 170.4, 170.0, 123.8, 56.3, 55.8, 53.7, 52.6, 52.4, 49.4, 42.5, 39.6, 38.6, 35.7, 35.6, 35.1, 34.3, 34.0, 32.9, 32.0, 28.0, 24.1, 21.0, 18.1, 17.4, 11.9.

B. Synthesis of 23-carboxy-3-oxo-4,6-choladien-24-oic Acid Dimethyl Ester

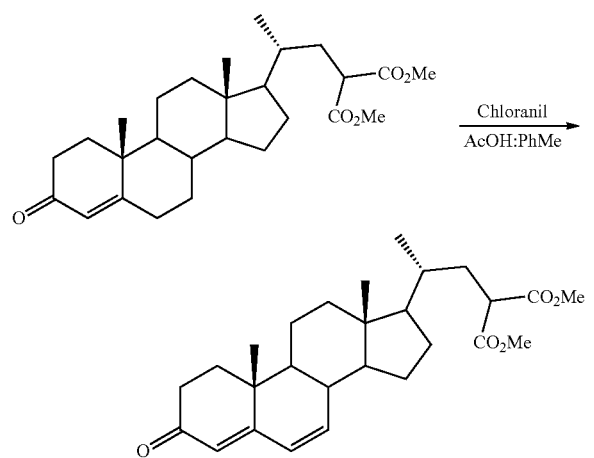

23-Carboxy-3-oxo-4-cholen-24-oic acid dimethyl ester (14.5 g, 32.7 mmol) was suspended in toluene (60 mL) and acetic acid (0.19 mL, 3.3 mmol). p-Chloranil (8.8 g, 35.9 mmol) was added and the mixture stirred at reflux for 65 min. The reaction mixture was cooled to room temperature and filtered. The filter cake was washed with toluene (45 mL) and the filtrate concentrated under reduced pressure. The residue (21.6 g) was used without further purification. A small portion was purified by column chromatography on silica gel (heptane-EtOAc) to give the product. $^1$H NMR (700 MHz, CDCl$_3$): δ=6.12 (1H, d, J=10.8), 6.08 (1H, dd, J=9.8, 2.2), 5.65 (1H, s), 3.74 (3H, s), 3.71 (3H, s), 3.47 (1H, dd, J=11.0, 3.9), 2.58 (1H, dd, J=14.3, 5.3), 2.53 (1H, dd, J=14.3, 5.3), 2.44-2.38 (1H, m), 2.21-2.15 (2H, m), 2.05-1.92 (3H, m), 1.83-1.77 (1H, m), 1.69 (1H, td, J=13.9, 5.2), 1.55-1.34 (5H, m), 1.31-1.11 (5H, m), 1.10 (3H, s), 0.93 (3H, d, J=6.3), 0.73 (3H, s); $^{13}$C NMR (176 MHz, CDCl$_3$): δ=199.6, 170.4, 170.0, 163.9, 141.4, 127.8, 123.5, 56.1, 53.4, 52.6, 52.4, 50.6, 49.4, 43.5, 39.5, 37.7, 36.0, 35.1, 34.3, 33.9, 33.9, 28.0, 23.7, 20.6, 18.1, 16.3, 11.9.

C. Synthesis of (6α, 7α)-6,7-epoxy-3-oxo-4-cholen-23-carboxy-24-oic Acid Dimethyl Ester

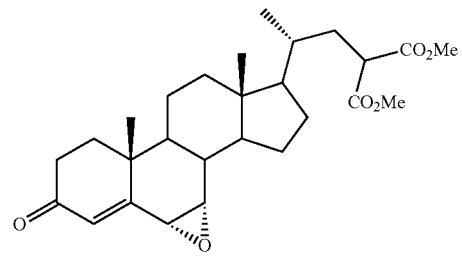 [SMILES: COC(=O)C(C[C@@H](C)C1CCC2C3C(CC[C@@]21C)[C@@]1(C)CCC(=O)C=C1[C@H]1O[C@@H]31)C(=O)OC]

23-Carboxy-3-oxo-4,6-choladien-24-oic acid dimethyl ester (8.94 g, 19.5 mmol) was dissolved in HFIP (35.8 mL) and EtOAc (17.9 mL) and the solution was cooled to 10° C. MTO (51 mg, 0.195 mmol) and 3-methylpyrazole (97 μL, 1.17 mmol) were charged to the solution followed by UHP (2.08 g, 21.4 mmol) in 2 portions over 5 minutes. After 2 h further MTO (51 mg, 0.195 mmol) and 3-methylpyrazole (97 μL, 1.17 mmol) were charged and the solution stirred for 16 h. Further MTO (51 mg, 0.195 mmol), 3 methylpyrazole (97 μL, 1.17 mmol) and UHP (0.38 g, 3.90 mmol) were charged and the solution stirred for 2 h. The reaction was quenched by addition of 5% aq. NaHSO$_3$ (36 mL) over 5 minutes. The phases were separated and the organic phase washed with 5% aq. NaHSO$_3$ until a negative test for peroxides was observed. The organic phase was washed with 5% aq. NaHCO$_3$ (40 mL) and water (40 mL), then dried over sodium sulfate and was concentrated in vacuo. The residue was purified by column chromatography on silica gel to give the desired product (7.07 g, 76%) as a white crystalline solid. $^1$H NMR (700 MHz, CDCl$_3$): δ=6.10 (1H, s), 5.31 (2H, s), 3.75 (3H, s), 3.73 (3H, s), 3.48 (1H, dd, J=11.1, 4.0), 3.45 (1H, d, J=4.0 Hz), 3.34 (1H, d, J=3.6 Hz), 2.55 (1H, ddd, J=18.1, 14.4, 5.6), 2.45 (1H, m), 2.19 (1H, ddd, J=13.6, 11.1, 2.4), 2.05-1.85 (5H, m), 1.70 (1H, td, J=13.9, 5.2), 1.53-1.25 (6H, m), 1.22-1.17 (2H, m), 1.09 (3H, s), 0.49 (3H, d, J=6.5), 0.72 (3H, s); $^{13}$C NMR (176 MHz, CDCl$_3$): δ=198.4, 170.3, 170.0, 162.8, 131.1, 56.0, 54.6, 53.4, 52.6, 52.5, 52.4, 51.3, 49.3, 43.1, 40.6, 39.2, 35.5, 35.1, 34.5, 34.3, 34.1, 33.8, 28.1, 23.6, 19.9, 18.1, 17.2, 11.8.

D. Synthesis of (6β, 7α)-6-ethyl-7-hydroxy-3-oxo-4-cholen-23-carboxy-24-oic Acid Dimethyl Ester

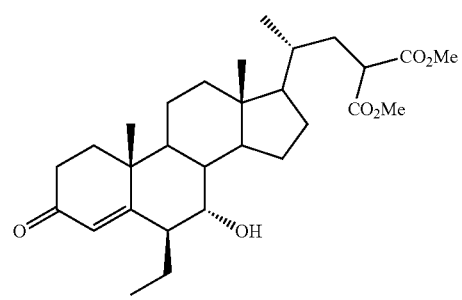 [SMILES: CC[C@H]1C2=CC(=O)CC[C@]2(C)C2CC[C@@]3(C)C(CCC3[C@H](C)CC(C(=O)OC)C(=O)OC)C2[C@@H]1O]

To a solution of 0.5 M ZnCl in THF (15.7 mL, 0.6 eq) in THF (24 mL, 4 vol) under argon at −15° C. was added 1 M EtMgBr in TBME (23.6 mL, 1.8 eq) dropwise over 20 mins. CuCl (65 mg, 0.05 eq) was added in a single portion and the suspension stirred for 10 mins. (6α, 7α)-6,7-epoxy-3-oxo-4-cholanen-23-carboxy-24-oic acid dimethyl ester (6 g) dissolved in THF (24 mL, 4 vol) was added dropwise over 30 mins and the mixture stirred for 90 mins. Sat. aq. NH$_4$Cl (15 mL, 2.5 vol) was added dropwise and the mixture warmed to ambient temperature. The solids were removed by filtration and the filter cake washed with EtOAc (2×25 mL). The filtrate was washed with sat. aq. NH$_4$Cl (2×100 mL) and water (2×100 mL). The organic phase was dried over Na$_2$SO$_4$, filtered, and concentrated in vacuo. Purification by column chromatography afforded (6β, 7α)-6-ethyl-7-hydroxy-3-oxo-4-cholanen-23-carboxy-24-oic acid dimethyl ester as a white crystalline solid (55%).

$^1$H NMR (700 MHz, CDCl$_3$): δ=5.77 (1H, s), 3.75 (3H, s), 3.74 (1H, s), 3.73 (3H, s), 3.48 (1H, dd, J=11.1, 4.0), 2.47 (1H, ddd, J=17.5, 15.0, 5.0), 2.37 (1H, m), 2.31 (1H, m), 2.19 (1H, m), 2.05-1.94 (4H, m), 1.81-1.41 (11H, m), 1.40-1.34 (2H, m), 1.21 (3H, s), 1.20-1.12 (2H, m), 0.93 (3H, d, J=6.4), 0.91 (3H, t, J=7.3), 0.72 (3H, s).

$^{13}$C NMR (176 MHz, CDCl$_3$): δ=199.1, 170.6, 170.4, 170.0, 128.6, 72.2, 56.3, 55.2, 52.6, 52.4, 50.1, 49.4, 44.2, 42.6, 39.1, 38.3, 37.5, 35.6, 35.1, 34.4, 34.1, 28.0, 26.3, 23.6, 20.9, 19.7, 18.1, 12.8, 11.8.

E. Synthesis of (5β, 6β, 7α)-6-ethyl-7-hydroxy-3-oxo-cholan-23-carboxy-24-oic Acid Dimethyl Ester

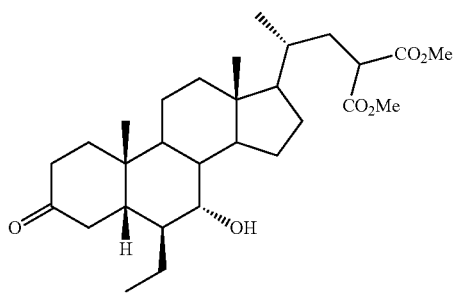 [SMILES: CC[C@@H]1[C@@H](O)C2C3CCC([C@H](C)CC(C(=O)OC)C(=O)OC)[C@@]3(C)CCC2[C@@]2(C)CCC(=O)C[C@@H]12]

A solution of (6β, 7α)-6-ethyl-7-hydroxy-3-oxo-4-cholanen-23-carboxy-24-oic acid dimethyl ester (3.5 g) in DMF (10.5 mL, 3 vol) and MeCN (21 mL, 6 vol) was purged with argon×3 and cooled to −15° C. 5% Pd on CaCO$_3$ was added in one portion and the flask then purged with hydrogen×3 and stirred for 18 h. The flask was purged with argon×3 times and the suspension filtered through a Whatman® GF/B grade filter pad (glass fiber pore size 1 μm) and the cake washed with EtOAc (2×50 mL). The filtrate was washed with water (2×50 mL) and 5% aq. NaCl (50 mL), dried over Na$_2$SO$_4$, filtered and concentrated in vacuo. Purification by column chromatography gave (5β, 6β, 7α)-6-ethyl-7-hydroxy-3-oxo-cholan-23-carboxy-24-oic acid dimethyl ester (1.77 g, 51%).

$^1$H NMR (700 MHz, CDCl$_3$): δ=3.75 (3H, s), 3.73 (3H, s), 3.70 (1H, s), 3.48 (1H, dd, J=11.0, 4.0), 3.35 (1H, dd, J=15.5, 13.6), 2.36 (1H, td, J=14.2, 4.8), 2.19 (1H, m), 2.14-2.08 (2H, m), 2.02-1.90 (4H, m), 1.81 (1H, dd, J=13.3, 4.5), 1.70-1.62 (2H, m), 1.54-1.34 (11H, m), 1.26-1.11 (2H, m), 1.04 (3H, s), 0.95 (3H, d, J=6.4), 0.94 (3H, d, J=7.0), 0.70 (3H, s).

$^{13}$C NMR (176 MHz, CDCl$_3$): δ=213.7, 170.4, 170.1, 72.1, 56.4, 52.6, 52.4, 50.2, 49.8, 49.4, 47.0, 46.7, 42.8, 39.5, 37.7, 36.3, 36.0, 35.7, 35.2, 34.4, 34.1, 28.1, 27.7, 24.4, 23.8, 20.8, 18.2, 13.9, 11.8.

F. Synthesis of (5β, 6β)-6-ethyl-3,7-dioxo-cholan-23-carboxy-24-oic Acid Dimethyl Ester

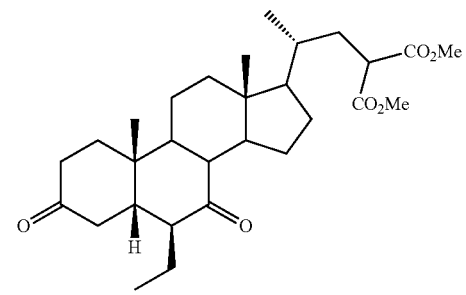 [SMILES: CC[C@@H]1C(=O)C2C3CCC([C@H](C)CC(C(=O)OC)C(=O)OC)[C@@]3(C)CCC2[C@@]2(C)CCC(=O)C[C@@H]12]

To a solution of (5β, 6β, 7α)-6-ethyl-7-hydroxy-3-oxo-cholan-23-carboxy-24-oic acid dimethyl ester (1.77 g) in DCM (45 mL, 25 vol) under argon was added DMP (1.83 g, 1.2 eq) in 4 portions at 5 min intervals. After 30 mins the mixture was partitioned between EtOAc (50 mL) and 10% aq. Na$_2$S$_2$O$_3$/2% aq. NaHCO$_3$ and stirred for 1 h. The aqueous phase was extracted with EtOAc (50 mL) and the combined organic phases washed with 1M aq. NaOH (50 mL). The organic phase was dried over Na$_2$SO$_4$, filtered and concentrated in vacuo. Purification by column chromatography gave (5β, 6β)-6-ethyl-3,7-dioxo-cholan-23-carboxy-24-oic acid dimethyl ester (1.54 g, 87%) as a white crystalline solid.

$^1$H NMR (700 MHz, CDCl$_3$): δ=3.75 (3H, s), 3.73 (3H, s), 3.47 (1H, dd, J=10.9, 4.0), 2.42 (1H, t, J=11.4), 2.31-2.17 (5H, m), 2.05 (1H, m), 2.01-1.93 (2H, m), 1.89-1.78 (5H, m), 1.67-1.62 (1H, m), 1.58-1.46 (5H, m), 1.39-1.15 (5H, m), 1.14 (3H, s), 0.94 (3H, d, J=6.4), 0.85 (3H, t, J=7.4), 0.71 (3H, s).

$^{13}$C NMR (176 MHz, CDCl$_3$): δ=214.6, 211.6, 170.4, 170.0, 57.2, 55.5, 52.6, 52.4, 50.3, 49.4, 48.5, 47.3, 44.9, 43.6, 43.2, 39.2, 35.8, 35.3, 35.1, 34.9, 34.3, 28.1, 24.6, 23.8, 23.5, 21.7, 18.2, 12.6, 12.2.

G. Synthesis of (5β, 6α)-6-ethyl-3,7-dioxo-cholan-23-carboxy-24-oic Acid Dimethyl Ester

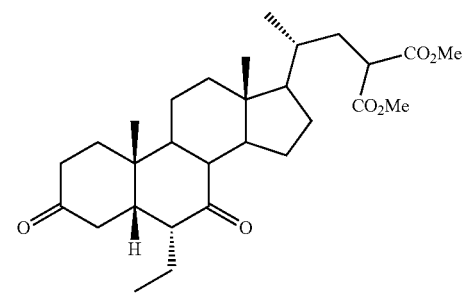 [SMILES: CC[C@H]1C(=O)C2C3CCC([C@H](C)CC(C(=O)OC)C(=O)OC)[C@@]3(C)CCC2[C@@]2(C)CCC(=O)C[C@@H]12]

To (5β, 6β)-6-ethyl-3,7-dioxo-cholan-23-carboxy-24-oic acid dimethyl ester (1.46 g) in MeOH (36 mL, 25 vol) under argon was added NaOMe (324 mg, 2 eq) and the solution stirred at 40° C. for 16 hours. AcOH (5 mL) was added dropwise and the solution stirred for 5 minutes. The solution was taken up in EtOAc (100 mL) and washed with 5% aq. NaCl (2×100 mL). The organic phase was dried over $Na_2SO_4$, filtered and concentrated in vacuo. Purification by column chromatography gave (5β, 6α)-6-ethyl-3,7-dioxo-cholan-23-carboxy-24-oic acid dimethyl ester (0.45 g, 31%).

$^1$H NMR (700 MHz, $CDCl_3$): δ=3.75 (3H, s), 3.73 (3H, s), 3.47 (1H, dd, J=11.0, 4.0), 2.74 (1H, dd, J=11.0, 6.6), 2.47 (1H, t, J=11.3), 2.29-2.16 (5H, m), 2.09-1.96 (3H, m), 1.89-1.80 (2H, m), 1.72-1.46 (6H, m), 1.39-1.34 (1H, m), 1.33 (3H, s), 1.32-1.23 (2H, m), 1.21-1.13 (2H, m), 1.10-1.07 (1H, m), 0.99-0.95 (1H, m), 0.94 (3H, d, J=6.5), 0.81 (3H, t, J=7.4), 0.68 (3H, s); $^{13}$C NMR (176 MHz, $CDCl_3$): δ=212.1, 210.5, 170.3, 170.0, 55.3, 52.6, 52.4, 52.3, 52.2, 49.9, 49.34, 48.8, 43.7, 42.7, 38.8, 38.3, 36.6, 35.9, 35.4, 35.1, 34.2, 28.2, 24.5, 22.9, 22.2, 18.6, 18.2, 12.1, 11.8.

H. Synthesis of (3α, 5β, 6α)-6-ethyl-3-hydroxy-7-oxo-cholan-23-carboxy-24-oic Acid Dimethyl Ester

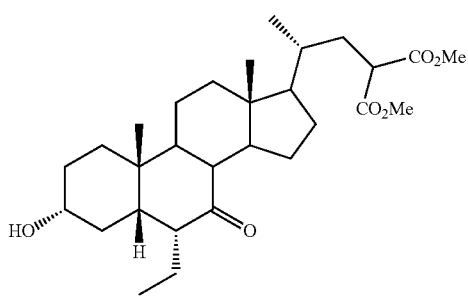 [SMILES: CC[C@H]1C(=O)C2C3CCC([C@H](C)CC(C(=O)OC)C(=O)OC)[C@@]3(C)CCC2[C@@]2(C)CC[C@@H](O)C[C@@H]12]

To a suspension of $NaBH_4$ (27 mg, 1 eq) in IPA (2.3 mL) at −20° C. was added a solution of (5β, 6α)-6-ethyl-3,7-dioxo-cholan-23-carboxy-24-oic acid dimethyl ester (350 mg) in EtOAc (2.3 mL, 6.5 vol) over 10 mins. After 30 mins 0.7M $H_2SO_4$ (2.5 mL) was added dropwise over 10 mins and the solution allowed to warm to 18° C. The solution was diluted with EtOAc (50 mL) and the organic phase washed with water (3×50 mL) and 5% aq. NaCl (50 mL). The organic phase was dried over $Na_2SO_4$, filtered and concentrated in vacuo. Purification by column chromatography gave (3α, 5β, 6α)-6-ethyl-3-hydroxy-7-oxo-cholan-23-carboxy-24-oic acid dimethyl ester (298 mg, 85%)

$^1$H NMR (700 MHz, $CDCl_3$): δ=3.74 (3H, s), 3.72 (3H, s), 3.52 (1H, m), 3.47 (1H, dd, J=11.0, 4.0), 2.69 (1H, dd, J=12.8, 5.9), 2.34 (1H, t, J=11.3), 2.21-2.16 (2H, m), 1.99-1.94 (2H, m), 1.85-1.68 (7H, m), 1.50-1.43 (4H, m), 1.37-1.23 (5H, m), 1.21 (3H, s), 1.20-1.10 (4H, m), 0.92 (3H, d, J=6.5), 0.80 (3H, t, J=7.4), 0.64 (3H, s); $^{13}$C NMR (176 MHz, $CDCl_3$): δ=212.8, 170.4, 170.0, 71.1, 55.3, 52.6, 52.4, 52.0, 50.7, 49.9, 49.0, 43.7, 42.7, 39.0, 35.7, 35.1, 34.3, 34.2, 31.8, 29.8, 28.3, 24.6, 23.5, 21.8, 18.8, 18.2, 12.0, 12.0.

I. Synthesis of (3α, 5β, 6α, 7α)-6-ethyl-3,7-dihydroxy-cholan-23-carboxy-24-oic Acid Dimethyl Ester

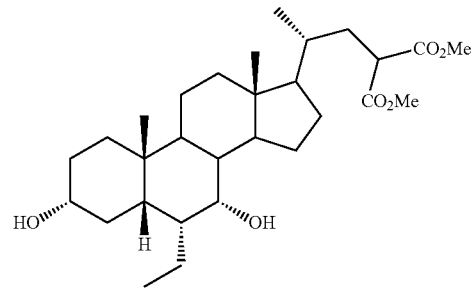 [SMILES: CC[C@H]1[C@@H](O)C2C3CCC([C@H](C)CC(C(=O)OC)C(=O)OC)[C@@]3(C)CCC2[C@@]2(C)CC[C@@H](O)C[C@@H]12]

To a solution of (3α, 5β, 6α)-6-ethyl-3-hydroxy-7-oxo-cholan-23-carboxy-24-oic acid dimethyl ester (200 mg) in THF (20 mL, 100 vol) and water (5 mL, 25 vol) at 0° C. was added $NaBH_4$ (154 mg, 10 eq) in 3 portions. The solution was stirred for one h, allowing to warm to 18° C. MeOH/water (10 mL, 1:1) was added dropwise and the organic solvent removed in vacuo. To the aqueous solution was added 2M aq. HCl (20 mL) dropwise. The aqueous solution was extracted with EtOAc (2×30 mL) and the combined organic phases washed with 5% aq.$NaHCO_3$ (30 mL) and water (30 mL). The organic phase was dried over $Na_2SO_4$, filtered and concentrated in vacuo. Purification by column chromatography gave (3α, 5β, 6α, 7α)-6-ethyl-3,7-dihydroxy-cholan-23-carboxy-24-oic acid dimethyl ester (90 mg, 45%).

$^1$H NMR (700 MHz, $CDCl_3$): δ=3.75 (3H, s), 3.72 (3H, s), 3.48 (1H, dd, J=11.0, 4.0), 3.69 (1H, bs), 3.40 (1H, m), 2.18 (1H, m), 1.97-1.93 (2H, m), 1.85-1.75 (4H, m), 1.73-1.57 (4H, m), 1.51-1.11 (18H, m), 1.00 (1H, td, J=14.3, 3.4), 0.93 (3H, d, J=6.5), 0.90 (3H, t, J=7.3), 0.64 (3H, s); $^{13}$C NMR (176 MHz, $CDCl_3$): δ=170.5, 170.1, 72.3, 70.9, 56.3, 52.6, 52.4, 50.5, 49.4, 45.2, 42.8, 41.2, 40.0, 39.6, 35.6, 35.5, 35.2, 34.4, 34.0, 33.2, 30.6, 28.2, 23.7, 23.2, 22.2, 20.7, 18.2, 11.8, 11.7.

J. Synthesis of (3α, 5β, 6α, 7α)-6-ethyl-3,7-dihydroxy-cholan-23-carboxy-24-oic Acid

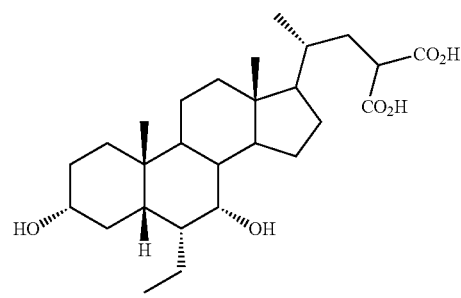 [SMILES: CC[C@H]1[C@@H](O)C2C3CCC([C@H](C)CC(C(=O)O)C(=O)O)[C@@]3(C)CCC2[C@@]2(C)CC[C@@H](O)C[C@@H]12]

To a solution of (3α, 5β, 6α, 7α)-6-ethyl-3,7-dihydroxy-cholan-23-carboxy-24-oic acid dimethyl ester (70 mg) in IPA (2 mL, 28 vol) was added 0.5 M aqueous NaOH (2 mL, 28 vol) and the mixture stirred at 60° C. for 2 h. The organic solvent was removed in vacuo and the aqueous solution adjusted to pH1 with 2M aq. $H_2SO_4$. EtOAc (20 mL) was added and the mixture stirred for 5 mins. The aqueous phase was re-extracted with EtOAc (10 mL). The combined organic phases were washed with 5% aq.NaCl (2×10 mL), dried over $Na_2SO_4$, filtered and concentrated in vacuo to give (3α, 5β, 6α, 7α)-6-ethyl-3,7-dihydroxy-cholan-23-carboxy-24-oic acid as a white solid (54 mg, 81%).

$^1$H NMR (700 MHz, d-6 Acetone): δ=3.58 (1H, bs), 3.32 (1H, dd, J=11.1, 3.6), 3.18 (1H, m), 2.03 (1H, m), 1.90-1.62 (6H, m), 1.57 (1H, m), 1.48-1.31 (8H, m), 1.28-1.13 (6H, m), 1.11-1.05 (3H, m), 0.98 (3H, m), 0.87 (3H, d, J=6.1), 0.85 (1H, m) 0.79 (3H, s), 0.75 (3H, t, J=7.3), 0.74 (3H, s); $^{13}$C NMR (176 MHz, d-6 Acetone): δ=171.7, 171.3, 72.5, 70.4, 57.5, 51.4, 46.7, 43.4, 42.6, 41.3, 40.7, 36.7, 36.3, 36.2, 35.3, 34.6, 34.0, 31.5, 30.6, 29.0, 24.3, 23.7, 23.2, 21.6, 18.7, 12.3, 12.1.

K. Synthesis of (3α, 5β, 6α, 7α)-6-ethyl-3,7-dihydroxy-cholan-24-oic Acid

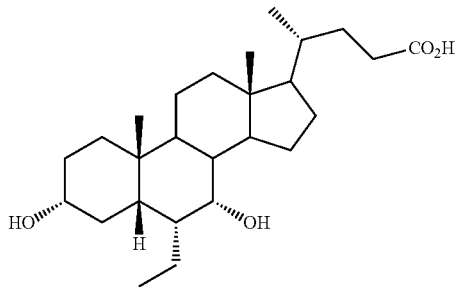 [SMILES: CC[C@H]1[C@@H](O)C2C3CCC([C@H](C)CCC(=O)O)[C@@]3(C)CCC2[C@@]2(C)CC[C@@H](O)C[C@@H]12]

(3α, 5β, 6α, 7α)-6-ethyl-3,7-dihydroxy-cholan-23-carboxy-24-oic acid (25 mg) was taken up in xylene (1.25 mL, 50 vol) and pyridine (250 μL, 10 vol) and the solution heated to reflux for 90 mins. The cooled solution was diluted with EtOAc (20 mL) and washed with 1M aq. HCl (3×10 mL). The organic phase was washed with water (3×10 mL), 5% aq. NaCl (10 mL), dried over $Na_2SO_4$, filtered and concentrated. Purification by column chromatography gave (3α, 5β, 6α, 7α)-6-ethyl-3,7-dihydroxy-cholan-24-oic acid as a white solid (19 mg, 82%).

$^1$H and $^{13}$C NMR were consistent with an authentic sample of (3α, 5β, 6α, 7α)-6-ethyl-3,7-dihydroxy-cholan-24-oic acid.

L. Synthesis of (5β, 6α)-6-ethyl-3,7-dioxo-cholan-23-carboxy-24-oic Acid

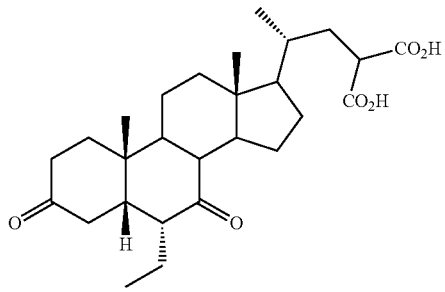 [SMILES: CC[C@H]1C(=O)C2C3CCC([C@H](C)CC(C(=O)O)C(=O)O)[C@@]3(C)CCC2[C@@]2(C)CCC(=O)C[C@@H]12]

To a solution of (5β, 6β)-6-ethyl-3,7-dioxo-cholan-23-carboxy-24-oic acid dimethyl ester (100 mg) in IPA (1 mL, 10 vol) was added 0.5 M aqueous NaOH (1 mL, 10 vol) and the mixture stirred at 60° C. for 2 h. The organic solvent was removed in vacuo and the aqueous solution adjusted to pH1 with 2M aqueous $H_2SO_4$. EtOAc (10 mL) was added and the mixture stirred 5 mins. The aqueous phase was re-extracted with EtOAc (10 mL). The combined organic phases were washed with 5% aq. NaCl (2×10 mL), dried over $Na_2SO_4$, filtered and concentrated in vacuo to give (5β, 6α)-6-ethyl-3,7-dioxo-cholan-23-carboxy-24-oic acid (100 mg, quant.) as a white solid.

$^1$H NMR (500 MHz, $CDCl_3$): δ=3.51 (1H, m), 2.76 (1H, m), 2.49 (1H, t, J=11.1), 2.34-1.80 (14H, m), 1.71-1.43 (7H, m), 1.33 (3H, s), 1.23-1.04 (3H, m), 0.98 (3H, d, J=6.1), 0.94 (1H, m), 0.80 (3H, d, J=7.3), 0.69 (3H, s).

M. Synthesis of (5β, 6α)-6-ethyl-3,7-dioxo-cholan-24-oic Acid

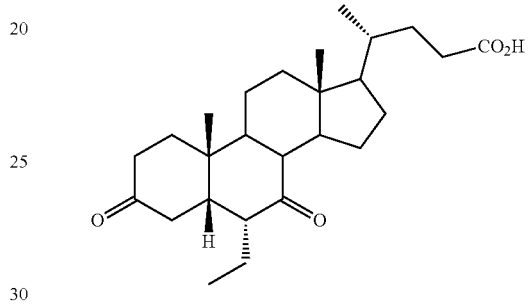

(5β, 6α)-6-ethyl-3,7-dioxo-cholan-23-carboxy-24-oic acid (80 mg) was taken up in xylene (4 mL, 50 vol) and pyridine (800 μL, 10 vol) and the solution heated to reflux for 90 mins. The cooled solution was diluted with EtOAc (25 mL) and washed with 1M aq.HCl (3×10 mL). The organic phase was washed with water (3×10 mL), 5% aq. NaCl (10 mL), dried over $Na_2SO_4$ and filtered. Purification by column chromatography gave (5β, 6α)-6-ethyl-3,7-dioxo-cholan-24-oic acid as a white solid (60 mg, 83%).

$^1$H and $^{13}$C NMR were consistent with an authentic sample of the target compound, prepared as described in Example 16 of WO 2016/079520.

Although the compound of general formula (XXI) was prepared from a compound of general formula (IF) by conversion of the malonate side chain of the compound of general formula (IF) to a carboxylic acid group, a person of skill in the art will appreciate that the conversion of the malonate to carboxylic acid could take place at an earlier stage of the synthesis as described in steps M and N above, and that the carboxylic acid group could, if necessary, be protected, for example as an ester.

Example 4—Preparation of an Analogue of a Compound of General Formula (I) and a Compound of General Formula (XXI) Via Compounds of General Formula (I) with Nitrile Side Chain (Including Side Chain Extension)

Scheme 5 shows the conversion of a compound of general formula (II) in which —YR$^4$ is $CH_2OH$ conversion to a compound of general formula (II) in which —YR$^4$ is —$CH_2CH_2$—CN and subsequently to a compound of general formula (XXI) in which —YR$^{4a}$ is $CH_2CH_2C(O)OH$. The reaction proceeds via compounds of general formulae (IA), (IB), (IC) and (IE) in which —YR$^4$ is —$CH_2CH_2$—CN. The compound of general formula (IE) is then converted to a 3-OH analogue and the side chain is then converted to —$CH_2CH_2$—C(O)OH.

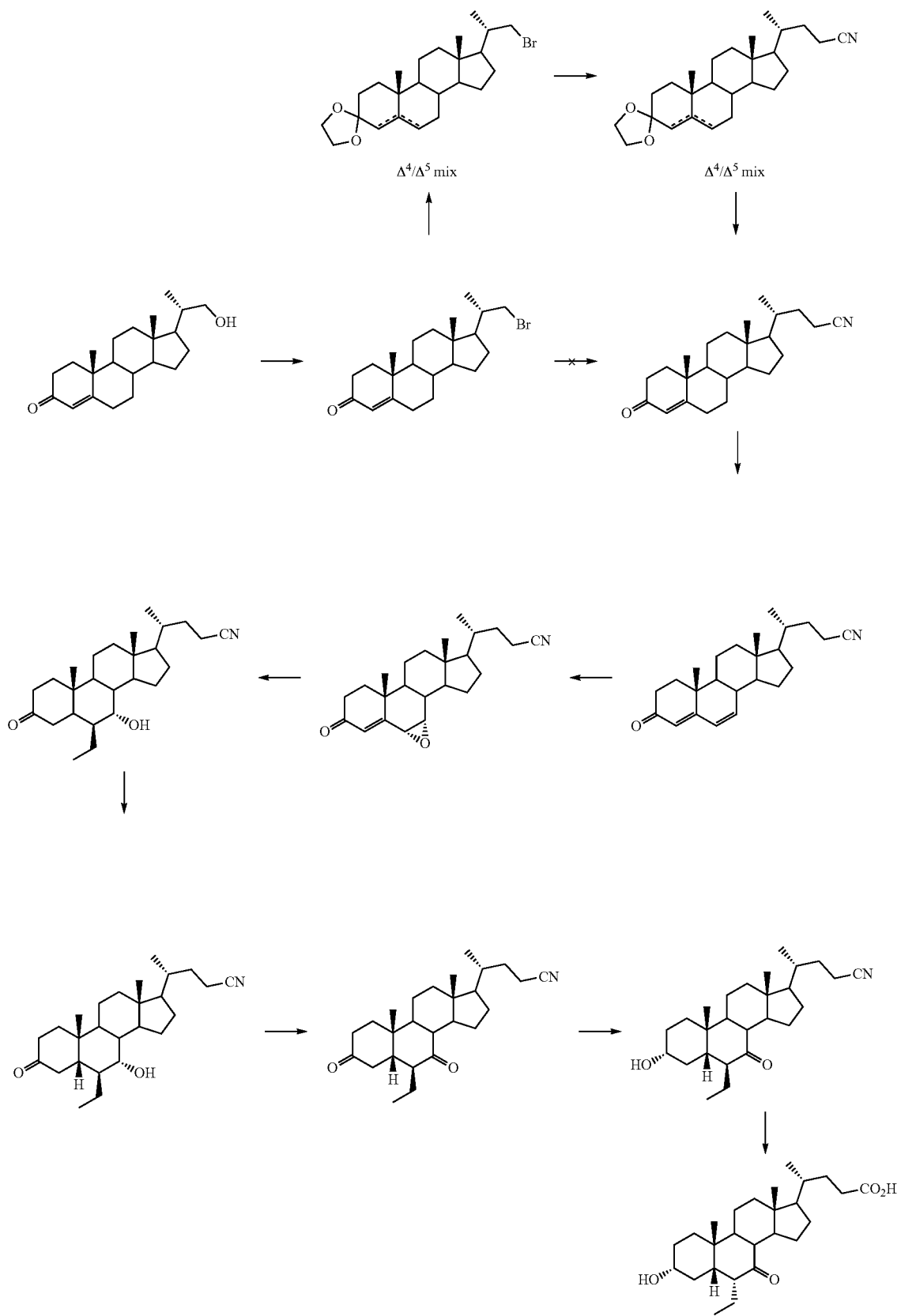

A. Synthesis of (20S)-20-bromomethyl-3,3-ethylenedioxy-4-pregnene and (20S)-20-bromomethyl-3,3-ethylenedioxy-5-pregnene

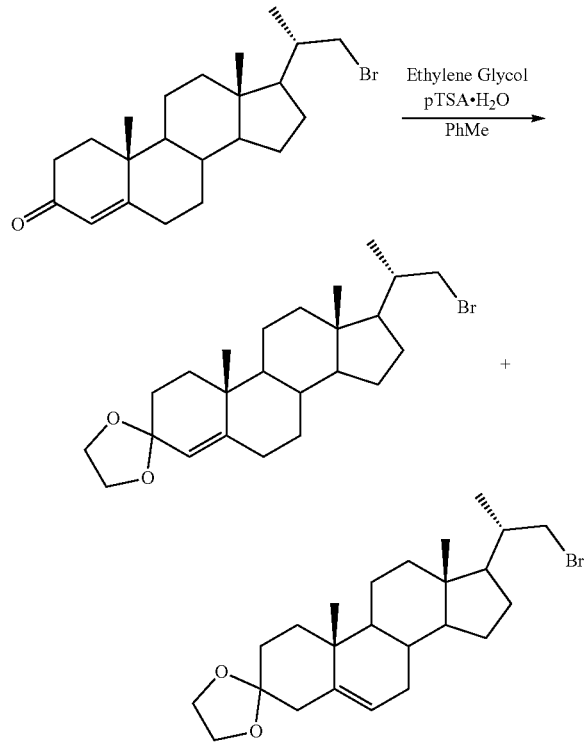

To a solution of (20S)-20-bromomethyl-4-pregnene-3-one (1.00 g, 2.59 mmol) and ethylene glycol (2.0 mL, 36.25 mmol) in toluene (30 mL) was added pTSA.H$_2$O (9.86 mg, 0.05 mmol) and the mixture was heated to reflux using a Dean Stark apparatus for 5 h. The reaction mixture was allowed to cool to room temperature before being poured onto 5% aq. NaHCO$_3$ (30 mL). The layers were separated and the aqueous layer was extracted with CH$_2$Cl$_2$ (2×30 mL). The combined organics were dried over sodium sulfate and were concentrated under reduced pressure. The residue was used in the next step without purification. A sample was purified by column chromatography (heptane/EtOAc) to give a mixture of (20S)-20-bromomethyl-3,3-ethylenedioxy-4-pregnene and (20S)-20-bromomethyl-3,3-ethylenedioxy-5-pregnene in 68% yield (the ratio of $\Delta^5$:$\Delta^4$ was approximately 3.6:1). δH (700 MHz, CDCl$_3$); 5.35 (0.8H, dt, J=4.4, 2.2), 5.23 (0.2H, s), 4.02-3.96 (4H, m, CH$_2$O), 3.51 (0.8H, dd, J 9.7, 2.7), 3.51-3.49 (0.2H, m), 3.34 (0.8H, dd, J 9.7, 6.0), 3.33 (0.2H, dd, J 9.7, 6.1), 2.56 (0.8H, dq, J 14.1, 2.9), 2.20 (0.2H, td, J 13.9, 4.9, 1.8), 2.12 (0.8H, dd, J 14.2, 2.9), 2.05 (0.2H, ddd, J 14.0, 4.2, 2.4), 1.99-1.93 (2H, m), 1.91-1.83 (1H, m), 1.81-1.75 (2H, m), 1.74-1.62 (4H, m), 1.60 (0.8H, s), 1.561.51 (1H, m), 1.50-1.41 (2H, m), 1.37-1.25 (3H, m), 1.21 (1H, td, J 6.5, 4.2), 1.17-1.04 (3H, m), 1.09 (3H, d, J 6.4), 1.03 (3H, s), 1.01-0.84 (0.8H, m), 0.71 (2.4H, s), 0.70 (0.6H, s); δC (176 MHz, CDCl$_3$); 151.6, 140.2, 122.1, 119.65, 109.5, 106.2, 64.6, 64.5, 64.2, 64.2, 56.7, 55.7, 53.8, 53.7, 53.7, 49.6, 43.6, 43.5, 42.5, 42.4, 41.8, 39.5, 39.5, 37.9, 37.8, 37.4, 36.6, 36.3, 35.8, 34.9, 32.4, 32.1, 31.9, 31.9, 31.7, 31.1, 30.0, 27.6, 27.6, 24.2, 24.1, 21.0, 18.9, 18.7, 18.6, 17.6, 12.3, 12.2.

B. Synthesis of 3,3-ethylenedioxy-4-choleno-24-nitrile and 3,3-Ethylenedioxy-5-choleno-24-nitrile

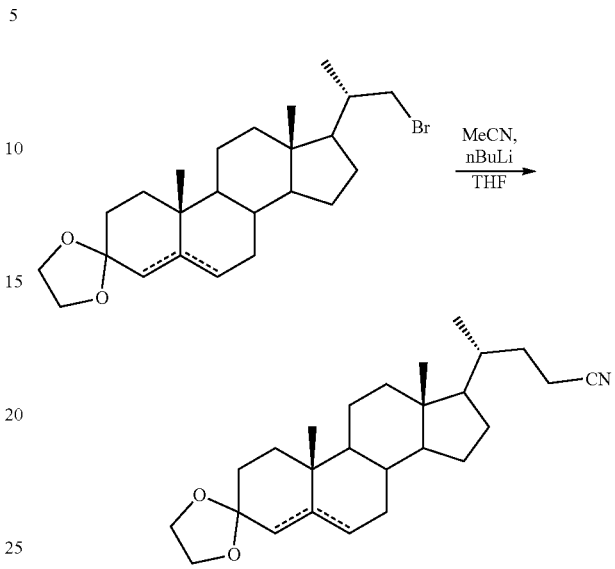

Procedure A

A solution containing MeCN (26.0 mg, 0.63 mmol) in THF (1.85 mL) was cooled to −78° C. under argon and nBuLi (0.32 mL, 2 M in cyclohexane, 0.63 mmol) was charged dropwise over 2 min. To this mixture, a solution containing (20S)-20-bromomethyl-3,3-ethylenedioxy-4-pregnene and (20S)-20-bromomethyl-3,3-ethylenedioxy-5-pregnene (185 mg, 0.423 mmol) in THF (2.15 mL) was charged dropwise over 30 min. The reaction mixture was allowed to warm to 0° C. over 4 h, cooled to −78° C. and quenched with 10% aq. NH$_4$Cl (3 mL). The reaction mixture was diluted with EtOAc (20 mL) and 10% aq. NH$_4$Cl (20 mL) and the organic phase was separated. The aqueous phase was extracted with EtOAc (20 mL), and the combined organic phases were washed with 5% aq. NaCl (20 mL), dried over sodium sulfate and concentrated under reduced pressure. The residue was purified by column chromatography on silica gel using heptane:EtOAc (5:1) as the eluent. A fraction containing 3,3-ethylenedioxy-4-choleno-24-nitrile and 3,3-ethylenedioxy-5-choleno-24-nitrile was obtained in 49% yield (the ratio of $\Delta^5$:$\Delta^4$ was approximately 7:1). δH (700 MHz, CDCl$_3$); 5.35 (0.9H, dt, J 4.5, 2.2), 5.2 (0.1H, brs), 4.02-3.86 (4H, m), 2.56 (0.9H, dq, J 14.2, 2.9), 2.39-2.34 (0.1H, m), 2.34 (0.9H, ddd, J 16.9, 8.6, 5.1), 2.27 (0.9H, dt, J 16.8, 8.4), 2.27 (0.1H, dt, J 16.8, 8.4), 2.20 (0.1H, td, J 13.9, 5.0, 1.8), 2.12 (0.9H, dd, J 14.2, 3.0), 2.05 (0.1H, ddd, J 13.8, 4.4, 2.2), 2.01-1.95 (2H, m), 1.87-1.75 (4H, m), 1.73-1.70 (0.3H, m), 1.69-1.59 (3.4H, m), 1.58-1.52 (2H, m), 1.50-1.43 (2H, m), 1.39-1.25 (4.6H, m), 1.18 (1H, td, J 6.5, 4.2), 1.14-0.99 (4H, m), 1.03 (3H, s), 0.96 (2.7H, d, J 6.6), 0.94 (0.3H, d, J 6.7), 0.88 (0.9H, t, J 14.3), 0.70 (2.7H, s), 0.70 (0.3H, s); δC (176 MHz, CDCl$_3$); 151.6, 140.1, 122.1, 120.2, 119.6, 109.5, 106.2, 64.6, 64.4, 64.2, 56.7, 56.0, 55.5, 55.5, 53.8, 49.6, 42.6, 42.5, 41.8, 39.8, 39.7, 37.4, 36.6, 36.3, 35.7, 35.2, 35.2, 34.9, 32.4, 32.1, 31.9, 31.9, 31.7, 31.6, 31.5, 31.1, 30.0, 29.7, 28.1, 28.1, 24.2, 24.1, 22.7, 21.0, 18.9, 17.9, 17.9, 17.6, 14.3, 14.2, 14.1, 12.0, 11.9.

Procedure B

A solution of MeCN (2.06 mL, 39.43 mmol) in THF (34 mL) was charged dropwise over 1.2 h to a solution of nBuLi (19.72 mL, 2 M in cyclohexane, 39.43 mmol) in THF (69 mL) at −60° C. under argon. To the resulting white suspension, a solution containing (20S)-20-bromomethyl-3,3-ethylenedioxy-4-pregnene and (20S)-20-bromomethyl-3,3-ethylenedioxy-5-pregnene (6.9 g, 15.77 mmol) in THF (69 mL) was charged dropwise over 1.2 h. The thick suspension that formed was warmed to 0° C. over 15 min and water (69 mL) was charged dropwise. The layers were separated and the aqueous phase was extracted with EtOAc (2×100 mL). The combined organic phases were washed with 5% aq. NaCl (2×100 mL) and concentrated under reduced pressure. The residue was purified by column chromatography on silica gel using a gradient of EtOAc in heptane as the eluent. A fraction containing 3,3-ethylenedioxy-4-choleno-24-nitrile and 3,3-ethylenedioxy-5-choleno-24-nitrile was obtained which also contained the product from double-alkylation of MeCN (mass 3.88 g).

C. Synthesis of 3-oxo-4-choleno-24-nitrile

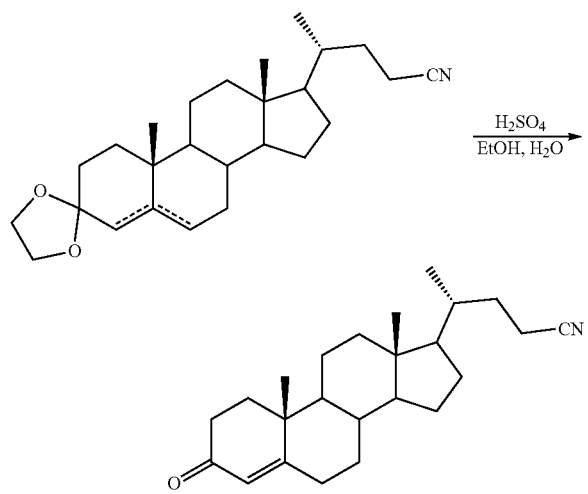

To a solution of 3,3-ethylenedioxy-4-choleno-24-nitrile and 3,3-ethylenedioxy-5-choleno-24-nitrile (3.75 g, 9.43 mmol) in EtOH (75 mL) was added a solution of $H_2SO_4$ (1 mL, conc, 18.86 mmol) in water (7.5 mL). The reaction mixture was heated at reflux for 30 min and cooled to room temperature. A white solid was removed by filtration and the filter-cake was washed with EtOH (2×20 mL). Pyridine (3 mL) was added to the combined wash and filtrate and the mixture was concentrated under reduced pressure. The residue was dissolved in EtOAc (100 mL), washed with 1 M aq. $H_2SO_4$ (100 mL), 5% aq. $NaHCO_3$ (100 mL), 5% aq. NaCl (2×100 mL), dried over sodium sulfate and was concentrated under reduced pressure to give the desired product (2.36 g). $^1$H NMR (700 MHz, $CDCl_3$): δ=5.72 (1H, s, C4-CH), 2.45-2.25 (6H, m), 2.04-2.00 (2H, m), 1.89-1.82 (3H, m), 1.69 (1H, td, J 7.0, 4.6), 1.67-1.62 (1H, m), 1.59-1.51 (3H, m), 1.44 (1H, qd, J 13.1, 4.0), 1.39-1.25 (3H, m), 1.20-1.10 (3H, m), 1.18 (3H, s), 1.05-0.99 (2H, m), 0.96 (3H, d, J 6.6), 0.95-0.91 (1H, m), 0.73 (3H, s); $^{13}$C NMR (176 MHz, $CDCl_3$): δ=199.6 (C=O), 171.4 (C=CH), 123.8 (C=CH), 120.2 (CN), 55.8, 55.5, 53.7, 42.6, 39.6, 38.6, 35.7, 35.6, 35.1, 34.0, 32.9, 32.0, 31.5, 28.1, 24.1, 21.0, 17.9, 17.4, 14.3, 12.0

D. Synthesis of 3-oxo-4,6-choladieno-24-nitrile

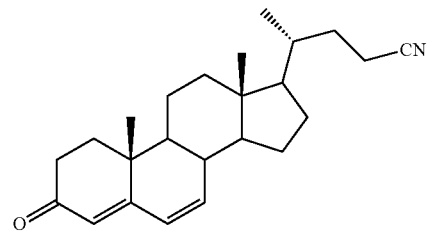 [SMILES: C[C@H](CCC#N)C1CCC2C3C=CC4=CC(=O)CC[C@]4(C)C3CC[C@@]21C]

To a solution of 3-oxo-4-choleno-24-nitrile (2.25 g, 0.64 mmol) in toluene (2.25 mL) and AcOH (6.75 mL) was added chloranil (1.72 g, 0.70 mmol). The mixture was heated at 100° C. for 45 min and was then allow to cool to room temperature. The mixture was filtered, washing with AcOH:toluene (3:1, 20 mL) and the combined filtrates were concentrated under reduced pressure. The residue was concentrated from toluene (3×40 mL) and acetone (3×40 mL) and was then dissolved in acetone (6.75 mL). The solution was charged to an aqueous solution of NaOH (22.5 mL, 3% w/v) and the sticky solid that formed was collected by filtration and washed with water:acetone (2×20 mL, 2:1). The solid was purified by chromatography on silica gel using a gradient of EtOAc in heptane as the eluent to give the desired product as a yellow solid (1.33 g, 59% yield). $^1$H NMR (700 MHz, $CDCl_3$): δ=6.13 (1H, d, J 11.0), 6.10 (1H, dd, J 9.8, 2.3), 5.67 (1H, s), 2.57 (1H, ddd, J 17.9, 14.5, 5.4), 2.45-2.41 (1H, m), 2.39 (1H, ddd, J 17.0, 8.3, 5.1), 2.29 (1H, dt, J 16.8, 8.4), 2.20 (1H, t, J 10.6), 2.05 (1H, dt, J 12.9, 3.4), 2.00 (1H, ddd, J 13.2, 5.3, 2.0), 1.95-1.89 (1H, m), 1.88-1.80 (2H, m), 1.71 (1H, td, J 9.7, 1.3), 1.62-1.54 (2H, m), 1.44 (1H, qd, J 9.7, 1.3), 1.41-1.34 (2H, m), 1.30 (1H, ddd, J 24.0, 11.7, 5.8), 1.25-1.19 (3H, m), 1.17 (1H, q, J 9.5), 1.11 (3H, s), 0.97 (3H, d, J 6.7), 0.78 (3H, s); $^{13}$C NMR (176 MHz, $CDCl_3$): δ=199.6, 163.8, 141.1, 127.9, 123.6, 120.1, 55.4, 53.4, 50.6, 43.6, 39.5, 37.7, 36.0, 35.2, 34.0, 33.9, 31.4, 28.1, 23.7, 20.6, 17.9, 16.3, 14.4, 11.9

E. Synthesis of (6α, 7α)-6,7-epoxy-3-oxo-4-choleno-24-nitrile

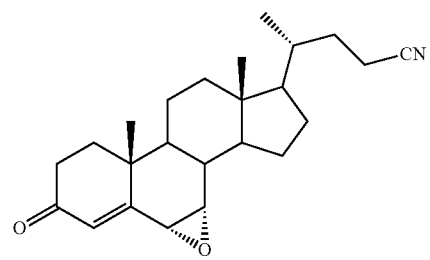 [SMILES: C[C@H](CCC#N)C1CCC2C3C(CC[C@@]21C)[C@@]1(C)CCC(=O)C=C1[C@H]1O[C@@H]31]

A solution of 3-oxo-4,6-choladieno-24-nitrile (1.25 g, 3.56 mmol) in EtOAc (2.5 mL) and HFIP (5 mL) under argon was cooled to 10° C. MTO (8.9 mg, 0.036 mmol), 3-methylpyrazole (0.017 mL, 0.213 mmol) and UHP (0.37 g, 3.91 mmol) were charged and the mixture was stirred for 2 h. Further portions of MTO (8.9 mg, 0.036 mmol), 3-methylpyrazole (0.017 mL, 0.213 mmol) and UHP (67 mg, 0.71 mmol) were charged and the mixture was stirred overnight at 10° C. The reaction was quenched by addition of 5% aq. NaHSO₃ (15 mL) was charged and the mixture was extracted with EtOAc (20 mL). The aqueous phase was separated and extracted with EtOAc (20 mL). The combined organic phases were washed with 5% aq. NaCl (20 mL) and were concentrated under reduced pressure. The residue was purified by column chromatography on silica gel using a gradient of EtOAc in heptane as the eluent to give the desired product (0.92 g, 70%). ¹H NMR (700 MHz, CDCl₃): δ=6.11 (1H, s), 3.46 (1H, d, J 3.7), 3.34 (1H, d, J 3.6), 2.55 (1H, ddd, J 18.1, 14.3, 5.5), 2.47-2.44 (1H, m), 2.41-2.37 (1H, ddd, J 16.9, 8.3, 5.0), 2.30 (1H, dt, J 16.8, 8.4), 2.01 (1H, dt, J 12.9, 3.3), 1.98-1.83 (5H, m), 1.71 (1H, td, J 6.9, 5.2), 1.61-1.56 (1H, m), 1.52 (1H, dq, J 12.7, 3.6), 1.46 (1H, ddd, J 12.4, 11.4, 7.0), 1.41-1.26 (5H, m), 1.22-1.17 (2H, m), 1.10 (3H, s), 0.97 (3H, d, J 6.6), 0.76 (3H, s); ¹³C NMR (176 MHz, CDCl₃): δ=198.3, 162.6, 131.1, 120.1, 55.3, 54.6, 52.6, 51.3, 43.2, 50.6, 39.3, 35.6, 35.1, 34.6, 34.1, 33.9, 31.4, 28.2, 23.6, 19.9, 17.8, 17.2, 14.4, 11.8

F. Synthesis of (6β, 7α)-6-ethyl-7-hydroxy-3-oxo-4-choleno-24-nitrile

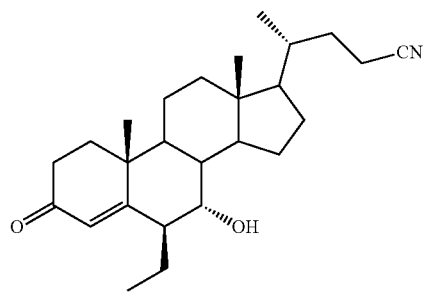 [SMILES: CC[C@H]1C2=CC(=O)CC[C@]2(C)C2CC[C@@]3(C)C(CCC3[C@H](C)CCC#N)C2[C@@H]1O]

A solution of 0.5 M ZnCl₂ in THF (4.65 mL, 2.33 mmol) was cooled to −15° C. and a solution of 1M EtMgBr in TBME (4.65 mL, 4.65 mmol) was charged dropwise over 1 h. A solution of (6α, 7α)-6,7-epoxy-3-oxo-4-choleno-24-nitrile (0.95 g, 2.58 mmol) in THF (4.75 mL) was charged to the resulting mixture over 30 mins. Further portions of 1 M EtMgBr in TBME (4.65 mL, 4.65 mmol and 2.33 mL, 2.33 mmol) were charged after 15 and 20 mins respectively. The reaction mixture was quenched by addition of a sat. aq. NH₄Cl (2 mL), filtered and the filter-cake washed with TBME (20 mL). The filtrate was washed with sat. aq. NH₄Cl (3×20 mL), 5% w/v aq. NaCl (2×20 mL) and concentrated. The residue was purified by column chromatography using EtOAc in heptane to give (6β, 7α)-6-ethyl-7-hydroxy-3-oxo-4-choleno-24-nitrile in 37% yield. ¹H NMR (700 MHz, CDCl₃): δ=5.78 (1H, s), 3.73 (1H, s), 2.48 (1H, ddd, J=17.5, 15.1, 4.9), 2.40-2.36 (2H, m), 2.32-2.26 (2H, m), 2.04-2.00 (2H, m), 1.94-1.89 (1H, m), 1.87-1.83 (1H, m), 1.81-1.73 (2H, m), 1.70 (1H, td, J=11.3, 2.1), 1.64-1.42 (8H, m), 1.40-1.33 (2H, m), 1.27-1.13 (3H, m), 1.22 (3H, s), 0.97 (3H, d, J=6.6), 0.92 (3H, t, J=7.4), 0.76 (3H, s); ¹³C NMR (176 MHz, CDCl₃): δ=199.1, 170.4, 128.7, 120.1, 72.2, 55.5, 55.3, 50.1, 44.3, 42.6, 39.2, 38.3, 37.5, 35.6, 35.2, 34.1, 31.5, 28.0, 26.3, 23.6, 20.9, 19.7, 17.8, 14.3, 12.8, 11.9

G. Synthesis of (5β, 6β, 7α)-6-ethyl-7-hydroxy-3-oxo-cholano-24-nitrile

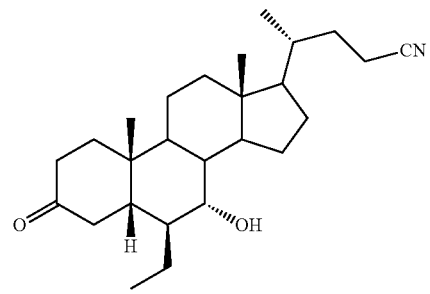 [SMILES: CC[C@@H]1[C@@H](O)C2C3CCC([C@H](C)CCC#N)[C@@]3(C)CCC2[C@@]2(C)CCC(=O)C[C@@H]12]

To a solution of (6β, 7α)-6-ethyl-7-hydroxy-3-oxo-4-choleno-24-nitrile (350 mg, 0.88 mmol) in DMF (2.1 mL) under argon, was charged Pd/C (83 mg, 10% Pd, 45% in H₂O). The reaction vessel was purged with H₂ and stirred under H₂ overnight. The Pd/C was removed by filtration through a PTFE syringe filter and the filter rinsed with TBME (6×2 mL). The filtrate was washed with 5% w/v aq. NaCl (2×10 mL). The aqueous phase was extracted with TBME and the combined organic phases were concentrated to an oily residue. Purification of the residue by column chromatography using EtOAc in heptane to afford (5β, 6β, 7α)-6-ethyl-7-hydroxy-3-oxo-cholano-24-nitrile in 74% yield. ¹H NMR (700 MHz, CDCl₃): δ=3.71 (1H, br, s), 3.34 (1H, dd, J=15.5, 13.4), 2.41-2.33 (2H, m), 2.30 (1H, dt, J=16.8, 8.4), 2.15-2.09 (2H, m), 2.02 (1H, dt, J=12.8, 3.5), 1.98 (1H, dd, J=11.9, 4.6), 1.94-1.89 (2H, m), 1.88-1.83 (1H, m), 1.82 (1H, dd, J=13.4, 4.6), 1.71-1.67 (1H, m), 1.65 (1H, td, J=5.6, 2.8), 1.60-1.14 (17H, m), 1.05 (3H, s), 0.98 (3H, d), 0.94 (3H, t, J=7.2), 0.88 (1H, t, J=7.1), 0.73 (3H, s); ¹³C NMR (176 MHz, CDCl₃): δ=213.5, 120.2, 72.1, 55.6, 50.2, 49.9, 47.0, 46.7, 42.8, 39.5, 37.7, 36.3, 36.0, 35.7, 35.2, 34.2, 31.5, 28.1, 27.7, 24.4, 23.8, 20.8, 17.9, 14.3, 13.9, 11.8

H. Synthesis of (5β, 6β)-3,7-dioxo-6-ethyl-cholano-24-nitrile

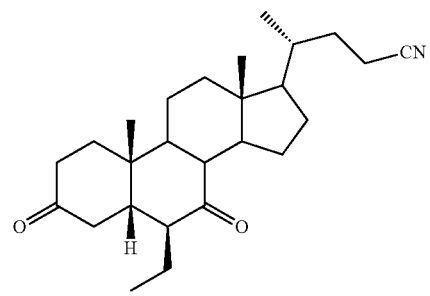 [SMILES: CC[C@@H]1C(=O)C2C3CCC([C@H](C)CCC#N)[C@@]3(C)CCC2[C@@]2(C)CCC(=O)C[C@@H]12]

To a solution of (5β, 6β, 7α)-6-ethyl-7-hydroxy-3-oxo-cholano-24-nitrile (245 mg, 0.61 mmol) in DCM (6.13 mL) under argon, was added DMP (312 mg, 0.74 mmol) in two portions, 5 min apart. The resulting pink suspension was stirred for 30 mins and quenched by addition of 10% w/v aq. Na₂S₂O₃:2% w/v aq. NaHCO₃ (5 mL). The aqueous phase was extracted with TBME (3×20 mL) and the combined organic phases were washed with 5% w/v aq. NaCl (20 mL) and concentrated. The residue was purified by column chromatography using EtOAc in heptane to afford (5β, 6β)-3,7-dioxo-6-ethyl-cholano-24-nitrile in 88% yield. $^1$H NMR (700 MHz, CDCl$_3$): δ=2.45 (1H, t, J=11.4), 2.38 (1H, ddd, J=16.9, 8.2, 5.1), 2.31-2.20 (5H, m), 2.06 (1H, dt, J=12.9, 3.4), 1.99 (1H, quintet, J=4.7), 1.92-1.78 (7H, m), 1.65 (1H, ddd, J=14.4, 9.9, 4.6), 1.60-1.53 (4H, m), 1.52-1.47 (1H, m), 1.40-1.29 (2H, m), 1.25-1.14 (3H, m), 1.16 (3H, s), 0.98 (3H, d, J=6.6), 0.84 (3H, t, J=7.4), 0.74 (3H, s); $^{13}$C NMR (176 MHz, CDCl$_3$): δ=214.5, 211.5, 120.1, 57.4, 54.8, 50.1, 48.6, 47.2, 44.8, 43.7, 43.2, 39.1, 35.8, 35.3, 35.1, 35.0, 31.4, 28.2, 24.6, 23.9, 23.6, 21.7, 18.0, 14.3, 12.7, 12.3

I. Synthesis of (3α, 5β, 6β)-6-ethyl-3-hydroxy-7-oxo-cholano-24-nitrile

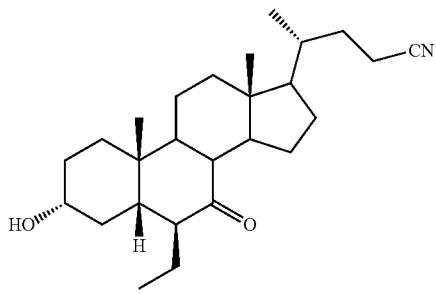 [SMILES: CC[C@@H]1C(=O)C2C3CCC([C@H](C)CCC#N)[C@@]3(C)CCC2[C@@]2(C)CC[C@@H](O)C[C@@H]12]

To a suspension of NaBH$_4$ (19 mg, 0.50 mmol) in IPA (0.8 mL) cooled to −20° C. was charged a solution of (5β, 6β)-3,7-dioxo-6-ethyl-cholano-24-nitrile (200 mg, 0.50 mmol) in EtOAc (1.3 mL) dropwise over 13 mins. A solution of 0.5 M H$_2$SO$_4$ (0.5 mL) in water (0.8 mL) was charged slowly and the reaction mixture was stirred over 15 min and diluted with water (10 mL). The mixture was extracted with EtOAc (3×10 mL) and the combined organic phases were washed with 5% w/v aq. NaCl (3×10 mL) and concentrated. The residue was purified by column chromatography using EtOAc in heptane to afford (3α, 5β, 6β)-6-ethyl-3-hydroxy-7-oxo-cholano-24-nitrile in 73% yield. $^1$H NMR (700 MHz, CDCl$_3$): δ=3.59-3.55 (1H, m), 2.57 (1H, dd, J, 11.9, 10.8), 2.38 (1H, ddd, J 16.9, 8.4, 5.0), 2.28 (1H, dt, J 16.8, 8.4), 2.20-2.16 (1H, m), 2.00-1.94 (2H, m), 1.93-1.83 (3H, m), 1.81-1.72 (3H, m), 1.70-1.64 (3H), 1.57-0.53 (1H, m), 1.52-1.43 (4H, m), 1.39-1.34 (1H, m), 1.32-1.25 (2H, m), 1.22 (3H, s), 1.19-1.11 (4H, m), 0.96 (3H, d, J 6.6), 0.95-0.90 (1H, m), 0.85 (3H, t, J 7.3), 0.69 (3H, s); $^{13}$C NMR (176 MHz, CDCl$_3$): δ=215.3, 120.1, 70.6, 62.1, 54.6, 49.6, 48.7, 45.5, 42.9, 42.6, 39.8, 38.8, 35.6, 35.4, 35.0, 31.5, 29.6, 28.2, 26.6, 26.0, 24.9, 21.4, 18.0, 14.3, 13.1, 12.2

J. Synthesis of (3α, 5β, 6α)-6-ethyl-3-hydroxy-7-oxo-cholan-24-oic Acid

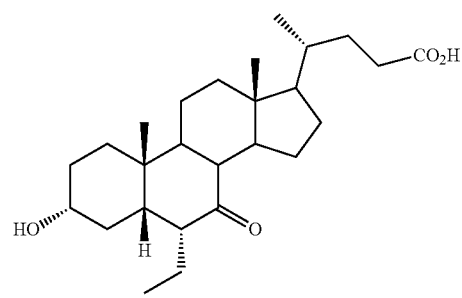 [SMILES: CC[C@H]1C(=O)C2C3CCC([C@H](C)CCC(=O)O)[C@@]3(C)CCC2[C@@]2(C)CC[C@@H](O)C[C@@H]12]

A mixture of (3α, 5β, 6β)-6-ethyl-3-hydroxy-7-oxo-cholano-24-nitrile (130 mg, 0.33 mmol) in MeOH (6 mL), water (6 mL) and KOH (1.8 g, 32.14 mmol) was heated at reflux over 7 h, stirred at ambient for 16 h, then heated at reflux for a further 4 h. The reaction mixture was cooled to ambient temperature and acidified to pH1 with 6M HCl. The mixture was extracted with EtOAc (3×20 mL) and the combined organic phases were washed with 5% w/v aq. NaCl (20 mL) and concentrated to give crude (3α, 5β, 6α)-6-ethyl-3-hydroxy-7-oxo-cholan-24-oic acid in 82% yield. $^1$H and $^{13}$C NMR matched those of an authentic sample.

The product of step J, can be converted to a compound of general formula (XXI) in which R$^{4'}$ is C(O)OH by reduction, for example using sodium borohydride.

As a person of skill in the art would appreciate, the synthetic route shown in Scheme 5 could be adapted by conversion of the nitrile group to a carboxylic acid at an earlier stage followed, if necessary, by protection of the carboxylic acid group, for example as an ester.

Example 5—Preparation of an Analogue of a Compound of General Formula (I) and a Compound of General Formula (XXI) Via Compounds of General Formula (I) with Nitrile Side Chain (not Including Side Chain Extension)

Scheme 6 shows an alternative route in which the side chain is not extended.

Scheme 6

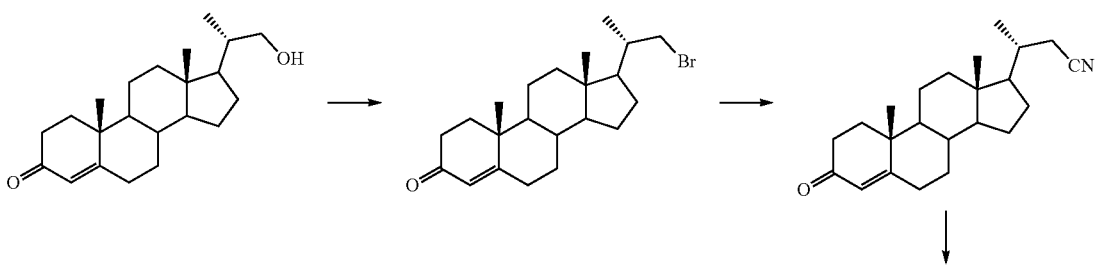

-continued

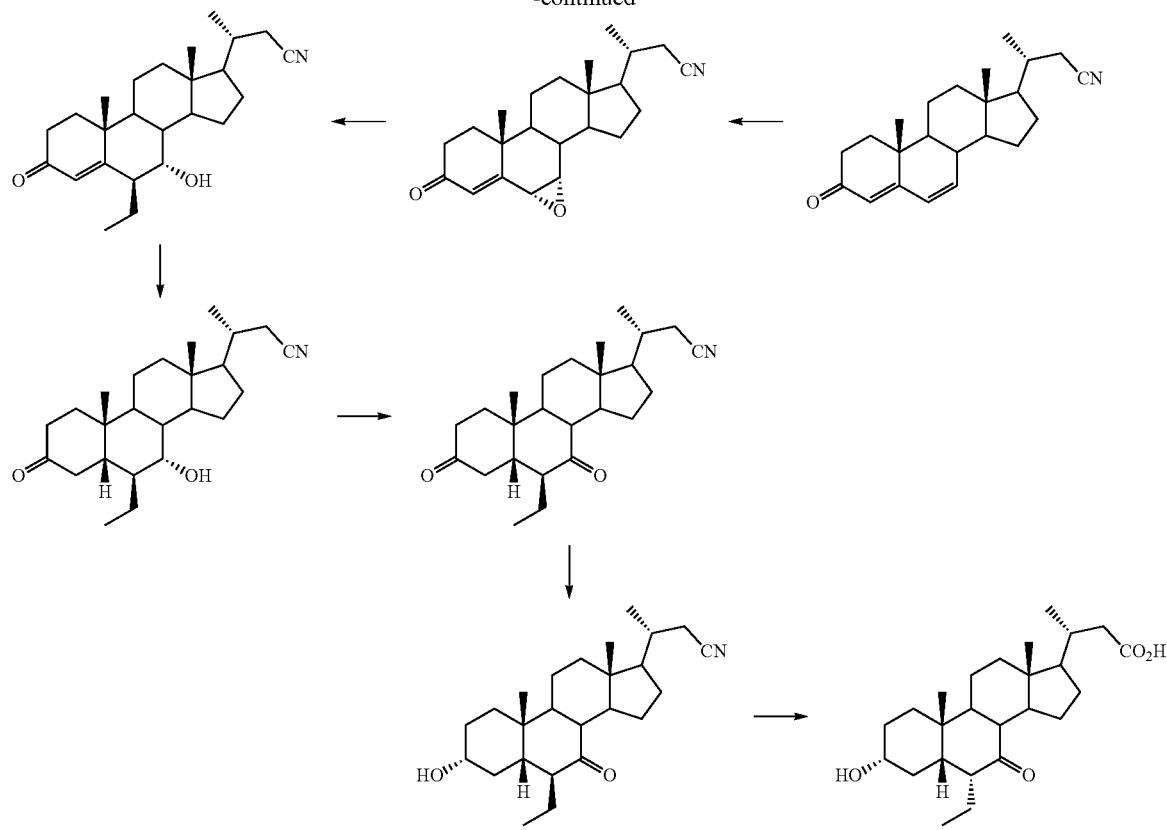

A. Synthesis of (20R)-cyanomethyl-4-pregnen-3-one

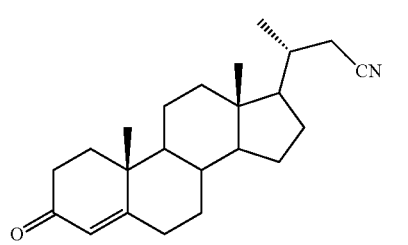 [SMILES: C[C@H](CC#N)C1CCC2C3CCC4=CC(=O)CC[C@]4(C)C3CC[C@@]21C]

To a suspension of (20S)-20-bromomethyl-4-pregnen-3-one (15 g, 38.1 mmol) in DMF (225 mL) was added potassium cyanide (7.5 g, 114 mmol). The suspension was stirred at 80° C. for 41 h before cooling to room temperature. EtOAc (250 mL) and water (500 mL) were added and the layers were separated. The aqueous layer was extracted with EtOAc (2×250 mL) and the combined organic phases were washed with 5% aq. NaCl (250 mL) and were concentrated under reduced pressure. The residue was purified by column chromatography on silica gel (heptane/EtOAc) to afford the desired product (9.7 g, 75%) as a white solid. δH (700 MHz, CDCl$_3$); 5.73 (1H, s, C4-CH), 2.45-2.32 (4H, m), 2.27 (1H, ddd, J=14.6, 4.2, 2.7), 2.24 (1H, dd, J=16.8, 7.1), 2.04-1.99 (2H, m), 1.89-1.78 (3H, m), 1.72-1.65 (2H, m), 1.57-1.51 (2H, m), 1.43 (1H, qd, J=13.2, 4.0), 1.31-1.16 (4H, m), 1.18 (3H, s), 1.17 (3H, d, J=6.7), 1.11-1.01 (2H, m), 0.94 (1H, ddd, J=12.3, 10.7, 4.1), 0.74 (3H, s); δC (176 MHz, CDCl$_3$); 199.5, 171.2, 123.9, 118.9, 55.7, 54.7, 53.6, 42.5, 39.2, 38.5, 35.7, 35.6, 34.0, 33.6, 32.8, 31.9, 28.0, 24.8, 24.1, 20.9, 19.3, 17.4, 12.1.

B. Synthesis of (20R)-cyanomethyl-4,6-pregnadien-3-one

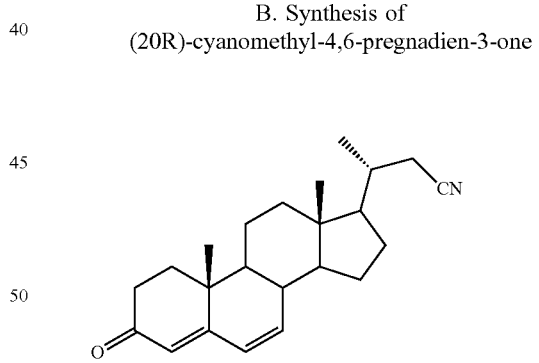

To a suspension of (20R)-cyanomethyl-4-pregnen-3-one (9.1 g, 26.8 mmol) in toluene (36 mL) and acetic acid (0.15 mL) was added p-chloranil (7.2 g, 39.5 mmol). The mixture was heated at reflux for 90 minutes before allowing to cool to room temperature. The suspension was filtered, washing with toluene (25 mL). The filtrate was concentrated under reduced pressure and the residue was purified by column chromatography on silica gel (heptane/EtOAc). The material was then dissolved in acetone (35 mL) and methanol (23 mL) and 0.5 M aq. NaOH (200 mL) was added dropwise. Water (100 mL) was added and the resulting solid was filtered, washing with water (2×50 mL) and 2:1 acetone: water (2×20 mL). The solid was dried in vacuo to afford the desired product (5.4 g, 60%) as a pale brown solid. δH (700 MHz, CDCl₃); 6.11 (2H, s), 5.67 (1H, s), 2.57 (1H, ddd, J=18.0, 14.4, 5.4), 2.45-2.42 (1H, m), 2.37 (1H, dd, J=16.7, 3.7), 2.25 (1H, dd, J=16.7, 7.2), 2.01 (1H, t, J=10.4), 2.03 (1H, dt, J=12.8, 3.3), 2.00 (1H, ddd, J=13.2, 5.4, 2.1), 1.96-1.91 (1H, m), 1.88-1.81 (1H, m), 1.74-1.70 (1H, m), 1.58 (1H, dq, J=13.4, 3.6), 1.44 (1H, qd, J=4.4, 3.9), 1.36-1.20 (7H, m), 1.18 (3H, d, J=6.7), 1.11 (3H, s), 0.79 (3H, s); δC (176 MHz, CDCl₃); 199.6, 163.67, 140.8, 128.1, 123.7, 118.8, 54.6, 53.2, 50.5, 43.5, 39.1, 37.6, 36.0, 33.9, 33.9, 33.5, 28.0, 24.8, 23.6, 20.6, 19.3, 16.3, 12.0.

C. Epoxidation of (20R)-20-(1-cyanomethyl)-pregna-4,6-dien-3-one to Form (6α, 7α, 20R)-20-(1-cyanomethyl)-6,7-epoxy-pregn-4-en-3-one

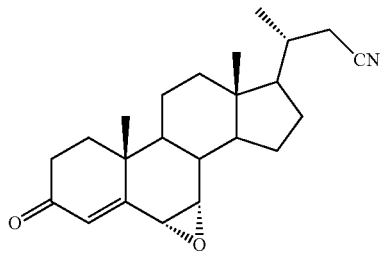 [SMILES: C[C@H](CC#N)C1CCC2C3C(CC[C@@]21C)[C@@]1(C)CCC(=O)C=C1[C@H]1O[C@@H]31]

(20R)-Cyanomethyl-4,6-pregnadien-3-one (5.1 g, 15.1 mmol) was dissolved in HFIP (20 mL) and EtOAc (10 mL) and was cooled to 10° C. MTO (38 mg, 1 mol %), 3-methylpyrazole (73 μL, 6 mol %) and UHP (1.6 g, 16.6 mmol) were added and the mixture stirred at 10° C. After 4 h, MTO (38 mg, 1 mol %), 3-methylpyrazole (73 μL, 6 mol %) and UHP (0.28 g, 3.0 mmol) were added and the mixture stirred at 10° C. After a further 17 h, MTO (38 mg, 1 mol %), 3-methylpyrazole (73 μL, 6 mol %) and UHP (0.28 g, 3.0 mmol) were added and the mixture stirred at 10° C. After a further 72 h the mixture was quenched with 5% aq. sodium bisulfite (20 mL). The mixture was diluted with EtOAc (80 mL), 5% aq. sodium bisulfite (50 mL) and 5% aq. sodium chloride (50 mL). The aqueous phase was extracted with EtOAc (80 mL), and the combined organics washed with 5% aq. sodium chloride (50 mL), dried over sodium sulfate and concentrated in vacuo. The residue was purified by column chromatography on silica gel (heptane-EtOAc) to give the desired product (3.9 g, 73%) as an off-white solid. ¹H NMR (700 MHz, CDCl₃): δ=6.11 (1H, s, C4-CH), 3.46 (1H, d, J=3.9, C6-CH), 3.33 (1H, d, J=3.8, C7-CH), 2.55 (1H, ddd, J=5.6, 14.2, 18.1, C2-CH$_a$H$_b$), 2.48-2.45 (1H, m, C2-CH$_a$H$_b$), 2.39 (1H, dd, J=3.8, 16.7, C22-CH$_a$H$_b$), 2.23 (1H, dd, J=7.6, 16.8, C22-CH$_a$H$_b$), 2.01-1.91 (4H, m, C1-CH$_a$H$_b$, C12-CH$_a$H$_b$, C15-CH$_a$H$_b$, C16-CH$_a$H$_b$), 1.88 (1H, td, J=10.9, 1.3, C8-CH), 1.84-1.80 (1H, m, C20-CH), 1.72 (1H, td, J=5.2, 13.9, C1-CH$_a$H$_b$), 1.56-1.49 (2H, m, C11-CH$_a$H$_b$, C14-CH), 1.38-1.21 (6H, m, C9-CH, C11-CH$_a$H$_b$, C12-CH$_a$H$_b$, C15-CH$_a$H$_b$, C16-CH$_a$H$_b$, C17-CH), 1.18 (3H, d, J=6.8, C21-CH₃), 1.10 (3H, s, C19-CH₃), 0.77 (3H, s, C18-CH₃); ¹³C NMR (176 MHz, CDCl₃): δ=198.3, 162.5, 131.2, 118.9, 54.6, 54.5, 52.5, 51.2, 43.2, 40.5, 38.9, 35.5, 34.6, 34.1, 33.8, 33.7, 28.2, 24.8, 23.6, 19.8, 19.3, 17.2, 11.9.

D. Synthesis of (6β, 7α, 20R)-cyanomethyl-6-ethyl-7-hydroxy-4-pregnen-3-one

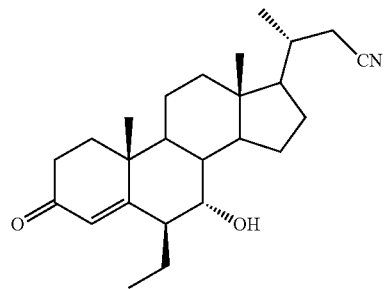 [SMILES: CC[C@H]1C2=CC(=O)CC[C@]2(C)C2CC[C@@]3(C)C(CCC3[C@H](C)CC#N)C2[C@@H]1O]

THF (17 mL) was charged to the reaction vessel, followed by 0.5 M zinc chloride in THF (16.8 mL), and the mixture cooled to −15° C. 1M Ethylmagnesium bromide in TBME (16.8 mL) was added dropwise over ca. 1 h, maintaining the temperature <−7° C. Copper (I) chloride (92 mg, 0.93 mmol) was charged to the reaction mixture. (20R)-Cyanomethyl-6,7-α-epoxy-4-pregnen-3-one (3.3 g, 9.3 mmol) was dissolved in THF (19 mL) and charged dropwise to the reaction mixture, maintaining the temperature <−7° C. The mixture was stirred at −15° C. upon complete addition. After 1 h a second portion of 1M ethylmagnesium bromide in TBME (17 mL) was added dropwise. The mixture was stirred at −15° C. After a further 30 min the mixture was quenched with sat. aq. ammonium chloride (3 mL) and allowed to warm to 15° C. The precipitate was removed by filtration and rinsed with TBME (50 mL). The filtrate was washed with sat. aq. ammonium chloride (3×50 mL) and 5% aq. sodium chloride (25 mL), dried over Na₂SO₄, filtered and concentrated in vacuo to afford (6β, 7α, 20R)-cyanomethyl-6-ethyl-7-hydroxy-4-pregnen-3-one (3.2 g, 89%) as an off-white solid which was used without further purification.

¹H NMR (700 MHz, CDCl₃): δ=5.78 (1H, s), 3.73 (1H, t, J=1.6), 2.48 (1H, ddd, J=17.5, 15.0, 4.9), 2.40-2.36 (2H, m), 2.31 (1H, ddd, J=8.7, 6.9, 1.9), 2.23 (1H, dd, J=16.7, 7.4), 2.03 (1H, ddd, J=13.4, 5.1, 2.3), 1.99 (1H, dt, J=12.7, 3.4), 1.95-1.90 (1H, m), 1.83-1.76 (3H, m), 1.70 (1H, td, J=5.7, 2.1), 1.63-1.44 (6H, m), 1.37-1.16 (5H, m), 1.22 (3H, s), 1.18 (3H, d, J=6.7), 0.92 (3H, t, J=7.4), 0.76 (3H, s); ¹³C NMR (176 MHz, CDCl₃): δ=199.1, 170.3, 128.7, 118.9, 72.1, 55.3, 54.8, 50.0, 44.2, 42.6, 38.9, 38.3, 37.5, 35.6, 34.1, 33.6, 28.0, 26.3, 24.8, 23.6, 20.8, 19.7, 19.3, 12.8, 11.9.

E. Synthesis of (5β, 6β, 7α, 20R)-cyanomethyl-6-ethyl-7-hydroxy-pregna-3-one

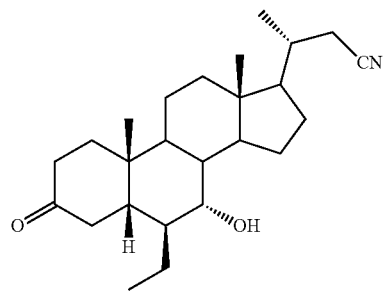 [SMILES: CC[C@@H]1[C@@H](O)C2C3CCC([C@H](C)CC#N)[C@@]3(C)CCC2[C@@]2(C)CCC(=O)C[C@@H]12]

(6β, 7α, 20R)-Cyanomethyl-6-ethyl-7-hydroxy-4-pregnen-3-one (3.1 g, 8.1 mmol) was dissolved in DMF (54.5 mL) and 10% Pd/C charged (0.79 g of a 45% dispersion in water). The mixture was degassed and filled with hydrogen. After 18 h 30 min the mixture was degassed and filled with argon, filtered and rinsed with TBME (3×60 mL). The filtrate was re-filtered and rinsed with TBME (2×50 mL). The filtrate was washed with 5% aq. sodium chloride (100 mL), and the aqueous phase re-extracted with TBME (100 mL). The combined organic phases were washed with 5% aq. sodium chloride (2×100 mL) and concentrated. The residue was purified by flash chromatography (heptane-EtOAc) to afford (5β, 6β, 7α, 20R)-cyanomethyl-6-ethyl-7-hydroxy-pregna-3-one (2.5 g, 80%) as an off-white solid.

$^1$H NMR (700 MHz, CDCl$_3$): δ=3.69 (1H, s), 3.38 (1H, dd, J 15.5, 13.4), 2.39-2.34 (2H, m), 2.25 (1H, dd, J=16.7, 7.4), 2.14-2.08 (2H, m), 2.04-1.98 (2H, m), 1.94-1.90 (2H, m), 1.83-1.80 (2H, m), 1.76-1.74 (1H, m), 1.64 (1H, td, J=11.2, 2.7), 1.60-1.54 (2H, m), 1.51-1.40 (4H, m), 1.38-1.25 (4H, m), 1.21-1.15 (1H, m), 1.18 (3H, d, J=6.7), 1.05 (3H, s), 0.94 (3H, t, J=7.1), 0.74 (3H, s); $^{13}$C NMR (176 MHz, CDCl$_3$): δ=213.7, 118.9, 71.7, 54.9, 50.0, 49.9, 47.0, 46.7, 42.7, 39.1, 37.7, 36.3, 35.9, 35.7, 34.0, 33.6, 28.1, 27.6, 24.8, 24.4, 23.7, 20.7, 19.3, 13.9, 11.9.

F. Synthesis of (5β, 6β, 20R)-cyanomethyl-6-ethyl-7-oxo-pregna-3-one

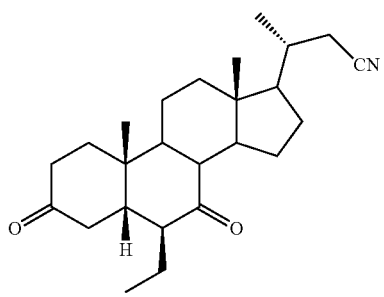 [SMILES: CC[C@@H]1C(=O)C2C3CCC([C@H](C)CC#N)[C@@]3(C)CCC2[C@@]2(C)CCC(=O)C[C@@H]12]

(5β, 6β, 7α, 20R)-Cyanomethyl-6-ethyl-7-hydroxy-pregna-3-one (2.4 g, 6.3 mmol) was dissolved in DCM (60.5 mL) and cooled to 0° C. Dess-Martin periodinane (DMP, 4.8 g, 11.3 mmol) was added over 1 minute. The reaction mixture was stirred at 0° C. After 1 h a second portion of DMP (1.6 g, 3.8 mmol) was added. After 2 h a third portion of DMP (1.6 g, 3.8 mmol) was added. After 3 h a fourth portion of DMP (0.5 g, 1.3 mmol) was added. After 3 h 45 min the mixture was diluted with 10% aq. Na$_2$S$_2$O$_3$/5% aq. NaHCO$_3$ (120 mL) and TBME (90 mL) and stirred vigorously. The phases were separated and the aqueous phase re-extracted with TBME (60 mL). The combined organic phases were concentrated and purified by flash chromatography (heptane-EtOAc) to afford (5β, 6β, 20R)-cyanomethyl-6-ethyl-7-oxo-pregna-3-one (1.8 g, 75%) as an off-white solid.

$^1$H NMR (700 MHz, CDCl$_3$): δ=2.43 (1H, t, J=11.4), 2.38 (1H, dd, J=16.7, 3.6), 2.30-2.20 (5H, m), 2.04 (1H, dt, J=12.7, 3.1), 2.01 (1H, dt, J=9.4, 4.7), 1.94-1.76 (7H, m), 1.66 (1H, ddd, J=14.3, 9.7, 4.3), 1.58-1.52 (4H, m), 1.33-1.21 (4H, m), 1.18 (3H, d, J=6.7), 1.15 (3H, s), 0.85 (3H, t, J=7.4), 0.75 (3H, s); $^{13}$C NMR (176 MHz, CDCl$_3$): δ=214.4, 211.5, 118.6, 57.1, 54.0, 50.1, 48.4, 47.2, 44.7, 43.6, 43.2, 38.8, 35.8, 35.2, 34.9, 33.5, 28.1, 24.8, 24.5, 23.7, 23.4, 21.6, 19.3, 12.6, 12.3.

G. Synthesis of (3α, 5β, 6β, 20R)-cyanomethyl-6-ethyl-7-oxo-pregnane

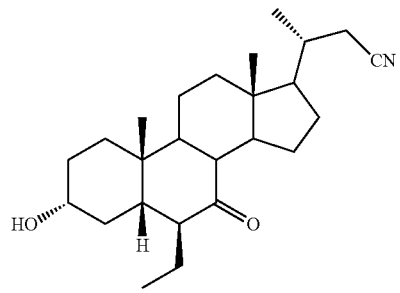 [SMILES: CC[C@@H]1C(=O)C2C3CCC([C@H](C)CC#N)[C@@]3(C)CCC2[C@@]2(C)CC[C@@H](O)C[C@@H]12]

Sodium borohydride (20 mg, 0.52 mmol) was suspended in isopropanol (0.8 mL) and cooled to −20° C. (5β, 6β, 20R)-cyanomethyl-6-ethyl-7-oxo-pregna-3-one (200 mg, 0.52 mmol) was dissolved in ethyl acetate (1.7 mL) and TBME (1.2 mL) and added dropwise to the cold borohydride suspension. The mixture was stirred at −20° C. for 45 min, then quenched by addition of 0.7 M sulfuric acid (1.4 mL) and allowed to warm to 18° C. The mixture was diluted with water (10 mL) and TBME (10 mL) and the phases separated. The aqueous phase was re-extracted with TBME (10 mL) and the combined organic extracts washed with 5% aq. sodium chloride (10 mL). The organic phase was concentrated and purified by flash chromatography to afford (3α, 5β, 6β,20R)-cyanomethyl-6-ethyl-7-oxo-pregnane (113 mg, 56%, containing 10% 3β-OH) as a pale yellow syrup.

$^1$H NMR (700 MHz, CDCl$_3$): δ=4.00-3.99 (0.1H, m, H-3$_{3β-OH}$), 3.68-3.53 (0.9H, m, H-3$_{3α-OH}$), 2.57 (1H, dd, J=11.6, 11.1), 2.38 (1H, dd, J=16.7, 3.7), 2.23-2.20 (2H, m), 1.99-1.87 (5H, m), 1.83-1.64 (6H, m), 1.55-1.45 (3H, m), 1.31-1.18 (7H, m), 1.22 (3H, s), 1.17 (3H, d, J=6.7), 0.99-0.93 (1H, m), 0.84 (3H, t, J=7.3), 0.70 (3H. s); $^{13}$C NMR (176 MHz, CDCl$_3$): δ=215.3 (3α-C=O). 119.0 (CN), 70.5, 62.1, 54.0, 49.6, 48.7, 45.5, 42.8, 42.6, 39.8, 38.5, 35.6, 35.4, 33.6, 29.5, 28.2, 26.6, 26.0, 24.8, 24.8, 21.3, 19.4, 13.1, 12.2.

H. Synthesis of (3α, 5β, 6α)-6-ethyl-7-oxo-24-nor-lithocholic Acid

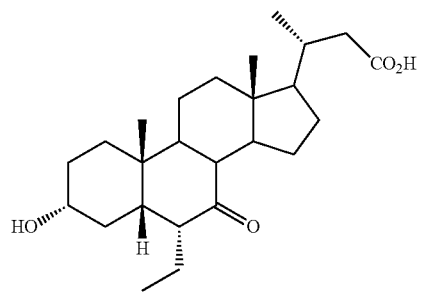 [SMILES: CC[C@H]1C(=O)C2C3CCC([C@H](C)CC(=O)O)[C@@]3(C)CCC2[C@@]2(C)CC[C@@H](O)C[C@@H]12]

(3α, 5β, 6β, 20R)-cyanomethyl-6-ethyl-7-oxo-pregnane (65 mg, 0.17 mmol) was dissolved in methanol (3 mL) and 30% w/v potassium hydroxide solution (3 mL) and heated to reflux for 4 days. The mixture was cooled in an ice bath and 6M hydrochloric acid added to pH 8 (2 mL). Ethyl acetate (10 mL) was added, followed by 6M HCl to pH 1 (0.5 mL).

The mixture was allowed to warm to 18° C. and the phases separated. The organic phase was washed with 5% aq. sodium chloride (20 mL) and concentrated to afford (3α, 5β, 6α)-6-ethyl-7-oxo-24-nor-lithocholic acid (69 mg, quantitative) as a pale yellow syrup. $^1$H NMR (700 MHz, CDCl$_3$): δ=3.56-3.52 (1H, m), 2.69 (1H, q, J=6.2), 2.48 (1H, dd, J=15.0, 3.3), 2.36 (1H, t, J=11.3), 2.22-2.17 (1H, m), 2.05-2.02 (1H, m), 1.99 (1H, dt, J=12.8, 3.3), 1.94-1.87 (2H, m), 1.84-1.69 (6H, m), 1.51-1.44 (3H, m), 1.32-1.09 (6H, m), 1.22 (3H, s), 1.03 (3H, d, J=6.5), 0.98-0.92 (1H, ddd, J=24.4, 12.3, 6.3), 0.86 (1H, q, J=12.6), 0.80 (3H, t, J=7.4), 0.69 (3H, s); $^{13}$C NMR (176 MHz, CDCl$_3$): δ=212.9, 178.8, 71.2, 54.8, 52.0, 50.7, 49.9, 49.0, 43.7, 72.7, 41.2, 38.9, 35.7, 34.2, 33.5, 31.7, 29.8, 28.4, 24.6, 23.5, 21.8, 19.6, 18.8, 12.1, 12.0.

Alternatively, the product of step H can be converted to a compound of general formula (XXI) in which R$^{4'}$ is C(O)OH by reduction, for example with sodium borohydride.

As a person of skill in the art would appreciate, the synthetic route shown in Scheme 5 could be adapted by conversion of the nitrile group to a carboxylic acid at an earlier stage followed, if necessary, by protection of the carboxylic acid group, for example as an ester.

Example 6—Preparation of a Compound of General Formula (IF) with an Aldehyde Side Chain Scheme 7 illustrates a method for converting a compound of general formula (II) with an aldehyde side chain to a compound of general formula (IF) with an aldehyde side chain. The first step of the method is to protect the aldehyde as a dioxolane group. The compound of general formula (II) is then converted sequentially to compounds of general formulae (IA), (IB), (IC), (ID), (IE) and (IF) using the reagents shown in Scheme 7, still with the aldehyde protected. The protection is then removed by treatment with acid.

Scheme 7

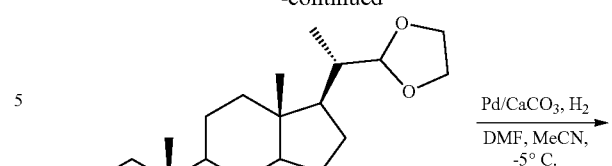

A. Synthesis of (6β, 7α, 20S)-20-(ethylenedioxymethyl)-6-ethyl-7-hydroxy-pregna-4-en-3-one

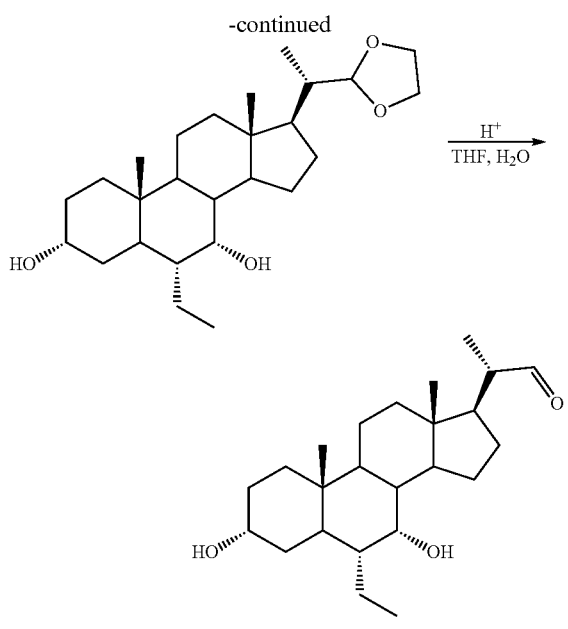

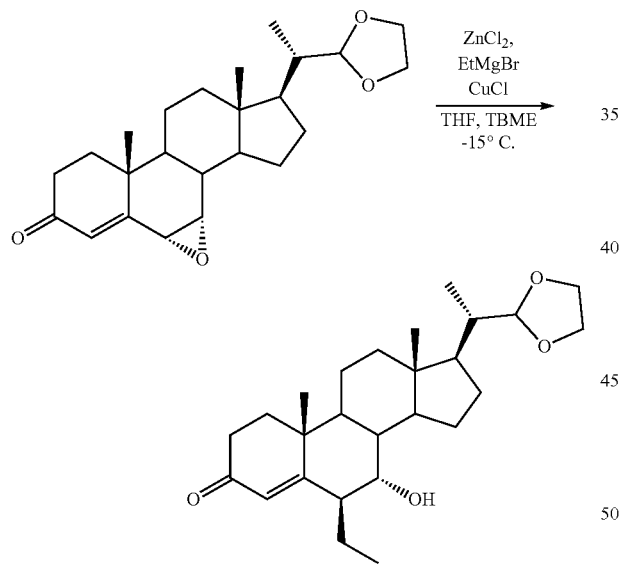

A solution of 0.5M ZnCl$_2$ in THF (3.1 mL) and THF (4 vol, 4 mL) was cooled to −15° C. and a solution of 1M EtMgBr in TBME (4.7 mL) was added dropwise over 10 mins, maintaining the temperature below −12° C. CuCl (13 mg, 0.13 mmol) was then charged in one portion followed by the dropwise addition of a solution of (6α, 7α, 20S)-6,7-epoxy-20-(ethylenedioxymethyl)-pregna-4-en-3-one from Example 1F (1.0 g, 2.6 mmol) in THF (8 vol, 8 mL) over 16 mins, maintaining the temperature below −12° C. The reaction was stirred at −15° C. for 40 mins (TLC, eluant 1:1 EtOAc:Heptane; visualized with Cerium Ammonium Molybdate stain), warmed to ambient temperature and quenched by the dropwise addition of sat. aq. NH$_4$Cl (2.5 vol, 2.5 mL). The reaction mixture was then diluted with EtOAc (50 mL) and washed with sat. aq. NH$_4$Cl (2×50 mL) and water (2×50 mL). The organic phase was dried over Na$_2$SO$_4$, filtered and concentrated in-vacuo at 40° C. Purification by column chromatography gave (6β, 7α, 20S)-20-(ethylenedioxymethyl)-6-ethyl-7-hydroxy-pregna-4-en-3-one as an off white crystalline solid (1.06 g). $^1$H NMR (700 MHz, CDCl$_3$): δ=5.78 (1H, s), 4.85 (1H, d, J=2.0), 3.94 (2H, m), 3.89 (2H, m), 3.74 (1H, m), 2.46 (1H, m), 2.37 (1H, m), 2.31 (1H, m), 2.06-1.93 (3H, m), 1.85-1.68 (4H, m), 1.59 (3H, s), 1.58-1.25 (6H, m), 1.25 (1H, m), 1.22 (3H, s), 1.18 (1H, m), 0.95 (3H, d, J=6.7), 0.91 (3H, t, J=7.4), 0.75 (3H, s). $^{13}$C NMR (176 MHz, CDCl$_3$): δ=199.1, 170.4, 128.7, 106.0, 72.3, 65.2, 65.1, 55.1, 52.3, 49.6, 44.4, 42.9, 39.3, 39.1, 38.3, 37.5, 35.7, 34.1, 27.3, 26.4, 23.9, 20.9, 19.7, 12.8, 11.7, 11.6.

B. Synthesis of (5β, 6β, 7α, 20S)-20-(ethylenedioxymethyl)-6-ethyl-7-hydroxy-pregna-3-one

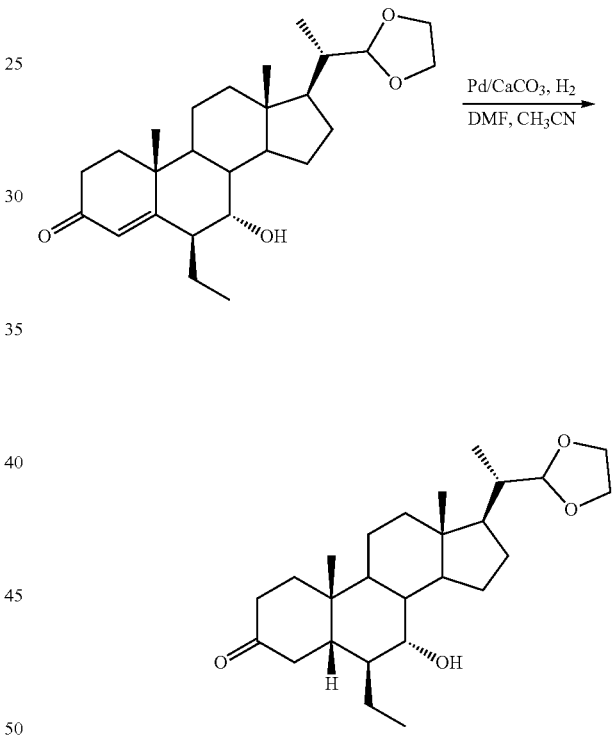

5% Pd on CaCO$_3$ (90 mg, 0.2 mass eq) was charged to a flask under argon, followed by a solution of (6β, 7α, 20S)-20-(ethylenedioxymethyl)-6-ethyl-7-hydroxy-pregna-4-en-3-one (450 mg, 1.1 mmol) in DMF (3 vol, 2.25 mL) and MeCN (6 vol, 84.5 mL). The flask was purged with argon, then and stirred at ambient temperature. After 24 h (TLC, eluant 1:1 EtOAc:Heptane; visualized with Cerium Ammonium Molybdate stain) the reaction mixture was purged with argon and then filtered through a PTFE 0.45 μm filter. The filter was washed with EtOAc (2×25 mL). The organic phase was washed with water (3×25 mL), dried over Na$_2$SO$_4$, filtered and concentrated in-vacuo at 40° C. Purification by column chromatography gave (5β, 6β, 7α, 20S)-20-(ethylenedioxymethyl)-6-ethyl-7-hydroxy-pregna-3-one as an off white crystalline solid (167 mg). $^1$H NMR (700

MHz, CDCl$_3$): δ=4.85 (1H, d, J=2.0), 3.95 (2H, m), 3.85 (2H, m), 3.70 (1H, s), 3.37 (1H, dd, J=13.5, 15.5), 2.37 (1H, m), 2.11 (2H, m), 2.04-1.91 (4H, m), 1.81 (2H, m), 1.62-1.65 (3H, m), 1.55-1.40 (8H, m), 1.31-1.25 (2H, m), 1.18 (1H, m), 1.05 (3H, s), 0.95 (6H, m), 0.72 (3H, s). $^{13}$C NMR (176 MHz, CDCl$_3$): δ=213.8, 106.0, 72.0, 65.2, 65.0, 52.4, 49.7, 49.6, 47.0, 46.8, 43.0, 39.3, 37.7, 36.3, 36.1, 35.8, 34.1, 31.9, 27.7, 27.4, 24.4, 24.0, 22.7, 20.8, 13.9, 11.6.

C. Synthesis of (5β, 6β, 20S)-20-(ethylenedioxymethyl)-6-ethyl-pregna-3,7-dione

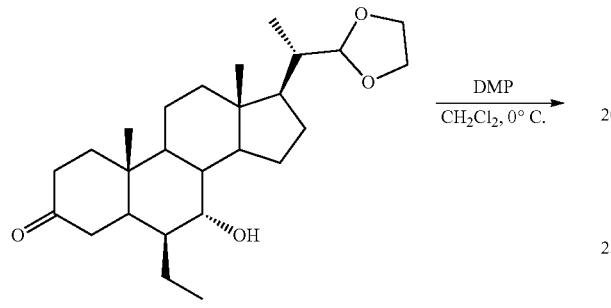

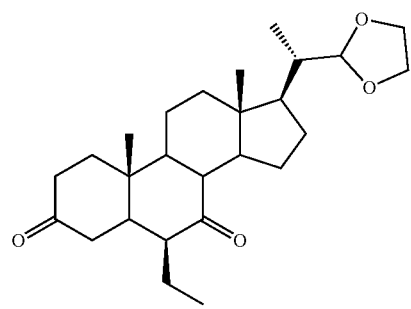

To a solution of (5β, 6β, 7α, 20S)-20-(ethylenedioxymethyl)-6-ethyl-7-hydroxy-pregna-3-one (110 mg, 0.25 mmol) in CH$_2$Cl$_2$ (25 vol, 2.75 mL) under argon was added Dess-Martin periodinane (127 mg, 0.3 mmol). After 30 minutes (TLC, eluant 1:1 EtOAc:Heptane; visualized with Cerium Ammonium Molybdate stain) the reaction mixture was diluted with 10 EtOAc and 10% Na$_2$S$_2$O$_3$/2% NaHCO$_3$ and stirred for 1 h. The phases were separated and the aqueous extracted with EtOAc (10 mL). The combined organic phases were washed with 1M aq. NaOH (10 mL), dried over Na$_2$SO$_4$, filtered and concentrated in-vacuo at 40° C. to give crude (5β, 6β, 20S)-20-(ethylenedioxymethyl)-6-ethyl-pregna-3,7-dione as a white solid (104 mg). $^1$H NMR (700 MHz, CDCl$_3$): δ=4.85 (1H, d, J=2.0), 3.94 (2H, m), 3.84 (2H, m), 2.42 (1H, t, J=11.4), 2.32-2.19 (4H, m), 2.06 (1H, m), 2.02-1.75 (8H, m), 1.65 (1H, m), 1.59-1.39 (6H, m), 1.29-1.17 (2H, m), 1.15 (3H, s), 0.94 (3H, d, J=6.7), 0.84 (3H, t, J=7.3), 0.73 (3H, s). $^{13}$C NMR (176 MHz, CDCl$_3$): δ=214.6, 211.6, 105.9, 65.2, 65.0, 57.1, 51.5, 49.8, 48.4, 47.4, 44.9, 43.6, 43.4, 39.2, 39.0, 35.8, 35.3, 34.9, 27.4, 24.8, 23.8, 23.4, 21.7, 12.6, 12.0, 11.7.

D. Synthesis of (5β, 6α, 20S)-20-(ethylenedioxymethyl)-6-ethyl-pregna-3,7-dione

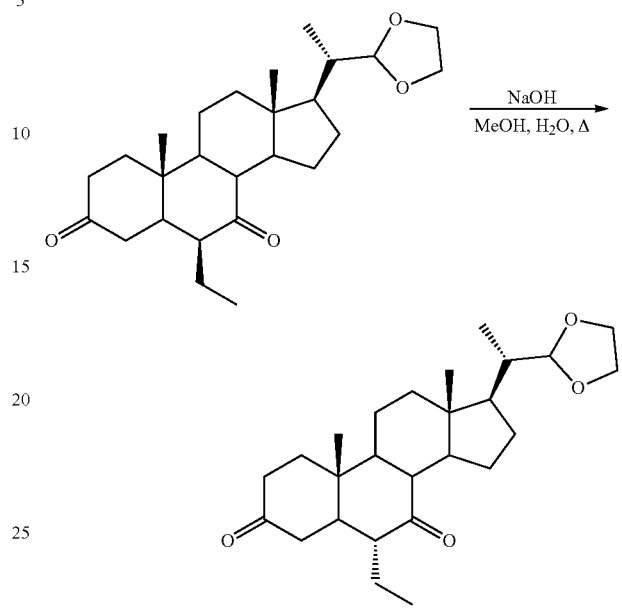

A solution of (5β, 6β, 20S)-20-(ethylenedioxymethyl)-6-ethyl-pregna-3,7-dione (100 mg, 0.3 mmol) in MeOH (20 vol) was warmed to 50° C. and aq. 0.5M NaOH (0.65 mmol) was added. After 16 h (TLC, eluant 1:1 EtOAc:Heptane; visualized with Cerium Ammonium Molybdate stain) the reaction was diluted with EtOAc (10 mL), washed with water (2×10 mL) and then 5% aq. NaCl (1×10 mL). The combined organic phases were washed with 1M aq. NaOH (10 mL), dried over Na$_2$SO$_4$, filtered and concentrated in-vacuo at 40° C. to give (5β, 6α, 20S)-20-(ethylenedioxymethyl)-6-ethyl-pregna-3,7-dione as a clear oil (80 mg). $^1$H NMR (700 MHz, CDCl$_3$): δ=4.85 (1H, d, J=2.0), 3.93 (2H, m), 3.84 (2H, m), 2.74 (1H, q, J=4.6), 2.47 (1H, t, J=11.3), 2.30-2.16 (4H, m), 2.10-2.02 (3H, m), 1.98 (1H, m), 1.91-1.79 (3H, m), 1.72 (5H, m), 1.47-1.37 (2H, m), 1.33 (3H, s), 1.23 (1H, m), 1.07 (1H, m), 0.98 (1H, m), 0.94 (3H, d, J=6.7), 0.81 (3H, t, J=7.4), 0.71 (3H, s). $^{13}$C NMR (176 MHz, CDCl$_3$): δ=212.0, 210.6, 105.9, 65.2, 65.0, 52.3, 52.2, 51.3, 50.0, 48.4, 43.7, 42.9, 39.1, 38.7, 38.3, 36.7, 35.9, 35.5, 27.5, 24.7, 22.9, 22.2, 18.6, 11.9, 11.8, 11.7.

E. Synthesis of (3α, 5β, 6α, 20S)-6-ethyl-3-hydroxy-20-(ethylenedioxymethyl)-pregna-7-one

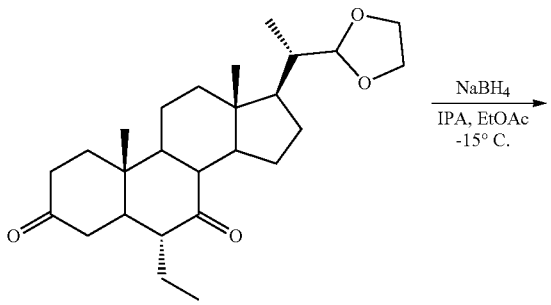

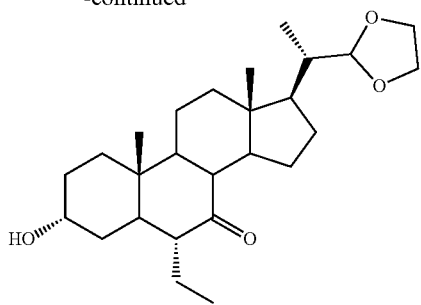

NaBH$_4$ (80 mg, 0.2 mmol) in IPA (1.6 mL) was cooled to −15° C. (5β, 6α, 20S)-20-(ethylenedioxymethyl)-6-ethyl-pregna-3,7-dione (80 mg, 0.2 mmol) in EtOAc (1.6 mL) was added dropwise over 10 mins. After 30 mins (TLC, eluant 1:1 EtOAc:Heptane; visualized with Cerium Ammonium Molybdate stain) the reaction was warmed to ambient temperature and quenched by the addition of 0.7M aq. H$_2$SO$_4$ (7 vol) dropwise over 5 mins. The reaction mixture was diluted with EtOAc (10 mL) and the organic phase was washed with water (3×5 mL) and 5% aq. NaCl (1×5 mL). The organic phase was dried over Na$_2$SO$_4$, filtered and concentrated in-vacuo at 40° C. to give (3α, 5β, 6α, 20S)-6-ethyl-3-hydroxy-20-(ethylenedioxymethyl)-pregna-7-one as a clear oil (60 mg). $^1$H NMR (700 MHz, CDCl$_3$): δ=4.85 (1H, d, J=1.9), 3.93 (2H, m), 3.84 (2H, m), 3.52 (1H, m), 2.69 (1H, dd, J=5.7, 12.9), 2.21 (1H, m), 2.0-1.92 (2H, m), 1.86-1.67 (8H, m), 1.51-1.34 (6H, m), 1.25 (2H, m), 1.21 (3H, s), 1.20-1.10 (3H, m), 0.93 (3H, d, J=6.7), 0.88 (1H, m), 0.80 (3H, t, J=7.4), 1.66 (3H, s). $^{13}$C NMR (176 MHz, CDCl$_3$): δ=212.7, 106.0, 71.2, 65.3, 65.0, 52.0, 51.3, 50.7, 50.0, 48.5, 43.7, 43.0, 39.2, 38.8, 35.7, 34.3, 31.8, 29.9, 27.6, 24.9, 23.5, 21.9, 18.8, 12.0, 11.9, 11.7;

F. Synthesis of (3α, 5β, 6α, 7α, 20S)-6-ethyl-3,7-dihydroxy-20-(ethylenedioxymethyl)-pregnane

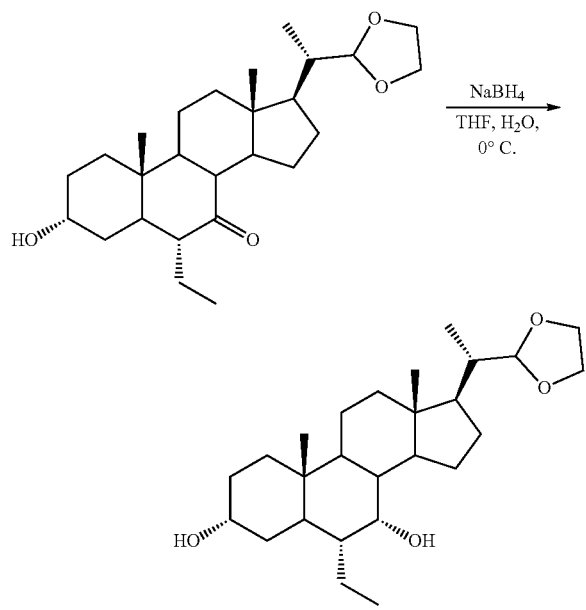

To a solution (3α, 5β, 6α, 20S)-6-ethyl-3-hydroxy-20-(ethylenedioxymethyl)-pregna-7-one (60 mg, 0.14 mmol) in THF (5 mL) and water (1.25 mL) at 0° C., was added NaBH$_4$ (53 mg, 1.4 mmol) in one portion. After 2 h (TLC, eluant 1:1 EtOAc:Heptane; visualized with Cerium Ammonium Molybdate stain) the reaction was allowed to warm up to ambient temperature and was quenched by the addition of 1:1 MeOH:H$_2$O (2 mL), followed by 2M aq. H$_2$SO$_4$ (1 mL) dropwise over 5 mins. The reaction mixture was diluted with EtOAc (20 mL) and washed with water (3×20 mL). The aqueous phase was extracted with EtOAc (20 mL) and the combined organic phases washed with 5% aq. NaCl (1×5 mL). The organic phase was dried over Na$_2$SO$_4$, filtered and concentrated in-vacuo at 40° C. to give (3α, 5β, 6α, 7α, 20S)-6-ethyl-3,7-dihydroxy-20-(ethylenedioxymethyl)-pregnan as a clear oil (58 mg). $^1$H NMR (700 MHz, CDCl$_3$): δ=4.85 (1H, d, J=2.0), 3.94 (2H, m), 3.84 (2H, m), 3.40 (1H, m), 2.00-1.91 (2H, m), 1.80-1.75 (5H, m), 1.70-1.63 (2H, m), 1.61-1.56 (1H, m), 1.53-1.12 (15H, m), 1.01 (1H, m), 0.94 (3H, d, J=6.7), 0.90 (5H, m), 0.67 (3H, s). $^{13}$C NMR (176 MHz, CDCl$_3$): δ=104.9, 71.2, 69.7, 64.1, 63.9, 51.1, 48.8, 44.1, 41.9, 40.0, 39.0, 38.3, 38.2, 34.4, 34.3, 32.8, 32.1, 29.5, 26.3, 22.8, 22.0, 21.1, 19.6, 10.5, 10.4, 10.4.

G. Synthesis of (3α, 5β, 6α, 7α)-6-ethyl-3,7-dihydroxy-23,24-dinor-cholane-22-al

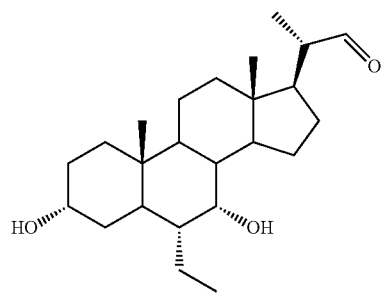 [SMILES: CC[C@@H]1C2C[C@H](O)CC[C@]2(C)C2CC[C@@]3(C)C(CC[C@@H]3[C@H](C)C=O)C2[C@@H]1O]

(3α, 5β, 6α, 7α, 20S)-6-ethyl-3,7-di hydroxy-20-(ethylenedioxymethyl)-pregnan (58 mg, 0.14 mmol) in MeCN (1 mL, 17 vol), H$_2$O (0.29 mL, 5 vol) and TFA (0.29 mL, 5 vol) was heated to reflux. After 2 h (TLC, eluant 1:1 EtOAc: Heptane; visualized with Anisaldehyde stain) the reaction mixture was poured onto 5% aq. NaHCO$_3$ (30 mL) and diluted with CH$_2$Cl$_2$ (10 mL). After stirring for 15 minutes the phases were separated and the aqueous phase extracted with CH$_2$Cl$_2$ (2×100 mL). The combined organic phases were dried over Na$_2$SO$_4$, filtered and concentrated in-vacuo at 40° C. to give (3α, 5β, 6α, 7α)-6-ethyl-3,7-dihydroxy-23,24-dinor-cholane-22-al as a mixture of C20 epimers as a clear oil (51 mg). NMR data matches an authentic sample of (3α, 5β, 6α, 7α)-6-ethyl-3,7-dihydroxy-23,24-dinor-cholane-22-al.

The compound of general formula (IF) with the aldehyde side chain can then be converted to a compound of general formula (XXI) in which —YR$^{4a}$ is C(O)OH by oxidation using any appropriate method. In one such method, the aldehyde could be directly oxidised to the acid using a Jones reaction or KMnO$_4$. Alternatively, if chain extension is required, an olefination reaction followed by saponification will provide a compound in which R$^{4a}$ is C(O)OH but in which Y has been extended as shown in Example 7.

Example 7—Preparation of a Compound of General Formula (XXI) Via Compounds of General Formula (I) with OH and Aldehyde Side Chain
Scheme 8 below shows a method for the conversion of a compound of general formula (II) in which —YR$^4$ is —CH$_2$OH to a compound of general formula (XXI) in which —YR$^{4a}$ is CH$_2$CH$_2$C(O)OH
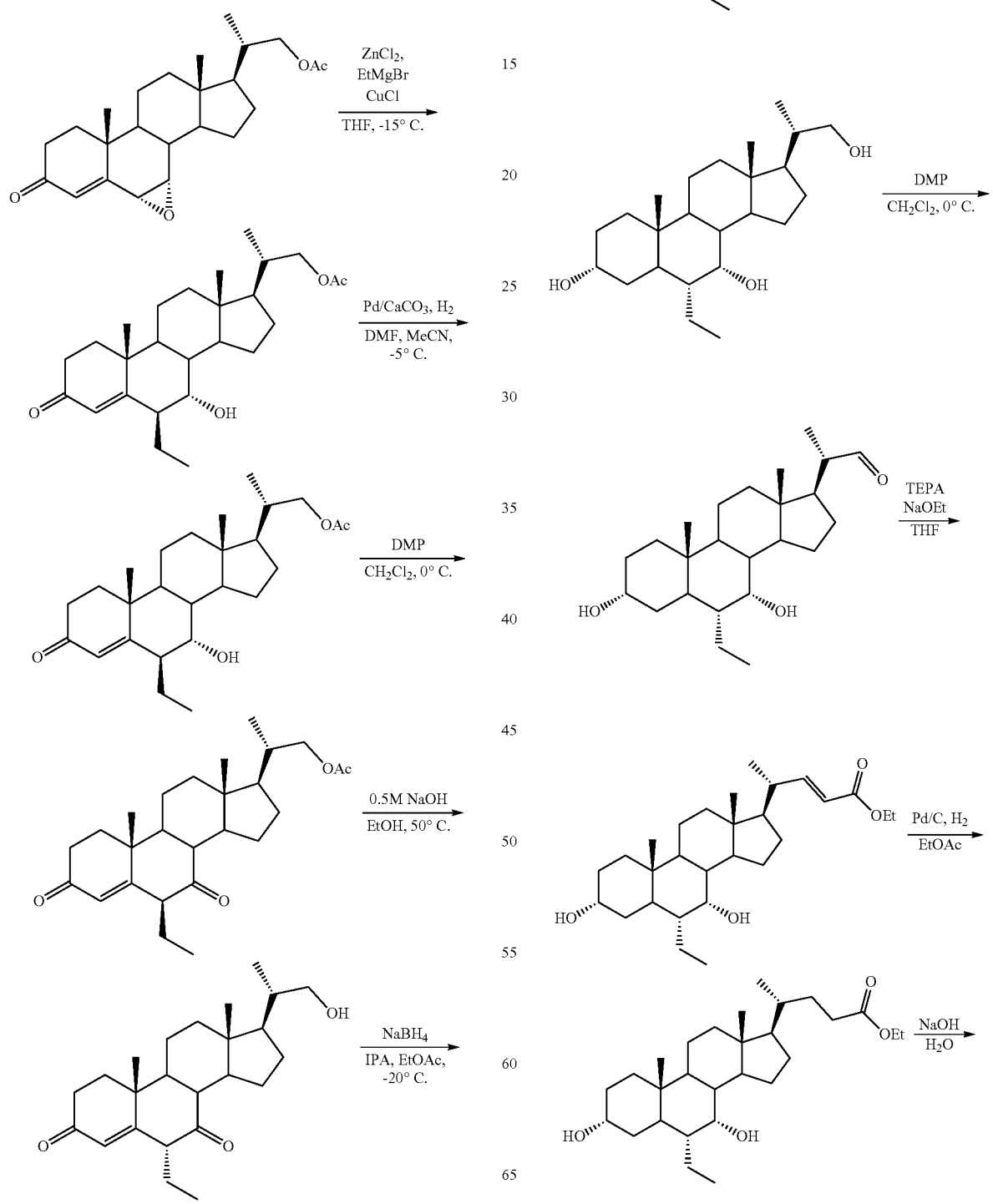

A. Synthesis of (6β, 7α, 20S)-20-acetoxymethyl-6-ethyl-7-hydroxy-pregna-4-en-3-one

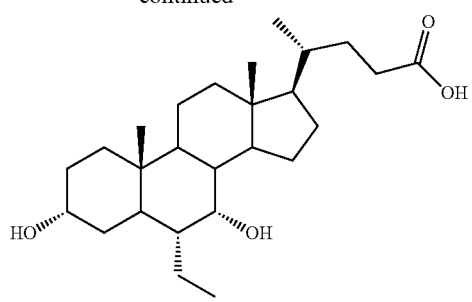

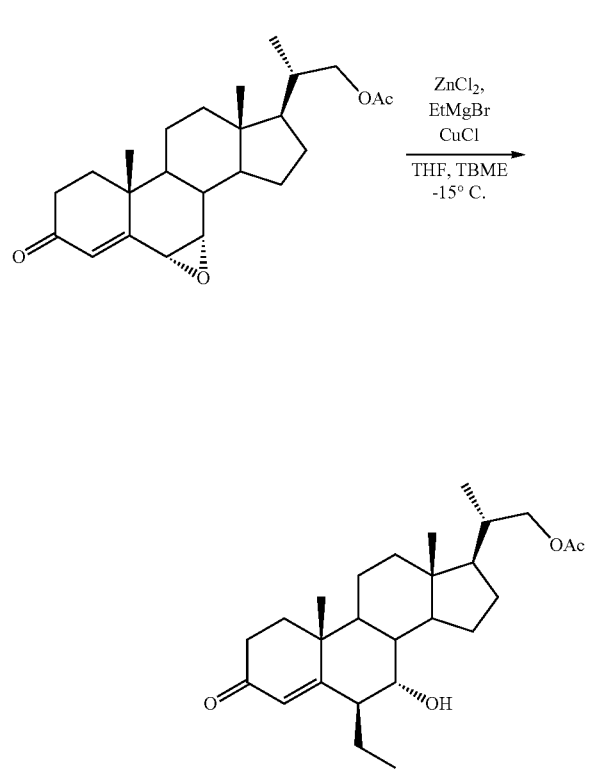

A solution of 0.5 M ZnCl₂ in THF (20.2 mL) was charged to a reaction vessel under argon followed by THF (4 vol, 26 mL) and cooled to −15° C. A solution of 1 M EtMgBr in TBME (27 mL) was charged over 10 mins whilst maintaining the temperature below −12° C. CuCl (84 mg, 0.84 mmol) was then charged in one portion. (6α, 7α, 20S)-6,7-epoxy-20-acetoxymethyl-pregna-4-en-3-one (6.5 g, 16.8 mmol) in THF (8 vol, 16 mL) was charged to the reaction vessel over 16 mins while maintaining the temperature below −12° C. and the reaction warmed to ambient temperature and stirred for 90 mins. The reaction mixture was quenched by the dropwise addition of sat. aq. NH₄Cl (2.5 vol, 17 mL). The reaction mixture was filtered and the filtrate washed with sat. aq. NH₄Cl (2×50 mL) and 5% aq. NaCl (2×50 mL). The organic phase was dried over Na₂SO₄, filtered and concentrated in-vacuo at 40° C. The crude (6β, 7α, 20S)-20-acetoxymethyl-6-ethyl-7-hydroxy-pregna-4-en-3-one (6.7 g) was taken on to the next step with no further purification. ¹H NMR (700 MHz, CDCl₃): δ=5.77 (1H, s), 4.07 (1H, dd, J=10.6, 3.1), 3.79 (1H, dd, J=10.6, 7.4), 3.74 (1H, s), 2.47 (1H, m), 2.37 (1H, m), 2.32 (1H, t, J=8.1), 2.05 (3H, s), 2.04-1.98 (3H, m), 1.90-1.65 (5H, m), 1.60-1.35 (7H, m), 1.30-1.15 (6H, m), 1.02 (3H, d, J=6.6), 0.91 (3H, t, J=7.3), 0.76 (3H, s); ¹³C NMR (176 MHz, CDCl₃): δ=199.2, 171.4, 170.9, 128.5, 72.1, 69.4, 55.3, 52.6, 49.9, 44.2, 42.6, 39.0, 38.3, 37.4, 35.8, 35.6, 34.1, 27.6, 26.3, 23.7, 21.0, 20.8, 19.7, 17.1, 12.8, 11.9.

B. Synthesis of (5β, 6β, 7α, 20S)-20-acetoxymethyl-6-ethyl-7-hydroxy-pregna-3-one

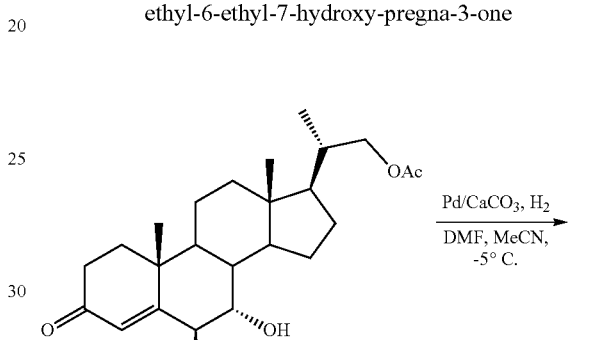

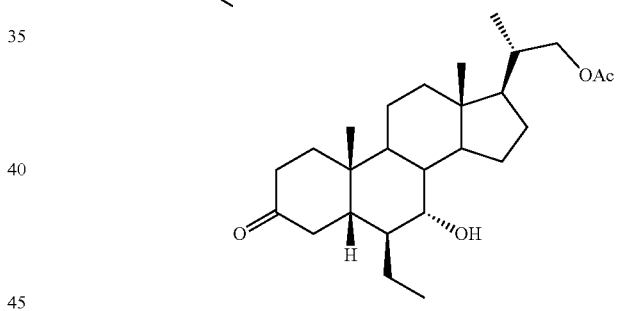

5% Pd/CaCO₃ (274 mg, 0.2 mass eq) was charged to a flask under argon. (6β, 7α, 20S)-20-acetoxymethyl-6-ethyl-7-hydroxy-pregna-4-en-3-one (1.37 g, 3.3 mmol) in DMF (3 vol, 4.1 mL) was charged followed by MeCN (6 vol, 8.2 mL). The flask was purged with argon, purged with hydrogen and stirred at RT. After 24 h, the reaction mixture was purged with argon and filtered through Whatman® GF/B grade filter pad (glass fiber pore size 1 μm) filter pad. The solids were washed with EtOAc (2×25 mL). The filtrate was then washed with H₂O (3×30 mL), dried over Na₂SO₄ and concentrated in-vacuo at 40° C. Purification by column chromatography gave (5β, 6β, 7α, 20S)-20-acetoxymethyl-6-ethyl-7-hydroxy-pregna-3-one as an off white crystalline solid (0.96 g, 69%). ¹H NMR (700 MHz, CDCl₃): δ=4.08 (1H, dd, J=10.7, 3.4), 3.79 (1H, dd, J=10.7, 7.3), 3.71 (1H, s), 3.36 (1H, dd, J=15.5, 13.5), 2.36 (1H, td, J=14.1, 4.6), 2.11 (1H, m), 2.06 (3H, s), 2.03-1.10 (21H, m), 1.05 (3H, s), 1.03 (3H, d, J=6.6), 0.94 (3H, t, J=7.1), 0.73 (3H, s); ¹³C NMR (176 MHz, CDCl₃): δ=213.7, 171.4, 72.0, 69.5, 52.7, 49.9, 49.8, 47.0, 46.7, 42.8, 39.3, 37.7, 36.3, 36.0, 35.8, 35.7, 34.2, 27.7, 27.6, 24.4, 23.9, 21.0, 20.8, 17.2, 13.9, 11.8.

C. Synthesis of (5β, 6β, 20S)-6-ethyl-3,7-dioxo-23,24-dinor-cholane-22-ol acetate [or (5β, 6β, 20S)-20-acetoxymethyl-6-ethyl-pregna-3,7-dione]

D. Synthesis of (5β, 6α, 20S)-6-ethyl-3,7-dioxo-23,24-dinor-cholane-22-ol [or (5β, 6α, 20S)-6-ethyl-20-hydroxymethyl-pregna-3,7-dione]

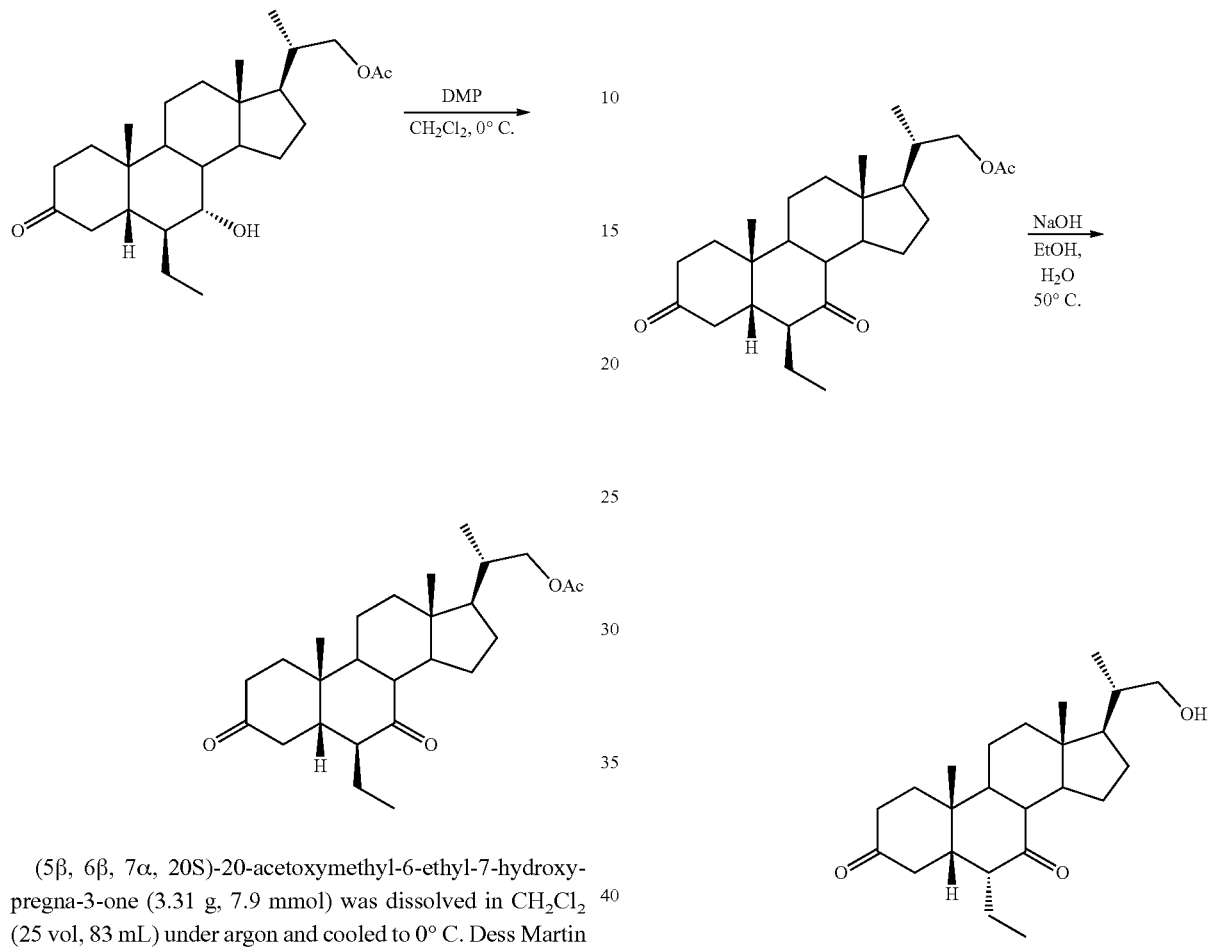

(5β, 6β, 7α, 20S)-20-acetoxymethyl-6-ethyl-7-hydroxy-pregna-3-one (3.31 g, 7.9 mmol) was dissolved in CH$_2$Cl$_2$ (25 vol, 83 mL) under argon and cooled to 0° C. Dess Martin periodane (4.0 g, 9.5 mmol) was charged in portions over 5 mins. After 20 mins the reaction was quenched by the addition of 10% aq. Na$_2$SO$_4$/2% aq. NaHCO$_3$ (20 mL) and the mixture stirred for 20 mins. The solution was diluted with EtOAc (100 mL) and H$_2$O (100 mL). The aqueous layer was separated and extracted with EtOAc (100 mL). The combined organic layers were washed with 1M aq. NaOH (50 mL), then 5% aq. NaCl (50 mL) and the resulting cloudy solution passed through a silica plug and washed with EtOAc (2×100 mL). Concentration in-vacuo at 40° C. followed by purification by column chromatography gave (5β, 6β, 20S)-6-ethyl-3,7-dioxo-23,24-dinor-cholane-22-ol acetate as a white crystalline solid (2.39 g, 73%). $^1$H NMR (700 MHz, CDCl$_3$): δ=4.08 (1H, dd, J=10.7, 3.4), 3.79 (1H, dd, J=10.7, 7.4), 2.44 (1H, t, J=11.4), 2.31-2.19 (4H, m), 2.05 (3H, s), 2.00 (1H, m), 1.92-1.71 (6H, m), 1.65 (1H, m), 1.59-1.47 (3H, m), 1.39-1.17 (7H, m), 1.16 (3H, s), 1.03 (3H, d, J=6.7), 0.85 (3H, t, J=7.4), 0.75 (3H, s); $^{13}$C NMR (176 MHz, CDCl$_3$): δ=214.6, 211.6, 171.3, 69.4, 57.3, 52.0, 50.0, 48.5, 47.3, 44.9, 43.6, 43.2, 39.0, 35.8, 35.7, 35.3, 35.0, 27.7, 24.7, 23.8, 23.5, 21.7, 21.0, 17.2, 12.6, 12.2.

To a suspension of (5β, 6β, 20S)-6-ethyl-3,7-dioxo-23,24-dinor-cholane-22-ol acetate (1.77 g, 4.2 mmol) in EtOH (12 vol, 21.5 mL) at 50° C. was added dropwise 0.5M aq. NaOH (18.9 mL, 9.45 mmol). The reaction was heated at 50° C. for 16 h, then cooled to ambient temperature, diluted with H$_2$O (50 mL) and extracted with EtOAc (50 mL). The phases were separated and the aqueous phase extracted with EtOAc (2×50 mL). The combined organic phases were washed with 5% aq. NaCl (2×50 mL), dried over Na$_2$SO$_4$, filtered and concentrated in-vacuo at 40° C. Purification by column chromatography gave (5β, 6α, 20S)-6-ethyl-3,7-dioxo-23,24-dinor-cholane-22-ol as a white crystalline solid (1.35 g, 86%). $^1$H NMR (700 MHz, CDCl$_3$): δ=3.64 (1H, dd, J=10.4, 2.9), 3.37 (1H, dd, J=10.3, 7.1), 2.69 (1H, m), 2.47 (1H, t, J=11.3), 2.30-2.16 (5H, m), 2.10-2.03 (2H, m), 1.94-1.80 (3H, m), 1.72-1.49 (6H, m), 1.43 (1H, br.s), 1.33 (3H, s), 1.32-1.17 (3H, m), 1.06 (3H, d, J=6.7), 0.98 (1H, m), 0.81 (3H, t, J=7.4), 0.71 (3H, s); $^{13}$C NMR (176 MHz, CDCl$_3$): δ=212.1, 210.6, 67.8, 52.4, 52.2, 51.5, 50.0, 48.7, 43.7, 42.7, 38.8, 38.6, 38.3, 36.7, 35.9, 35.5, 27.9, 24.7, 22.9, 22.3, 18.6, 16.8, 12.2, 11.8.

E. Synthesis of (3α, 5β, 6α, 20S)-6-ethyl-3-hydroxy-7-oxo-23, 24-dinor-cholane-22-ol [or (3α, 5β, 6α, 20S)-6-ethyl-3-hydroxy-20-hydroxymethyl-pregna-7-one]

F. Synthesis of (3α, 5β, 6α, 7α, 20S)-6-ethyl-3,7-dihydroxy-23,24-dinor-cholane-22-ol (or (3α, 5β, 6α, 7α, 20S)-6-ethyl-3,7-dihydroxy-20-hydroxymethyl-pregnan)

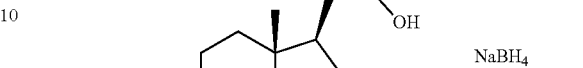

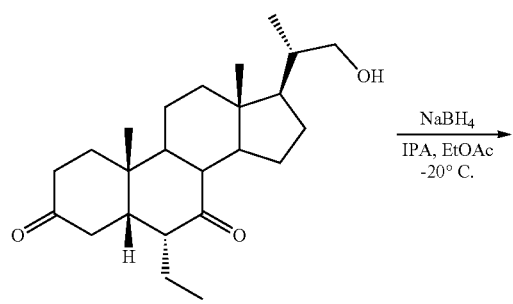

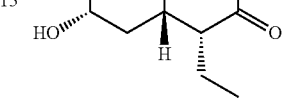

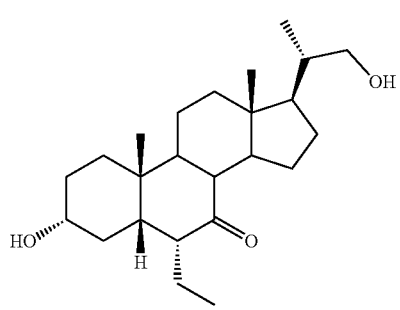

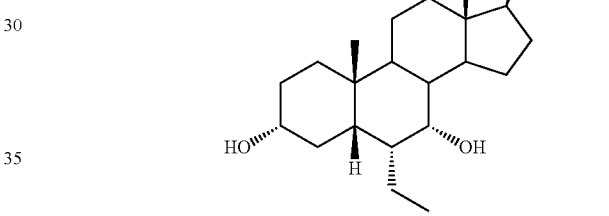

(3α, 5β, 6α, 20S)-6-ethyl-3-hydroxy-7-oxo-23,24-dinor-cholane-22-ol (0.83 g, 2.2 mmol) in THF (30 mL) and water (7.5 mL) was cooled to 0° C. and NaBH$_4$ (830 mg, 22 mmol) added in 4 portions over 15 mins. After 2 h the reaction was warmed to room temperature and quenched by the addition of 1:1 MeOH:H$_2$O (15 mL) followed by the dropwise addition of 2M aq. H$_2$SO$_4$ (11 mL) over 10 mins. The reaction mixture was diluted with EtOAc (100 mL) and washed with H$_2$O (100 mL). The aqueous phase was extracted with EtOAc (3×100 mL) and the combined organic phases were washed with 5% aq. NaCl (3×100 mL). The organic phase was dried over Na$_2$SO$_4$, filtered and concentrated in-vacuo at 40° C. to give (3α, 5β, 6α, 7α, 20S)-6-ethyl-3,7-dihydroxy-23,24-dinor-cholane-22-ol as a white solid (0.53 g, 64%). $^1$H NMR (700 MHz, MeOD): δ=3.64 (1H, s), 3.57 (1H, dd, J=10.6, 3.1), 3.30 (1H, m), 3.23 (1H, dd, J=10.5, 7.4), 2.00 (1H, m), 1.90-1.70 (6H, m), 1.59 (1H, m), 1.57-1.44 (6H, m), 1.42-1.27 (5H, m), 1.21 (2H, m), 1.13 (1H, m), 1.04 (3H, d, J=6.6), 1.00 (1H, m), 0.91 (3H, s), 0.90 (3H, t, J=7.7), 0.71 (3H, s); $^{13}$C NMR (176 MHz, MeOD): δ=71.7, 69.7, 66.5, 52.5, 50.0, 45.5, 42.3, 41.7, 40.1, 39.5, 38.8, 35.3, 35.1, 33.1, 32.9, 29.8, 27.5, 23.2, 22.3, 22.0, 20.5, 15.9, 10.9, 10.6.

NaBH$_4$ (136 mg, 3.6 mmol) in IPA (6.5 vol, 9 mL) was cooled to −15° C., then a solution of (5β, 6α, 20S)-6-ethyl-3,7-dioxo-23,24-dinor-cholane-22-ol (1.35 g, 0.3.6 mmol) in EtOAc (6.5 vol, 9 mL) was added dropwise over 10 mins. After 20 mins the reaction was warmed to ambient temperature and quenched by the dropwise addition of 0.7M aq. H$_2$SO$_4$ (7 vol, 9.45 mL) over 10 mins. The reaction mixture was diluted with EtOAc (50 mL) and the organic phase washed with H$_2$O (3×50 mL) and 5% aq. NaCl (50 mL). The organic phase was dried over Na$_2$SO$_4$, filtered and concentrated in-vacuo at 40° C. Purification by column chromatography and concentration in-vacuo at 40° C. gave (3α, 5β, 6α, 20S)-6-ethyl-3-hydroxy-7-oxo-23,24-dinor-cholane-22-ol as a white crystalline solid (0.83 g, 61%). $^1$H NMR (700 MHz, CDCl$_3$): δ=3.64 (1H, dd, J=10.5, 3.2), 3.53 (1H, m), 3.35 (1H, dd, J=10.4, 7.1), 2.69 (1H, m), 2.35 (1H, t, J=11.2), 2.20 (1H, m), 2.00 (1H, m), 1.92-1.67 (8H, m), 1.57-1.43 (3H, m), 1.34-1.23 (2H, m), 1.23 (3H, s), 1.21-1.10 (4H, m), 1.04 (3H, d, J=6.6), 0.98-0.83 (2H, m), 0.80 (3H, t, J=7.4), 0.67 (3H, s); $^{13}$C NMR (176 MHz, CDCl$_3$): δ=212.9, 71.2, 67.9, 52.0, 51.6, 50.7, 50.0, 48.8, 43.7, 42.8, 38.9, 38.7, 35.7, 34.3, 31.8, 29.6, 27.9, 24.8, 23.5, 21.9, 18.8, 16.8, 12.1, 12.0.

G. Synthesis of (3α, 5β, 6α, 7α)-6-ethyl-3,7-dihydroxy-23,24-dinor-cholane-22-al

H. Synthesis of (3α, 5β, 6α, 7α)-6-ethyl-3,7-dihydroxy-22-cholen-24-oic Acid Ethyl Ester

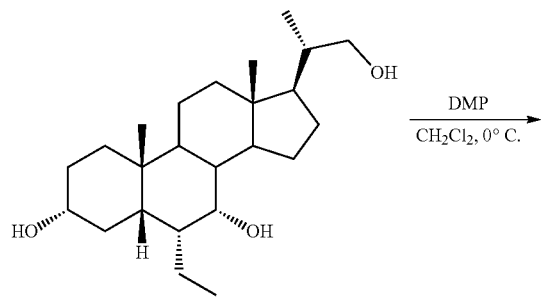

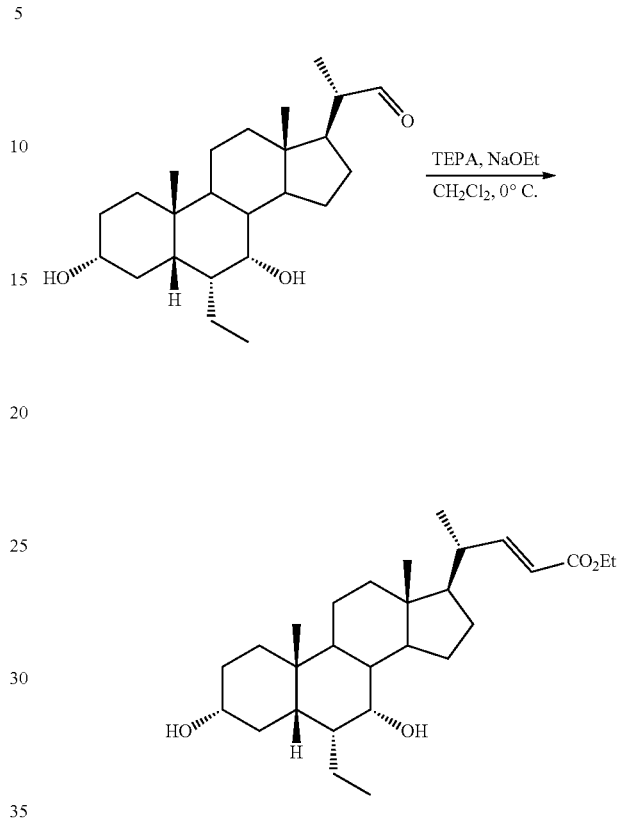

(3α, 5β, 6α, 7α, 20S)-6-ethyl-3,7-dihydroxy-23,24-dinor-cholane-22-ol (421 mg, 1.11 mmol) in DMF (50 vol, 20 mL) was cooled to 0° C. Dess Martin periodinane (473 mg, 1.12 mmol) was charged in portions. After 2.5 h (TLC, eluant 7:3 EtOAc:Heptane; visualized with Cerium Ammonium Molybdate stain), the reaction was quenched by the addition of 10% aq. $NaHSO_3$/2% aq. $NaHCO_3$ (5 mL) and the mixture stirred for 10 mins. The mixture was diluted with EtOAc (100 mL) and 5% NaCl (5 mL). The aqueous layer was extracted with EtOAc (50 mL). The combined organic phases were washed with 2M aq. NaOH (50 mL) and 5% aq. NaCl (4×50 mL), dried over $Na_2SO_4$, filtered and concentrated in-vacuo at 40° C. Purification by column chromatograph gave (3α, 5β, 6α, 7α)-6-ethyl-3,7-dihydroxy-23,24-dinor-cholane-22-al as a 3:1 mixture with (5β, 6α, 7α)-6-ethyl-7-hydroxy-7-oxo-23,24-dinor-cholane-22-al (white foam, 230 mg). $^1H$ NMR (700 MHz, $CDCl_3$): δ=9.56 (1H, d, J=3.4), 3.71 (1H, br. s), 3.44-3.36 (1H, m), 2.38-2.33 (1H, m), 1.94-1.86 (2H, m), 1.83-1.81 (2H, m), 1.80-1.78 (2H, m), 1.74-1.36 (10H, m), 1.34-1.18 (8H, m), 1.14 (3H, d, J=6.8), 0.91 (3H, s), 0.88 (3H, t, J=7.07), 0.71 (3H, s). $^{13}C$ NMR (176 MHz, $CDCl_3$): δ=205.1, 72.3, 70.9, 51.0, 49.9, 49.5, 45.1, 43.3, 41.2, 40.0, 39.3, 35.6, 35.5, 34.0, 33.4, 30.6, 27.1, 24.1, 23.1, 22.2, 20.7, 13.5, 12.2, 11.6.

The HWE reagent was prepared by dropwise addition of TEPA (262 µL, 1.32 mmol) to NaOEt (91 mg, 1.3 mmol) in $CH_2Cl_2$ (2 mL) at 0° C. The reaction mixture was added dropwise over 10 minutes to a solution of (3α, 5β, 6α, 7α)-6-ethyl-3,7-dihydroxy-23,24-dinor-cholane-22-al (199 mg, 0.528 mmol) in $CH_2Cl_2$ (4 mL) at 0° C. The reaction was warmed to ambient temperature and stirred for 1 hour (TLC, eluant 1:1 EtOAc:Heptane; visualized with Cerium Ammonium Molybdate stain). The mixture was diluted with $H_2O$ (20 mL) and $CH_2Cl_2$ (15 mL). The aqueous layer was separated and extracted with $CH_2Cl_2$ (3×20 mL). The combined organic phases were dried over $Na_2SO_4$, filtered and concentrated. Purification by column chromatography gave (3α, 5β, 6α, 7α)-6-ethyl-3,7-dihydroxy-22-cholen-24-oic acid ethyl ester as a white foam (158 mg). The isolated product is a 4:1 mixture of the desired (3α, 5β, 6α, 7α)-6-ethyl-3,7-dihydroxy-22-cholen-24-oic acid ethyl ester and (5β, 6α, 7α)-6-ethyl-7-hydroxy-3-oxo-22-cholen-24-oic acid ethyl ester. $^1H$ NMR (700 MHz, $CDCl_3$): δ=6.83 (1H, dd, J=9.0, 15.6), 5.73 (1H, d, J=15.3), 4.17 (2H, q, J=7.1), 3.69 (1H, m), 3.40 (1H, m), 2.30-2.25 (1H, m), 1.92 (1H, m), 1.85-1.76 (2H, m), 1.76-1.62 (5H, m), 1.59 (1H, m), 1.54-1.34 (7H, m), 1.29 (3H, t, J=7.1), 1.33-1.23 (6H, m), 1.09 (3H, d, J=6.6), 0.90 (3H, s), 0.90 (3H, t, J=7.4), 0.68 (3H, s). $^{13}C$ NMR (176 MHz, $CDCl_3$): δ=167.1, 154.7, 119.0, 72.3, 70.8, 60.1, 54.9, 50.4, 45.2, 43.0, 41.0, 40.1, 39.8, 39.5, 35.6, 35.5, 34.0, 33.3, 30.6, 28.2, 23.7, 23.1, 22.2, 20.7, 19.3, 14.3, 12.1, 11.7.

I. (3α, 5β, 6α, 7α)-6-ethyl-3,7-dihydroxy-cholan-24-oic Acid Ethyl Ester

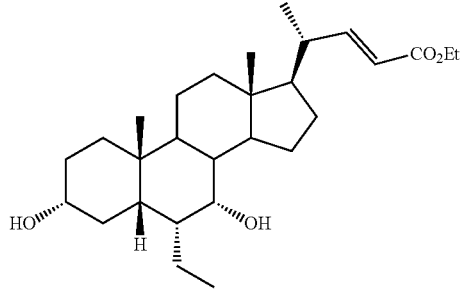

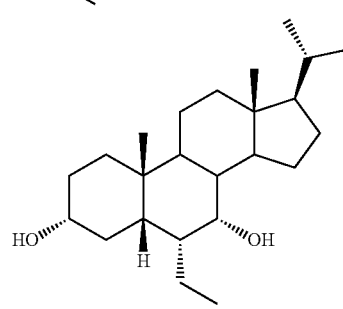

10% Palladium on Carbon (79 mg) was charged to a flask under argon. A solution of (3α, 5β, 6α, 7α)-6-ethyl-3,7-dihydroxy-22-cholen-24-oic acid ethyl ester (135 mg, 0.312 mmol) in EtOAc (51 vol, 7.0 mL) was charged and purged with H$_2$. After 70 h (TLC, eluent 1:1 EtOAc:Heptane; visualized with Anisaldehyde stain) the reaction mixture was filtered through a 0.45 μm PTFE filter and the filter washed with EtOAc (10 mL). Concentration in-vacuo at 40° C. gave (3α, 5β, 6α, 7α)-6-ethyl-3,7-dihydroxy-cholan-24-oic acid ethyl ester (134 mg) as a 4:1 mixture with (5β, 6α, 7α)-6-ethyl-7-hydroxy-3-oxo-cholan-24-oic acid ethyl ester. $^1$H NMR (500 MHz, CDCl$_3$): δ=4.13 (2H, q, J=7.2), 3.46-3.37 (1H, m), 2.41-2.32 (1H, m), 2.28-2.19 (1H, m), 1.89-1.76 (6H, m), 1.76-1.57 (5H, m), 1.54-1.34 (12H, m), 1.27 (3H, t, J=7.1), 1.25-1.12 (4H, m), 0.98-0.88 (9H, m), 0.68 (3H, s). $^{13}$C NMR (126 MHz, CDCl$_3$): δ=167.1, 154.7, 119.0, 72.3, 70.8, 60.1, 54.9, 50.4, 45.2, 43.0, 41.0, 40.1, 39.8, 39.5, 35.6, 35.5, 34.0, 33.3, 30.6, 28.2, 23.7, 23.1, 22.2, 20.7, 19.3, 14.3, 12.1, 11.7.

J. Synthesis of (3α, 5β, 6α, 7α)-6-ethyl-3,7-dihydroxy-cholan-24-oic Acid (Obeticholic Acid)

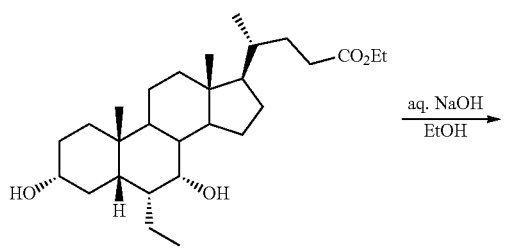

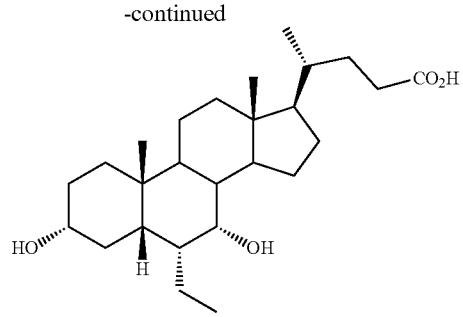

To (3α, 5β, 6α, 7α)-6-ethyl-3,7-dihydroxy-cholan-24-oic acid ethyl ester (118 mg, 0.272 mmol) in EtOH (34 vol, 4 mL) at 50° C., was added 0.5M aq. NaOH (1.2 mL, 0.61 mmol) dropwise. The reaction mixture was stirred at 50° C. for 2.5 h (TLC, eluent 1:1 EtOAc:Heptane; visualized with Cerium Ammonium Molybdate stain) and then 0.5M aq. NaOH (1 mL, 0.5 mmol) was added. After 1 h, the reaction was quenched with 3M aq. HCl (2 mL). The aqueous phase was separated and extracted with EtOAc (3×15 mL). The combined organic phases were dried over Na$_2$SO$_4$, filtered and concentrated in-vacuo at 40° C. Purification by column chromatography gave (3α, 5β, 6α, 7α)-6-ethyl-3,7-dihydroxy-cholan-24-oic acid (108 mg, white foam) as a 4:1 mixture with (5β, 6α, 7α)-6-ethyl-7-hydroxy-3-oxo-cholan-24-oic acid. NMR data was consistent with an authentic sample of OCA.

Alternatively, the product of step E can be converted to (3α, 5β, 6α)-6-ethyl-3-hydrox-7-oxo-cholan-24-oic acid via a 7-oxo intermediate with an aldehyde substituent on the side chain.

K. Synthesis of (3α, 5β, 6α)-6-ethyl-3-hydroxy-7-oxo-23,24-dinor-cholane-22-al

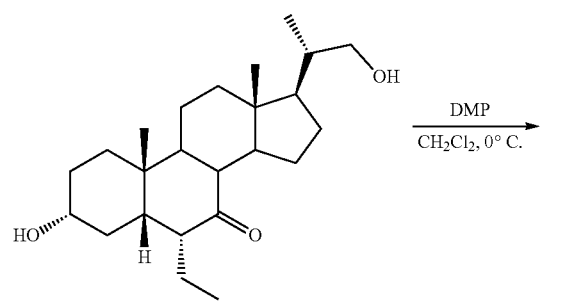

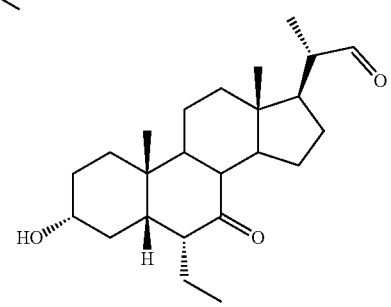

To a solution of (3α, 5β, 6α, 20S)-6-ethyl-3-hydroxy-7-oxo-23,24-dinor-cholane-22-ol (0.5 g, 1.33 mmol) in CH$_2$Cl$_2$ (100 vol, 50 mL) at 0° C. under argon was charged in portions Dess Martin periodane (564 mg, 1.33 mmol)

over 20 mins. After 2.5 h (TLC, eluant 1:1 EtOAc:Heptane; visualized with Cerium Ammonium Molybdate stain) the reaction was quenched by the addition of 10% aq. Na$_2$SO$_4$/2% NaHCO$_3$ (10 mL) and the mixture stirred for 10 mins. The solution was diluted with EtOAc (100 mL) and H$_2$O (100 mL). The aqueous layer was separated and extracted with EtOAc (100 mL). The combined organic layers were washed with 1M aq. NaOH (50 mL), 5% aq. NaCl (100 mL), dried over Na$_2$SO$_4$, filtered and concentration in-vacuo at 40° C. Purification by column chromatography gave (3α, 5β, 6α)-6-ethyl-3-hydroxy-7-oxo-23,24-dinor-cholane-22-al as an opaque oil (229 mg) along with recovered starting material (144 mg). $^1$H NMR (700 MHz, CDCl$_3$): δ=9.57 (1H, d, J=3.4), 3.54 (1H, m), 2.69 (1H, dd, J=5.7, 13.0), 2.35 (2H, m), 2.26 (2H, m), 1.97-1.90 (2H, m), 1.85-1.68 (7H, m), 1.55-1.46 (4H, m), 1.41-1.34 (1H, m), 1.23 (3H, s), 1.22-1.15 (3H, m), 1.12 (3H, d, J=6.9), 1.01 (1H, m), 0.87 (1H, m), 0.81 (3H, t, J=7.4), 0.70 (3H, s). $^{13}$C NMR (176 MHz, CDCl$_3$): δ=212.4, 205.0, 71.1, 52.0, 50.6, 50.3, 49.8, 49.2, 48.4, 43.7, 43.2, 38.7, 35.7, 34.3, 31.8, 29.8, 27.1, 25.0, 23.5, 21.8, 18.8, 13.6, 12.5, 12.0

L. Synthesis of (3α, 5β, 6α)-6-ethyl-3-hydroxy-7-oxo-22-cholen-24-oic Acid Ethyl Ester

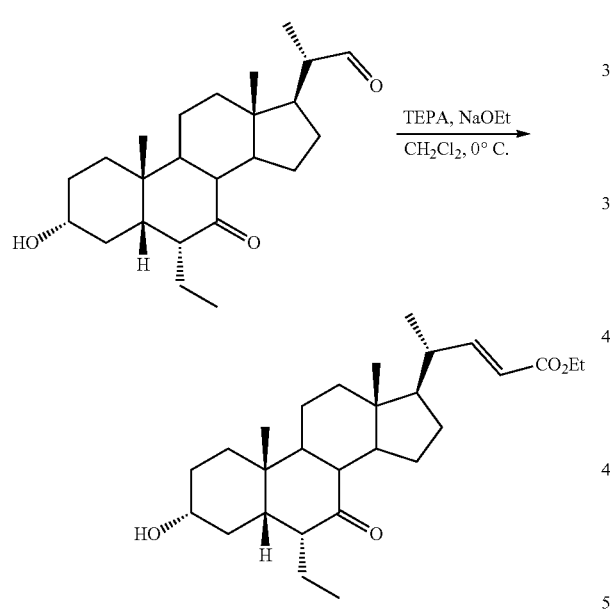

To a suspension of NaOEt (43 mg, 0.63 mmol) in CH$_2$Cl$_2$ (0.8 mL) at 0° C. was added dropwise TEPA and the solution warmed to ambient temperature. The TEPA/NaOEt mixture was then added dropwise to a solution of (3α, 5β, 6α)-6-ethyl-3-hydroxy-7-oxo-23, 24-dinor-cholane-22-al (195 mg, 0.52 mmol) in CH$_2$Cl$_2$ (4 mL) at 0° C. over 10 mins. The reaction was stirred at 0° C. for 1 h and then ambient temperature for 1 h. The reaction mixture was then re-cooled to 0° C. and a further aliquot of the TEPA/NaOEt mixture added. The reaction was stirred at 0° C. and after 0.5 h (TLC, eluant 1:1 EtOAc:Heptane; visualized with Cerium Ammonium Molybdate stain) H$_2$O (3 vol, 0.6 mL) was added and the reaction mixture warmed to ambient temperature. The solution diluted with CH$_2$Cl$_2$ (10 mL) and washed with H$_2$O (10 mL). The aqueous layer was separated and extracted with CH$_2$Cl$_2$ (10 mL). The combined organic layers were washed with 5% aq. NaCl (10 mL), dried over Na$_2$SO$_4$, filtered and concentrated. Purification by column chromatography gave (3α, 5β, 6α)-6-ethyl-3-hydroxy-7-oxo-22-cholen-24-oic acid ethyl ester as an opaque oil (130 mg). $^1$H NMR (700 MHz, CDCl$_3$): δ=6.82 (1H, dd, J=9.0, 15.5), 5.72 (1H, d, J=15.5), 4.17 (2H, q, J=7.1), 3.53 (1H, m), 2.69 (1H, dd, J=5.8, 13.0), 2.36 (1H, t, J=11.3), 2.26 (1H, m), 2.17 (1H, m), 1.85-1.68 (9H, m), 1.47 (3H, m), 1.28 (3H, t, J=7.3), 1.27-1.23 (3H, m), 1.22 (3H, s), 1.20-1.10 (3H, m), 1.08 (3H, d, J=6.7), 0.97-0.83 (2H, m), 0.80 (3H, t, J=7.4), 0.68 (3H, s). $^{13}$C NMR (176 MHz, CDCl$_3$): δ=212.6, 167.1, 154.5, 119.1, 71.1, 60.2, 54.0, 52.0, 50.6, 49.9, 48.9, 43.7, 42.9, 39.5, 38.8, 35.7, 34.3, 31.8, 29.9, 28.2, 24.7, 23.5, 21.8, 19.4, 18.8, 14.3, 12.4, 12.0.

M. Synthesis of (3α, 5β, 6α)-6-ethyl-3-hydroxy-7-oxo-cholan-24-oic Acid Ethyl Ester

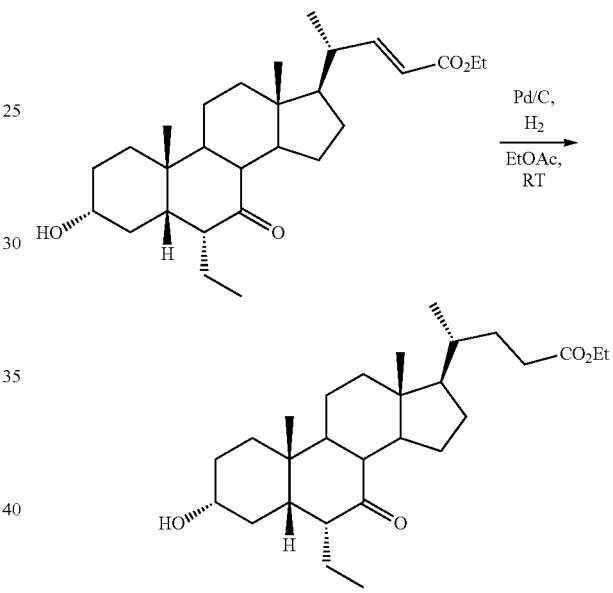

10% Palladium on Carbon (53 mg) was charged to a flask under argon. (3α, 5β, 6α)-6-ethyl-3-hydroxy-7-oxo-22-cholen-24-oic acid ethyl ester (107 mg, 0.24 mmol) dissolved in EtOAc (5.4 mL) was charged and the reaction purged with argon and then H$_2$. After 16 h at ambient temperature (TLC, eluant 1:1 EtOAc:Heptane; visualized with Anisaldehyde stain) the reaction mixture was filtered through a 0.45 μm PTFE filter and the filter washed with EtOAc (10 mL). Concentration in-vacuo at 40° C. gave (3α, 5β, 6α)-6-ethyl-3-hydrox-7-oxo-cholan-24-oic acid ethyl ester as a clear oil (86 mg). $^1$H NMR (700 MHz, CDCl$_3$): δ=4.12 (2H, ddd, J=1.5, 7.1, 14.2), 3.53 (1H, m), 2.69 (1H, dd, J=5.7, 13.0), 2.35 (2H, m), 2.20 (2H, m), 2.00-1.90 (2H, m), 1.85-1.66 (9H, m), 1.50-1.39 (4H, m), 1.36-1.29 (2H, m), 1.25 (3H, t, J=7.1), 1.21 (3H, s), 1.20-1.08 (4H, m), 0.92 (3H, d, J=6.6), 0.90-0.82 (2H, m), 0.80 (3H, t, J=7.4), 0.65 (3H, s). $^{13}$C NMR (176 MHz, CDCl$_3$): δ=212.8, 174.3, 71.2, 60.2, 54.8, 52.0, 50.7, 49.9, 49.0, 43.7, 42.7, 39.0, 35.7, 35.2, 34.3, 31.8, 31.3, 31.0, 29.9, 28.3, 24.6, 23.5, 21.9, 18.8, 18.4, 14.3, 12.1, 12.0.

N. Synthesis of (3α, 5β, 6α)-6-ethyl-3-hydrox-7-oxo-cholan-24-oic Acid

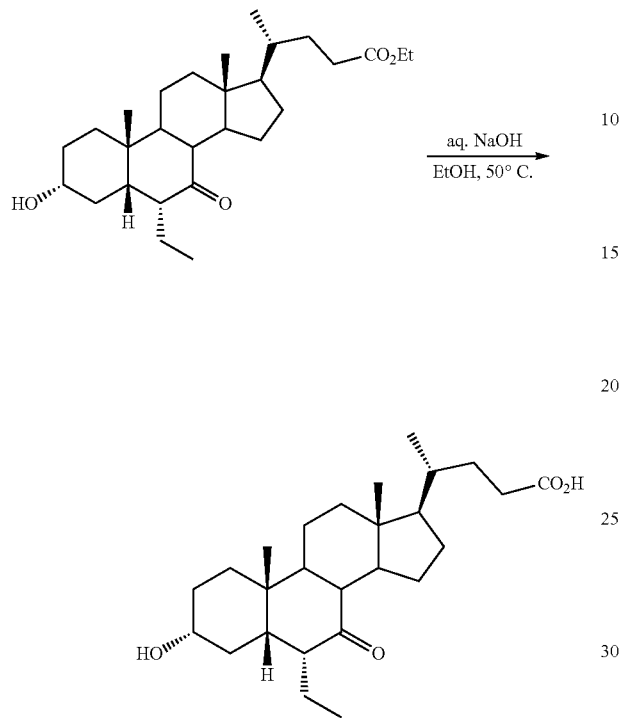

To a solution of (3α, 5β, 6α)-6-ethyl-3-hydrox-7-oxoy-cholan-24-oic acid ethyl ester (73 mg, 0.16 mmol) in EtOH (1 mL) at 50° C. was added dropwise 0.5M aq. NaOH (0.72 mL, 0.36 mmol). The reaction was heated at 50° C. for 1 h (TLC, eluent 1:1 EtOAc:Heptane; visualized with Cerium Ammonium Molybdate stain), quenched by the addition of 2M aq. HCl (1 mL) and then diluted with $H_2O$ (10 mL) and EtOAc (10 mL). The phases were separated and the aqueous phase extracted with EtOAc (2×10 mL). The combined organic phases were washed with 5% aq. NaCl (2×10 mL), dried over $Na_2SO_4$, filtered and concentrated in-vacuo at 40° C. Purification by column chromatography gave (3α, 5β, 6α)-6-ethyl-3-hydrox-7-oxo-cholan-24-oic acid as an oil (54 mg). $^1$H NMR (700 MHz, $CDCl_3$): δ=3.53 (1H, m), 2.69 (1H, dd, J=6.1, 12.9), 2.37 (2H, m), 2.25 (1H, m), 2.18 (1H, m), 2.0-1.89 (2H, m), 1.85-1.68 (7H, m), 1.50-1.40 (4H, m), 1.38-1.23 (5H, m), 1.22 (3H, s), 1.20-1.09 (4H, m), 0.93 (3H, d, J=6.6), 0.91-0.83 (2H, m), 0.80 (3H, t, J=7.4), 0.65 (3H, s) $^{13}$C NMR (176 MHz, $CDCl_3$): δ=213.0, 179.6, 71.2, 54.8, 52.0, 50.7, 49.9, 49.0, 43.7, 42.7, 39.0, 35.7, 35.2, 34.3, 31.7, 31.0, 30.8, 29.8, 28.3, 24.6, 23.5, 21.9, 18.8, 18.4, 12.1, 12.0.

Examples 1 to 7 illustrate how the various side chains $YR^4$ of the compounds of general formula (I) can be inter-converted and how the compounds of general formula (IA), (IB), (IC), (ID), (IE) and (IF) can be converted to the required products of general formula (XXI).

The invention claimed is:

1. A compound of general formula (I):

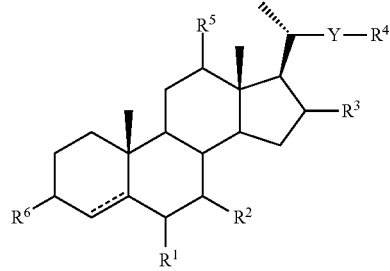

wherein:

⟋ is a carbon-carbon single or double bond;

$R^1$ is $C_{1-4}$ alkyl optionally substituted with one or more substituents selected from halo, $OR^{7a}$ and $NR^{7a}R^{7b}$; where each of $R^{7a}$ and $R^{7b}$ is independently selected from H and $C_{1-4}$ alkyl;

or $R^1$ together with $R^2$ forms an epoxide group;

$R^2$ is selected from the group consisting of =O, OH and a protected OH or $R^2$ together with $R^1$ forms an epoxide group;

$R^3$ is selected from the group consisting of H, halo, OH and a protected OH;

when ⟋ is a carbon-carbon double bond, Y is selected from the group consisting of a bond and an alkylene, alkenylene or alkynylene linker group having from 1 to 20 carbon atoms and optionally substituted with one or more groups $R^{13}$;

when ⟋ is a carbon-carbon single bond, Y is selected from the group consisting of a bond and an alkylene linker group having from 1 to 20 carbon atoms and optionally substituted with one or more groups $R^{13}$; or Y, together with $R^4$ forms a group =$CH_2$;

each $R^{13}$ is independently selected from halo, $OR^8$ and $NR^8R^9$;

where each of $R^8$ and $R^9$ is independently selected from H and $C_{1-4}$ alkyl;

$R^4$ is selected from the group consisting of halo, CN, $CH(OR^{10})(OR^{11})$, $CH(SR^{10})SR^{11}$, $NR^{10}R^{11}$, $BR^{10}R^{11}$, $C(O)CH_2N_2$, —CH=$CH_2$, —C≡CH, $CH[C(O)OR^{10}]_2$, $CH(BR^{10}R^{11})_2$, azide and a carboxylic acid mimetic group selected from —$SO_2$—$NHR^{30}$, C(O)NH—$SO_2R^{30}$, NHC(O)NH—$SO_2R^{30}$ and tetrazole optionally substituted with one or more substituents selected from $C_{1-4}$ alkyl, halo, OH, O($C_{1-4}$ alkyl), $SO_2(C_{1-4}$ alkyl), $SO_2$-phenyl and $SO_2$-tolyl;

where $R^{30}$ is selected from H, $C_{1-6}$ alkyl $C_{3-7}$ cycloalkyl or aryl optionally substituted with $C_{1-4}$ alkyl, halo, OH, O($C_{1-4}$ alkyl), $SO_2(C_{1-4}$ alkyl), $SO_2$-phenyl or $SO_2$-tolyl;

where each $R^{10}$ and $R^{11}$ is independently selected from:
a. hydrogen and
b. $C_{1-20}$ alkyl, $C_{2-20}$ alkenyl or $C_{2-20}$ alkynyl, any of which is optionally substituted with one or more substituents selected from halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$, $N(R^{19})_2$ and a 6- to 14-membered aryl or 5 to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$ and $N(R^{19})_2$; and c. a 6- to 14-membered aryl or 5 to 14-membered heteroaryl group either of which is optionally substituted with one or more substituents selected from $C_{1-6}$ alkyl, $C_{1-6}$ haloalkyl, halo, $NO_2$, CN, $OR^{19}$, $SR^{19}$, $C(O)OR^{19}$, $C(O)N(R^{19})_2$, $SO_2R^{19}$, $SO_3R^{19}$, $OSO_3R^{19}$ and $N(R^{19})_2$; and d. a polyethylene glycol residue; or e. when $R^4$ is $CH(OR^{10})(OR^{11})$, $CH(SR^{10})(SR^{11})$, $NR^{10}R^{11}$, $BR^{10}R^{11}$, $CH[C(O)OR^{10}]_2$ or $CH(BR^{10}R^{11})_2$ an $R^{10}$ and an $R^{11}$ group, together with the atom or atoms to which they are attached, may combine to form a 3 to 10-membered heterocyclic ring;

each $R^{19}$ is independently selected from H, $C_{1-6}$ alkyl, $C_{1-6}$ haloalkyl and a 6- to 14-membered aryl or 5 to 14-membered heteroaryl group either of which is optionally substituted with one or more substituents selected from halo, $C_{1-6}$ alkyl and $C_{1-6}$ haloalkyl; or $R^5$ is selected from the group consisting of H, OH and a protected OH group;

$R^6$ is =O;

and salts thereof.

2. The compound according to claim 1 selected from the group consisting of:

a compound of general formula (IA):

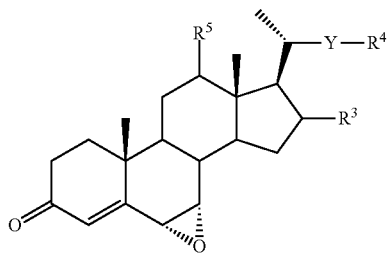

(IA)

wherein $R^3$, Y, $R^4$ and $R^5$ are as defined for general formula (I); a compound of general formula (IB):

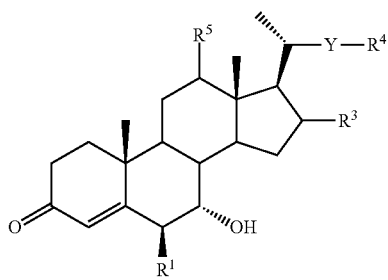

(IB)

wherein $R^1$, $R^3$, Y, $R^4$ and $R^5$ are as defined for general formula (I);

a compound of general formula (IC):

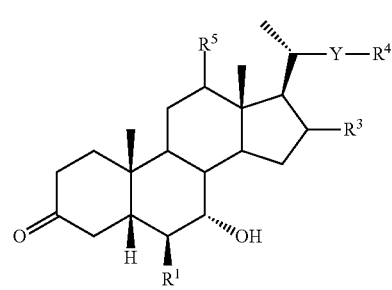

(IC)

wherein $R^1$, $R^3$, Y, $R^4$ and $R^5$ are as defined for general formula (I);

a compound of general formula (ID):

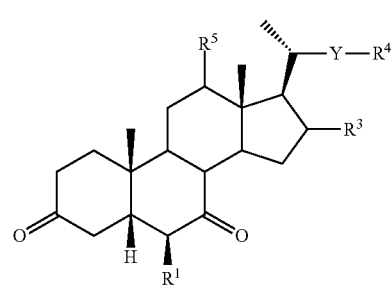

(ID)

wherein $R^1$, $R^3$, Y, $R^4$ and $R^5$ are as defined for general formula (I); and a compound of general formula (IE):

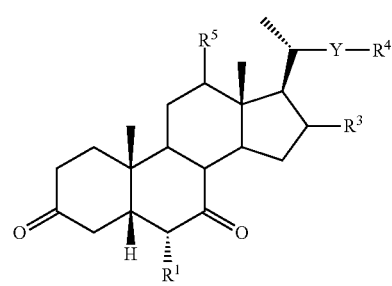

(IE)

wherein $R^1$, $R^3$, Y, $R^4$ and $R^5$ are as defined for general formula (I);

and salts of any of these.

3. The compound according to claim 1 wherein $R^1$ is ethyl.

4. The compound according to claim 1 wherein the compound is a compound of general formula (IA) or (IB) and Y is selected from the group consisting of a bond, an unsubstituted $C_{1-3}$ alkylene group, a $C_{1-3}$ alkylene group substituted with OH, and a $C_{1-3}$ alkenylene group.

5. The compound according to claim 1 wherein the compound is selected from the group consisting of a compound of general formula (IC), a compound of general formula (ID) and a compound of general formula (IE) and Y selected from a bond and an alkylene group having 1 to 3 carbon atoms and is optionally substituted with one or two OH groups.

6. The compound according to claim 1 wherein, when present in the $R^4$ moiety, each $R^{10}$ and $R^{11}$ is independently selected from:
   a. hydrogen and
   b. $C_{1-10}$ alkyl, $C_{2-10}$ alkenyl or $C_{2-10}$ alkynyl, any of which is optionally substituted with one or more substituents as defined in claim 1; and
   c. a 6- to 10-membered aryl or 5 to 10-membered heteroaryl group either of which is optionally substituted with one or more substituents as defined in claim 1; and
   d. a polyethylene glycol residue; or
   e. when $R^4$ is selected from the group consisting of $CH(OR^{10})(OR^{11})$, $CH(SR^{10})(SR^{11})$, $NR^{10}R^{11}$, $BR^{10}R^{11}$, or $CH[C(O)OR^{10}]_2$ or $CH(BR^{10}R^{11})_2$ an $R^{10}$ and an $R^{11}$ group, together with the atom or atoms to which they are attached, may combine to form a 3- to 10-membered heterocyclic ring; or
   when $R^4$ is $NR^{10}R^{11}$, $R^{10}$ may be selected from H and $C_{1-4}$ alkyl and $R^{11}$ may be a 5-10 membered heteroaryl group.

7. The compound according to claim 1 wherein:
   when one or more of $R^2$, $R^3$ and $R^5$ is a protected OH group, the protected OH group comprises
   i. $OC(O)R^{14}$, where $R^{14}$ is a group $R^{10}$; or
   ii. $OSi(R^{16})_3$,
   and wherein:
   when present, one or more of $R^{10}$, $R^{11}$ and $R^{16}$ is selected from:
   a. an alkyl, alkenyl or alkynyl group optionally substituted with one or more substituents selected from halo, $NO_2$, CN, $OR^{19}$, $SR^{19}$, $C(O)OR^{19}$, $SO_2R^{19}$, $SO_3R^{19}$, $OSO_3R^{19}$, $N(R^{19})_2$ and a 6- to 10-membered aryl or 5 to 14-membered heteroaryl group, either of which is optionally substituted with a group selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; where $R^{19}$ is as defined in claim 1; or
   b. an aryl or heteroaryl group optionally substituted with one or more substituents selected from $C_{1-6}$ alkyl, $C_{1-6}$ haloalkyl, halo, $NO_2$, CN, $OR^{19}$, $SR^{19}$ and $N(R^{19})_2$; where $R^{19}$ is as defined in claim 1.

8. The compound according to claim 1 wherein, when present, $R^{19}$ is selected from H, methyl, ethyl, trifluoromethyl and phenyl optionally substituted with one or more substituents selected from fluoro, chloro, methyl, ethyl and trifluoromethyl.

9. The compound according to claim 1, wherein $R^4$ is selected from the group consisting of halo, CN, $CH(OR^{10})(OR^{11})$, $NR^{10}R^{11}$, $BR^{10}R^{11}$, —CH=CH$_2$, —C≡CH, $CH[C(O)OR^{10}]_2$, azide, and $CH(BR^{10}R^{11})_2$;
   wherein $R^{10}$ and $R^H$ are as defined in claim 1.

10. The compound according to claim 9, wherein $R^4$ is selected from the group consisting of halo, CN, $CH(OR^{10})(OR^{11})$, $NR^{10}R^{11}$, $CH[C(O)OR^{10}]_2$, azide and tetrazole;
   wherein $R^{10}$ is selected from H and $C_{1-10}$ alkyl, $C_{2-10}$ alkenyl or $C_{2-10}$ alkynyl optionally substituted with one or more substituents selected from halo, $NO_2$, CN, $OR^{19}$, $SR^{19}$, $C(O)OR^{19}$, $SO_2R^{19}$, $SO_3R^{19}$, $OSO_3R^{19}$, $N(R^{19})_2$ and a 6- to 10-membered aryl or 5 to 14-membered heteroaryl group, either of which is optionally substituted with one or more substituents selected from $C_{1-6}$ alkyl, $C_{1-6}$ haloalkyl, halo, $NO_2$, CN, $OR^{19}$, $SO_2R^{19}$, $SO_3R^{19}$ and $N(R^{19})_2$; wherein $R^{19}$ is as defined in claim 1; or
   when $R^4$ is $CH(OR^{10})(OR^{11})$, the $OR^{10}$ and $OR^{11}$ groups together with the carbon atom to which they are attached may form a cyclic acetal group; or
   when $R^4$ is $N^{10}R^{11}$, is selected from H and $C_{1-4}$ alkyl and $R^{11}$ is a 5-10 membered heteroaryl group.

11. The compound according to claim 10, wherein $R^4$ is selected from the group consisting of:
   Cl, Br, CN, $CH(OR^{10})_2$, 1,3-dioxane, 1,3-dioxolane, $CH[C(O)OR^{10}]_2$ and tetrazole; where $R^{10}$ is selected from methyl, ethyl, n-propyl, isopropyl, n-butyl, s-butyl, iso-butyl and t-butyl.

12. The compound according to claim 10 wherein $R^4$ is azide.

13. The compound according to claim 9 wherein $R^4$ is selected from —NH— tetrazole, —C(O)NHSO$_2$R$^{30}$ and —NHC(O)NHSO$_2$R$^{30}$; wherein $R^{30}$ is as defined in claim 9.

14. The compound according to claim 1 which is selected from the group consisting of:
   (6α, 7α, 20S)-20-(1-bromomethyl)-6,7-epoxy-pregn-4-en-3-one;
   (6α, 7α, 20S)-6,7-epoxy-20-(ethylenedioxymethyl)-pregn-4-en-3-one;
   (6α, 7α, 20S)-6,7-epoxy-20-azidomethyl-pregna-4-en-3-one;
   (6α, 7α)-6,7-epoxy-3-oxo-4-cholen-23-carboxy-24-oic acid dimethyl ester;
   (6α, 7α)-6-ethyl-7-hydroxy-3-oxo-4-cholen-23-carboxy-24-oic acid dimethyl ester;
   (5β, 6β, 7α)-6-ethyl-7-hydroxy-3-oxo-cholan-23-carboxy-24-oic acid dimethyl ester;
   (5β, 6β)-6-ethyl-3,7-dioxo-cholan-23-carboxy-24-oic acid dimethyl ester;
   (5β, 6α)-6-ethyl-3,7-dioxo-cholan-23-carboxy-24-oic acid dimethyl ester;
   (5β, 6α)-6-ethyl-3,7-dioxo-cholan-23-carboxy-24-oic acid;
   (6α, 7α)-6,7-epoxy-3-oxo-4-choleno-24-nitrile;
   (6β, 7α)-6-ethyl-7-hydroxy-3-oxo-4-choleno-24-nitrile;
   (5β, 6β, 7α)-6-ethyl-7-hydroxy-3-oxo-cholano-24-nitrile;
   (5β, 6β)-3,7-dioxo-6-ethyl-cholano-24-nitrile;
   (3α, 5β, 6β)-6-ethyl-3-hydroxy-7-oxo-cholano-24-nitrile;
   (6α, 7α, 20R)-20-(1-cyanomethyl)-6,7-epoxy-pregn-4-en-3-one;
   (6β, 7α, 20R)-cyanomethyl-6-ethyl-7-hydroxy-4-pregnen-3-one;
   (5β, 6β, 7α, 20R)-cyanomethyl-6-ethyl-7-hydroxy-pregna-3-one;
   (5β, 6β, 20R)-cyanomethyl-6-ethyl-7-oxo-pregna-3-one;
   (6β, 7α, 20S)-20-(ethylenedioxymethyl)-6-ethyl-7-hydroxy-pregna-4-en-3-one;
   (5β, 6β, 7α, 20S)-20-(ethylenedioxymethyl)-6-ethyl-7-hydroxy-pregna-3-one;
   (5β, 6β, 20S)-20-(ethylenedioxymethyl)-6-ethyl-pregna-3,7-dione;
   (5β, 6α, 20S)-20-(ethylenedioxymethyl)-6-ethyl-pregna-3,7-dione;
   and salts thereof.

15. The compound according to claim 1, wherein the carboxylic acid mimetic group is selected from tetrazole, —C(O)NHSO$_2$R$^{30}$ and —NHC(O)NHSO$_2$R$^{30}$; wherein $R^{30}$ is H, $C_{1-6}$ alkyl or aryl.

* * * * *